US008389210B2

(12) United States Patent
Croce et al.

(10) Patent No.: US 8,389,210 B2
(45) Date of Patent: Mar. 5, 2013

(54) MICRORNA EXPRESSION ABNORMALITIES IN PANCREATIC ENDOCRINE AND ACINAR TUMORS

(75) Inventors: Carlo M. Croce, Columbus, OH (US); George A. Calin, Pearland, TX (US)

(73) Assignee: The Ohio State University Research Foundation, Columbus, OH (US)

( * ) Notice: Subject to any disclaimer, the term of this patent is extended or adjusted under 35 U.S.C. 154(b) by 268 days.

(21) Appl. No.: 12/700,286

(22) Filed: Feb. 4, 2010

(65) Prior Publication Data

US 2010/0197774 A1 Aug. 5, 2010

Related U.S. Application Data

(62) Division of application No. 12/160,064, filed on Jul. 3, 2008, now Pat. No. 7,670,840.

(60) Provisional application No. 60/756,502, filed on Jan. 5, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6; 435/91.1; 435/91.31; 536/23.1; 536/24.31; 536/24.5

(58) Field of Classification Search ............. 435/6, 91.1, 435/91.31; 536/23.1, 24.1, 24.31, 24.3
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,888,010 B2 | 2/2011 | Brown et al. |
| 7,919,245 B2 | 4/2011 | Brown et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |

(Continued)

FOREIGN PATENT DOCUMENTS

CA 2533701 A1 2/2005
CA 2587189 12/2006

(Continued)

OTHER PUBLICATIONS

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

(Continued)

Primary Examiner — Jane Zara
(74) Attorney, Agent, or Firm — MacMillan, Sobanski & Todd, LLC

(57) ABSTRACT

The present invention provides novel methods and compositions for the diagnosis, prognosis and treatment of pancreatic cancer. The invention also provides methods of identifying anti-pancreatic cancer agent.

64 Claims, 7 Drawing Sheets
(4 of 7 Drawing Sheet(s) Filed in Color)

U.S. PATENT DOCUMENTS

| | | |
|---|---|---|
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0199961 A1* | 8/2008 | Rasko et al. .................. 435/455 |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |
| 2012/0065248 A1* | 3/2012 | Brown et al. ................ 514/44 A |

FOREIGN PATENT DOCUMENTS

| | | |
|---|---|---|
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 0076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005013901 A3 | 2/2005 |
| WO | 2005/020795 | 3/2005 |
| WO | 2005060661 | 7/2005 |
| WO | 2005/078139 | 8/2005 |
| WO | 2005/080601 | 9/2005 |
| WO | 2005079397 A2 | 9/2005 |
| WO | 2005103298 A2 | 11/2005 |
| WO | 2005/118806 | 12/2005 |
| WO | 2006/105486 | 10/2006 |
| WO | 2006/108718 | 10/2006 |
| WO | 2006108718 | 10/2006 |
| WO | 2006/119266 | 11/2006 |

| | | |
|---|---|---|
| WO | 2006/133022 | 12/2006 |
| WO | 2006/137941 | 12/2006 |
| WO | 2007/016548 | 2/2007 |
| WO | 2007016548 A2 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007112754 A2 | 10/2007 |
| WO | 2007/127190 | 11/2007 |
| WO | 2008/008430 | 1/2008 |
| WO | 2008/036168 A2 | 3/2008 |
| WO | 2008/036776 | 3/2008 |
| WO | 2008/054828 | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Bartel, D. P., "MicroRNAs: Target Recognition and Regulatory Functions," Cell, Jan. 2009, pp. 215-233, vol. 136.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Dalmay, T. et al., "MicroRNAs and the Hallmarks of Cancer," Oncogene, 2006, pp. 6170-6175, vol. 25.
Davies, F. E. et al., "Insights into the Multistep Transformation of MGUS to Myeloma Using Microarray Expression Analysis," Blood, Dec. 2003, pp. 4504-4511, vol. 102, No. 13.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, etal., "FHIT," Atlas of Genetics and Cytogenetics in Oncology and Haematology, 2007, pp. 171-178, vol. 2.
Eis, P. S. et al., "Accumulation of miR-155 and BIC RNA in Human B Cell Lymphomas," PNAS, Mar. 2005, pp. 3627-3632, vol. 102, No. 10.
European Patent Application, EP 1795203 A2, Croce et al., Application No. 06010581.4, filed Feb. 7, 1997, published Jun. 13, 2007.
European Search Report, Application No. 06800599.0 dated Oct. 19, 2009.
European Search Report, Application No. 06814375.9 dated Oct. 8, 2009.

European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep. 14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 08796821.0 dated Aug. 4, 2010.
European Search Report, Application No. 08841700.1 dated Jun. 2, 2010.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth In Vitro and In Vivo," PNAS, Oct. 2005, pp. 15611-15616, vol. 102, No. 43.
Fong, Y. et al., "Muir-Torre-Like Syndrome in FHIT-Deficient Mice," PNAS, Apr. 2000, pp. 4742-4747, vol. 97, No. 9.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Johnson, S. M. et al., "RAS is Regulated by the let-7 MicroRNA Family," Supplemental Data, Cell, Mar. 2005, pp. 635-647, vol. 120.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.
Krek, A. et al., "Combinatorial MicroRNA Target Predictions," Nature Genetics, May 2005, pp. 495-500, vol. 37, No. 5.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Lee, E. J. et al., "Expression Profiling Identifies MicroRNA Signature in Pancreatic Cancer," Int. J. Cancer, 2006, pp. 1046-1054, vol. 120.
Lewis, B. P. et al., "Prediction of Mammalian MicroRNA Targets," Cell, Dec. 2003, pp. 787-798, vol. 115.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Lu, J. et al., "MicroRNA Expression Profiles Classify Human Cancers," Nature, Jun. 2005, pp. 834-838, vol. 435, Supplementary Information.
Lu, J. et al., "MicroRNA Expression Profiles Classify Human Cancers," Nature, Jun. 2005, pp. 834-838, vol. 435.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pp., vol. 5, No. 24.
McManus, M. T., "MicroRNAs and Cancer," Seminars in Cancer Biology, 2003, pp. 253-258, vol. 13.
Megraw, M. et al., "miRGen: A Database for the Study of Animal MicroRNA Genomic Organization and Function," Nucleic Acids Research, 2007, pp. D149-D155, vol. 35.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 3, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.

PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 15, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 12, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, a. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.
Thomson, J. M. et al., "A Custom Microarray Platform for Analysis of MicroRNA Gene Expression," Nature Methods, Oct. 2004, pp. 1-7, vol. 1, No. 1.
Thorgeirsson, S. S. et al., "Functional Genomics of Hepatocellular Carcinoma," Hepatology, Feb. 2006, pp. S145-S150, vol. 43, No. 2, Suppl. 1.
Tockman, M. S. et al., "Considerations in Bringing a Cancer Biomarker to Clinical Application," Cancer Research, May 1992, pp. 2711s-2718s, vol. 52.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Valeri, N. et al., "Epigenetics, miRNAs, and Human Cancer: A New Chapter in Human Gene Regulation," Mamm Genome, Aug. 2009, pp. 573-580, vol. 20.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.
Wang, X. et al., "Association Between CpG Island Methylation of the WWOX Gene and Its Expression in Breast Cancers," Tumor Biology, Feb. 2009, pp. 8-14, vol. 30.
Weidhaas, J., "Using MicroRNAs to Understand Cancer Biology," Published Online Dec. 21, 2009, DOI: 10.1016/S1470-2045(09)70386-9.
Yamashita, T. et al., "Activation of Hepatic Stem Cell Marker EpCAM by Wnt-β-Catenin Signaling in Hapatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.
Yanaihara, N. et al., "Unique MicroRNA Molecular Profiles in Lung Cancer Diagnosis and Prognosis," Cancer Cell, Mar. 2006, pp. 189-198, vol. 9.
Yang, J. et al., "Analysis of Sequence Variations in 59 MicroRNAs in Hepatocellular Carcinomas," Mutation Research, Aug. 2008, pp. 205-209, vol. 638.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yoon, S. et al., "Prediction of Regulatory Modules Comprising MicroRNAs and Target Genes," Bioinformatics Genes and Genomes, 2005. Pages ii93-ii100, vol. 21, Suppl. 2.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.
Ambros, V. et al., "A Uniform System for MicroRNA Annotation," RNA, 2003, pp. 277-279, vol. 9.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Caldas, C. et al., "Sizing Up miRNAs as Cancer Genes," Nature Medicine, Jul. 2005, pp. 712-714, vol. 11, No. 7.
Canadian Intellectual Property Office, Requisition by the Examiner, Application No. 2,635,616, Dated Feb. 21, 2011.
Cui, S. et al., "MicroRNAs that Underlie Ovarian Cancer Development and Response to Chemotherapy," 98th AACR Annual Meeting, Apr. 14-18, 2007, Los Angeles, CA.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219, XP002612580.
Esquela-Kerscher, A. et al., "Oncomirs—MicroRNAs with a Role in Cancer," Nature Reviews:Cancer, Apr. 2006, pp. 259-269, vol. 6.
European Search Report, Application No. 08798444.9-2402, PCT/US2008/073964, dated Dec. 16, 2010.
European Search Report, Application No. 08799295.4-2402, PCT/US2008/075565, dated Nov. 9, 2010.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Flavin, Rj et al., "MicroRNA Gene Expression Profiling in Human Ovarian and Primary Peritoneal Serous Carcinomas" USCAP 96th Annual Meeting, Abstract #897, San Diego, CA, Mar. 2007.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffiths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
He, X. et al., "MicroRNA and Esophageal Carcinoma," Journal of Nanjing Medical University, 2007, pp. 201-206, vol. 21, No. 4.
Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.
Kozomara, A. et al., "miRBase: Integrating MicroRNA Annotation and Deep-Sequencing Data," Nucleic Acids Research, 2011, pp. D152-D157, vol. 39.
Li, S.-C. et al., "Bioinformatic Discovery of MicroRNA Precursors from Human ESTs and Introns," BMC Genomics, 2006, vol. 7.

Lujambio, A. et al., "A MicroRNA DNA Methylation Signature for Human Cancer Metastasis," PNAS, Sep. 2008, pp. 13556-13561, vol. 105, No. 36.

Medina, P.P. et al., "OncomiR Addiction in an In Vivo Model of MicroRNA-21-Induced Pre-B-Cell Lymphoma," Nature Letters, Sep. 2010, pp. 86-91, vol. 467.

Medina, P.P., "OncomiR Addicton in an in vivo Model of Micro-RNA-21-Induced Pre-B-Cell Lymphoma," Supplementary Information, Sep. 2010, p. 1-22.

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.

Nicoloso, M.S. et al., "MicroRNAs- The Micro Steering Wheel of Tumour Metastases," Nature Reviews: Cancer, Apr. 2009, pp. 293-302, vol. 9.

Nurden, A.T., "Qualitative Disorders of Platelets and Megakaryocytes," Journal of Thrombosis and Haemostasis, 2005, vol. 3, pp. 1773-1782.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Saini, H. K. et al., "Annotation of Mammalian Primary MicroRNAs," BMC Genomics, 2008, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Slack, F.J., "Big Roles for Small RNAs," Nature, Feb. 2010, p. 616, vol. 463.

State Intellectual Property Office of the People's Republic of China, Notification of the First Office Action, Application No. 200780005791.5, dated Mar. 24, 2011.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Valeri, N. et al., "Modulation of Mismatch Repair and Genomic Stability by miR-155," PNAS, Apr. 2010, pp. 6982-6987, vol. 107, No. 15.

Wijermans, P.W., "Low Dose Azanucleosidesfor High Risk (s) MDS and AML," Haematologica Reports, Nov. 2006, pp. 74-76. vol. 2, Issue, 15.

PCT International Preliminary Report on Patentability, PCT/US2009/065072 filed Nov. 19, 2009, dated Jun. 3, 2011.

PCT International Preliminary Report on Patentability, PCT/US2009/038214 filed Mar. 25, 2009, dated Jun. 16, 2011.

European Search Report, Application No. 11151771-0, dated Feb. 8, 2011.

European Seach Report, Application No. 11151749.6, dated Feb. 8, 2011.

European Search Report, Application No. 11151772-8, dated Feb. 8, 2011.

European Communication Pursuant to Article 94(3) EPC, Application No. 08767439.9, dated Mar. 15, 2011.

European Communication Pursuant to Article 94(3) EPC, Application No. 07867402.5, dated Jan. 5, 2011.

European Seach Report, Application No. 09714868.8 dated Aug. 1, 2011.

PCT International Preliminary Report on Patentability, PCT/US2010/025173 filed Feb. 24, 2010, dated Sep. 9, 2011.

European Search Report, Application No. 09713926.5 dated Jul. 21, 2011.

European Search Report, Application No. 08713330.2, dated Jul. 22, 2011.

European Search Report, Application No. 11151769-4, dated Feb. 8, 2011.

Canadian Office Action, Application No. 2,621,441, dated Feb. 1, 2011.

EP Search Report, Application No. 08782609.5 dated Oct. 28, 2010.

Chinese Office Action, Application No. 200780005821.2 dated Jan. 26, 2011.

Australian Office Action, Application No. 2006291165 dated Aug. 23, 2011.

Chinese Office Action, Application No. 200680039776.8 dated Jun. 30, 2011.

European Communication Pursuant to Article 94(3) EPC, Application No. 07810382.7, dated Dec. 8, 2010.

European Communication Pursuant to Article 94(3) EPC, Application No. 08768266.2, dated Apr. 18, 2011.

European Search Reoprt, Application No. 08841700.1, dated Jan. 4, 2011.

Canadian Office Action, Application No. 2,617,581, dated Feb. 1, 2011.

European Communication Pursuant to Article 94(3) EPC, Application No. 07716208.9, dated Sep. 13, 2011.

Chinese Office Action, Application No. 200780040146.7 dated May 25, 2011.

European Supplementary Search Report, Application No. 09715064.3 dated May 24, 2011.

Chinese Office Action, Application No. 200680036598.3 dated Feb. 24, 2011.

Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.

Baira, E. et al., "Ultraconserved Elements: Genomics, Function and Disease," RNA Biology, Jul. 2008, pp. 132-134, vol. 5, No. 3.

Boland, C.R. et al., "Lynch Syndrome: Form, Function, Proteins, and Basketball," Gastroenterology, Aug. 2005, pp. 751-755, vol. 129, No. 2.

Cannistra, S.A., "Cancer of the Ovary," The New England Journal of Medicine, 2004, pp. 2519-2529, vol. 351, No. 25.

Castoldi, M. et al., "A Sensitive Array for MicroRNA Expression Profiling (miChip) Based on Locked Nucleic Acids (LNA)," RNA, 2006, pp. 913-920, vol. 12.

Chim, S.S.C. et al., "Detection and Characterization of Placental MicroRNAs in Maternal Plasma," Clinical Chemistry, 2008, pp. 482-490, vol. 54, No. 3.

Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.

Feng, G. et al., "Elevated Serum-Circulating RNA in Patients with Conventional Renal Cell Cancer," Anticancer Research, 2008, pp. 321-326, vol. 28.

Ford, L.P., "A MicroRNA Expression Signature of Human Solid Tumors Defines Cancer Gene Targets," Leukemia Research, 2006, pp. 511-513, vol. 30.

He, L. et al., "A MicroRNA Polycistron as a Potential Human Oncogene," Nature, Jun. 2005, pp. 828-833, vol. 435.

Ishii, H. et al., "Effect of Adenoviral Transduction of the Fragile Histidine Triad Gene into Esophageal Cancer Cells," Cancer Research, Feb. 2001, pp. 1578-1584, vol. 61.

Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.

Jacobs, I.J. et al., "Progress and Challenges in Screening for Early Detection of Ovarian Cancer," Molecular & Cellular Proteomics, 2004, pp. 355-366, vol. 3.

Jemal, A. et al., "Cancer Statistics, 2008," CA Cancer J. Clin., 2008, pp. 71-96, vol. 58, No. 2.

Lagos-Quintana, M. et al., "Identification of Tissue-Specific MicroRNAs from Mouse," Current Biology, Apr. 2002, pp. 735-739, vol. 12.

Landgraf, P. et al., "A Mammalian MicroRNA Expression Atlas Based on Small RNA Library Sequencing," Cell, Jun. 2007, pp. 1401-1414, vol. 129.

Lanza, G. et al., "mRNA/microRNA Gene Expression Profile in Microsatellite Unstable Colorectal Cancer," Molecular Cancer, 2007, pp. 1-11, vol. 6, No. 54.

Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.

Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.

Mendell, J.T., "miRiad Roles for the miR-17-92 Cluster in Development and Disease," Cell, 2008, pp. 217-.

Meng, F. et al., "MicroRNA-21 Regulates Expression of the PTEN Tumor Suppressor Gene in Human Hepatocellular Cancer," Gastroenterology, 2007, pp. 647-658, vol. 133.

Nam, E.J. et al., "MicroRNA Expression Profiles in Serous Ovarian Carcinoma," Clinical Cancer Research, 2008, pp. 2690-2695, vol. 14, No. 9.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Petrocca, F. et al., "MicroRNAs Deregulation in Gastric Cancer," PNAS, Apr. 2006, p. 1338, vol. 47, Abstract # 5690.

Porkka, K.P. et al., "MicroRNA Expression Profiling in Prostate Cancer," Cancer Research, 2007, pp. 6130-6135, vol. 67, No. 13.

Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Signal-Based Attachment Protein," Molecular Therapy, May 2006, pp. 997-1005, vol. 13, No. 5.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.

Thomson, M., Supplementary data for "A Custon Microarray Platform for Analysis of MicroRNA Gene Expression," Nature Methods, Oct. 2004, pp. 47-53, vol. 1, No. 1.

Tili, E. et al., "Expression and Function of Micro RNAs in Immune Cells During Normal or Disease State," International Journal of Medicine Sciences, 2008, pp. 73-79, vol. 5, No. 2.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Verschuur, A.C., "Acute Megakaryoblastic Leukemia," May 2004, pp. 1-5, Retrieved from the Internet: URL: http://www.orpga.net/data/patho/GB/uk-AMLM7.pdf.

Zawacka-Pankau, J. et al., "Expression and Simple, One-Step Purification of Fragile Histidine Triad (Fhit) Tumor Suppressor Mutant Forms in Escherichia coli and their Interaction with Protoporphyrin IX," Biotechnology Letters, Jun. 2007, pp. 877-883, vol. 29, No. 6.

EP Search Report, Application No. 12165638.3 dated Jun. 12, 2012.

EP Search Report, Application No. 12165636.7 dated Jun. 8, 2012.

Australian Government, Examiner's First Report, Appln. No. 2007243475, Dated Mar. 30, 2012.

Australian Office Action, Application No. 2007272947 dated May 21, 2012.

Australian Office Action, Application No. 2008266014 dated Jul. 6, 2012.

Australian Office Action, Application No. 2008248319 dated Jul. 12, 2012.

Australian Office Action, Application No. 2007346101 dated Jun. 21, 2012.

Chinese Office Action, Application No. 200880112585.9 dated May 24, 2012.

Chinese Office Action, Application No. 200780033066.9 dated Jun. 26, 2012.

Chinese Office Action, Application No. 200880116343.7 dated Jan. 31, 2011.

EP Search Report, Application No. 12154298.9 dated Jun. 4, 2012.

EP Search Report, Application No. 09715356.3 dated Jul. 12, 2012.

EP Search Report, Application No. 12154321.9 dated Jul. 20, 2012.

EP Search Report, Application No. 12154342.5 dated Jul. 6, 2012.

EP Search Report, Application No. 12154304.5 dated Jun. 26, 2012.

European Communication Pursuant to Article 94(3) EPC, Application No. 08841700.1, dated Jun. 1, 2012.

PCT International Preliminary Report on Patentability, PCT/US2010/057758 filed Nov. 23, 2010, dated Jun. 7, 2012.

PCT International Search Report and the Written Opinion, PCT/US2012/28016 filed Mar. 7, 2012, dated Aug. 3, 2012.

Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.

Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.

Garofalo, M. et al., "MicroRNA Signatures of TRAIL Resistance in Human Non-Small Cell Lung Cancer," Oncogene, 2007, pp. 3854-3855, vol. 27.

Lawrie, C. H. "MicroRNAs and Haematology: Small Molecules, Big Function," British Journal of Haematology, Jun. 2007, pp. 503-512, vol. 137, No. 6.

Lawrie, C.H., "MicroRNA, Expression in Lymphoma," Expert Opinoin on Biological Therapy, Sep. 2007, pp. 1363-1374, vol. 7, No. 9.

Lee, Y.S. et al., "MicroRNAs: Small but Potent Onogenes or Tumor Suppressors," Current Opinion in Investigational Drugs, Jun. 2006, pp. 560-564, vol. 7, No. 6.

Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.

Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.

O'Connell, R. et al., "Inositol Phosphatase SHIP1 is a Primary Target of miR-155," PNAS, Apr. 2009, pp. 7113-7118, vol. 106, No. 17.

Williams, C.S., "OncomiRs: The Discovery and Progress of MicroRNAs in Cancers," Molecular Cancer, Sep. 2007, pp. 259-269, vol. 6, No. 4.

Australian Office Action, Application No. 2006291165 dated Feb. 13, 2012.

Australian Office Action, Application No. 2007205234 dated Sep. 20, 2011.

Australian Office Action, Application No. 2007227423 dated Apr. 13, 2012.

Australian Office Action, Application No. 2007205257 dated Dec. 22, 2011.

Canadian Office Action, Application No. 2,635,616, dated Feb. 27, 20112.

Canadian Office Action, Application No. 2,617,581, dated Apr. 2, 2012.

Chinese Office Action, Application No. 200880119206390 dated May 3, 2012.

Communication Concerning Office Action Received from Japanese Patent Office dated Jan. 30, 2012, Japanese Patent Application No. 2008-531200.

EP Search Report, Application No. 11196256.9 dated Feb. 28, 2012.

EP Search Report, Application No. 11196190.0 dated Apr. 24, 2012.

EP Search Report, Application No. 11196265.0 dated Mar. 5, 2012.

EP Search Report, Application No. 11196253.6 dated Apr. 24, 2012.

EP Search Report, Application No. 11196250.2 dated Apr. 24, 2012.

EP Search Report, Application No. 11196262.7 dated Feb. 28, 2012

EP Search Report, Application No. 11196264-3 dated Feb. 28, 2012.
EP Search Report, Application No. 11196254.4 dated Feb. 28, 2012.
EP Search Report, Application No. 11196261.9 dated Feb. 28, 2012.
European Communication Pursuant to Article 94(3) EPC, Application No. 08767439.6, dated Feb. 12, 2011.
European Communication Pursuant to Article 94(3) EPC, Application No. 07717903.4, dated Apr. 25, 2012.
European Communication Pursuant to Article 94(3) EPC, Application No. 06800599.0 dated Nov. 25, 2011.
European Communication Pursuant to Article 94(3) EPC, Application No. 08799295.4, dated Nov. 18, 2011.
European Communication Pursuant to Article 94(3) EPC, Application No. 07867402.5, dated Apr. 10, 2012.
European Communication Pursuant to Article 94(3)EPC, Application No. 06814375.9 dated Oct. 14, 2011.
European Search Report, Application No. 08770974.4, dated Oct. 21, 2011.
Japanese Office Action dated Jan. 4, 2012, Japanese Patent Application No. 2008-5251070.
Japanese Office Action date Feb. 22, 2012, Japanese Patent Application No. 2008-549549.
Japanese Office Action date Feb. 24, 2012, Japanese Patent Application No. 2008-549532.
Japanese Office Action date Feb. 24, 2012, Japanese Patent Application No. 2008-549555.
PCT International Search Report and the Written Opinion, PCT/US2012/020911 filed Jan. 11, 2012, date Apr. 25, 2012
PCT Invitation to Pay Additional Fees, PCT/US2012/028016 filed Mar. 7, 2012, date May 29, 2012
Aiba, M. "Pathology of the Breast Carcinoma from the Viewpoint of the Proliferative Activity and Grade of Malignancy," JP J Cancer Clin, 2000, pp. 475-181, vol. 46, No. 5.
Braun et al., "p53-Responsive MicroRNAs 192 and 215 are Capable of Inducing Cell Cycle Arrest," Cancer Research, 2008, pp. 10094-10104, vol. 68.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.

Jazbutyte, V. et al., "MicroNRA-21: From Cancer to Cardiovascular Disease," Current Drug Targets, Abstract, 2010, pp. 926-935, vol. 11.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Okada, H. et al., "MicroRNAs in Immune Regulation—Opportunities for Cancer Immunotherapy," The International Journal of Biochemistry & Cell Biology, 2010, pp. 1256-1261, vol. 42.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Vassilev et al., "In Vivo Activation of the p53 Pathway by Small-Molecule Antagonists of MDM2," Science, 2004, pp. 844-848, vol. 303.
Watson, D.I. et al., "MicroRNA Expression Profiles in Barrett's Oesophagus," RACS Annual Scientific Congress, 2007, pp. A45, vol. 77.
Wiemer et al., "The Role of MicroRNAs in Cancer: No Small Matter," European Journal of Cancer, Jun. 12, 2007, vol. 43, No. 10, pp. 1529-1544.
Xi, Y. et al., "Prognostic Values of MicroRNAs in Colorectal Cancer," Biomarker Insights, Jan. 2006, pp. 113-121, vol. 1.
Zhao et al., "p53 Mediates the Negative Regulation of MDM2 by Orphan Receptor TR3," The EMBO Journal, 2006, pp. 5703-5715, vol. 25.

* cited by examiner

US 8,389,210 B2

MICRORNA EXPRESSION ABNORMALITIES IN PANCREATIC ENDOCRINE AND ACINAR TUMORS

CROSS-REFERENCE TO RELATED APPLICATIONS

This application claims the benefit of U.S. application Ser. No. 12/160,064, filed Jul. 3, 2008, which claims priority to PCT/US2007/000024, filed Jan. 3, 2007, which is a non-provisional application of Ser. No. 60/756,502 filed Jan. 5, 2006, the entire disclosures of which are expressly incorporated herein by reference.

GOVERNMENT SUPPORT

The invention was supported, in whole or in part, by Program Project Grants P01CA76259 and P01CA81534 from the National Cancer Institute. The Government has certain rights in the invention.

SEQUENCE LISTING

The Sequence Listing, filed electronically and identified as 604__51655_SEQ_LIST_OSURF-06139-2, was created on Feb. 9, 2010, is 92 kb in size and is hereby incorporated by reference. The electronically filed Sequence Listing is identical to that filed in the U.S. national stage application, U.S. Ser. No. 12/160,064 (filed Jul. 3, 2008), of which the instant application is a divisional.

BACKGROUND OF THE INVENTION

Pancreatic cancers can be classified according to where in the pancreas the cancer is found or according to the type of cell the cancer has originated from. Pancreatic cancer can occur in the head, body or tail of the pancreas and symptoms can vary depending on where in the pancreas the tumor is located. 70-80% of pancreatic cancers occur in the head of the pancreas. The majority of cancers of the pancreas are exocrine in type, and greater than 90% of these exocrine pancreatic cancers are adenocarcinomas. Nearly all of these are ductal adenocarcinomas, wherein the cancer occurs in the cells lining the ducts of the pancreas. In addition, there are rarer types of exocrine pancreatic cancer, such as cystic tumors, cancer of the acinar cells and sarcomas. Cystic tumors are tumors that cause a cyst or fluid-filled sac in the pancreas. Sarcomas, a cancer of the connective tissue holding together the cells of the pancreas, are rare and most often occur in children.

In addition to exocrine cancers, endocrine cancers of the pancreas can occur. The endocrine cancers can be named by reference to the hormone that they produce, e.g., gastrinomas (which produce gastrin), insulinomas (which produce insulin), somatostatinomas (which produce somatostatin), VIPomas (which produce VIP) and glucagonomas (which produce glucagon). In addition, lymphomas of the pancreas can occur, although they are rare.

Pancreatic endocrine tumors (PET) may occur either sporadically or as part of multiple endocrine neoplasia type 1 (MEN1) syndrome (Kloppel, G., et al., *Ann. N.Y. Acad. Sci.* 1014:13-27 (2004)). These neoplasms are clinically classified as functioning (F-PET) or nonfunctioning (NF-PET), according to the presence of symptoms due to hormone hypersecretion. F-PETs are mainly represented by insulinomas. At diagnosis, metastatic disease is observed in only 10% of insulinomas but in up to 60% of NF-PETs, and most PET-related deaths are caused by liver metastasis (Kloppel, G., et al., *Ann. N.Y. Acad. Sci.* 1014:13-27 (2004)). The malignant potential among PETs varies greatly and cannot be predicted on the basis of histological appearance. In fact, the vast majority of PETs are well-differentiated endocrine tumors (WDET) and are defined as well-differentiated endocrine carcinomas (WDEC) only when invasion or metastases are identified (Kloppel, G., et al., *Ann. N.Y. Acad. Sci.* 1014:13-27 (2004)).

Pancreatic acinar cell carcinoma (PACC) is an extremely rare tumor type distinct from ductal adenocarcinoma and PET, although some overlap with PET is observed by both the expression of neuroendocrine markers in one third of the cases and the existence of mixed acinar-endocrine carcinomas (Ohike, N., et al., *Virchows Arch.* 445:231-35 (2004)). PACC is always malignant with a median survival of 18 months, which lies between that of pancreatic ductal adenocarcinoma and endocrine neoplasms (6 months and 40 months, respectively) (Holen, K. D., et al., *J. Clin. Oncol.* 20:4673-78 (2002)).

Little is known about the molecular pathogenesis of PETs (Kloppel, G., et al., *Ann. N.Y. Acad. Sci.* 1014:13-27 (2004)). Inactivation of MEN1 gene is the most frequent genetic event identified in sporadic PET, while mutations in genes typically involved in pancreatic adenocarcinoma are uncommon (Perren, A., et al., *Ann. N.Y. Acad. Sci.* 1014:199-208 (2004)). Even less is known regarding the molecular anomalies of PACC (Abraham, S. C., et al., *Am. J. Pathol.* 160:953-62 (2002)). No gene expression profile data is available for PACC and our understanding of gene expression changes that occur in PET is still at an initial phase (Hansel, D. E., et al., *Clin. Cancer Res.* 10:6152-58 (2004)). MicroRNAs are small (20-24 nucleotides) noncoding RNA gene products that serve critical roles in many biological processes, such as cell proliferation, apoptosis and developmental timing. To perform these functions, microRNAs negatively regulate the stability and/or translational efficiency of their target mRNAs (Ambros, V., *Nature* 431:350-55 (2004)). Currently, 313 unique mature human microRNAs are known, 223 of which have been experimentally verified in humans (www.microrna.sanger.ac.uk). Recent studies suggest that aberrant expression of particular miRNAs may be involved in human diseases, such as neurological disorders (Ishizuka, A., et al., *Genes Dev.* 16:2497-2508 (2002)) and cancer. In particular, misexpression of miR-16-1 and/or miR-15a has been found in human chronic lymphocytic leukemias (CLL) (Calin, G. A., et al., *Proc. Natl. Acad. Sci. U.S.A.* 99:15524-15529 (2002)). Aberrant expression of microRNAs has been linked to cancers and diagnostic/prognostic characteristics of specific cancer types can be distinguished based on their microRNA profiles (Caldas, C., and J. D. Brenton, *Nature Med.* 11:712-14 (2005); Croce, C. M., and G. A. Calin, *Cell* 122:6-7 (2005)). Functional studies also have linked aberrant microRNA expression to carcinogenesis (Chan, J. A., et al., *Cancer Res.* 65:6029-33 (2005); Cheng, A. M., et al., *Nucleic Acids Res.* 33:1290-97 (2005); He, L., et al., *Nature* 435:828-33 (2005); and Johnson, S. M., et al., *Cell* 120:635-47 (2005)).

The development and use of microarrays containing all known human microRNAs has permitted a simultaneous analysis of the expression of every miRNA in a sample (Liu, C. G., et al., *Proc Natl. Acad. Sci. U.S.A.* 101:9740-9744 (2004)). These microRNA microarrays have not only been used to confirm that miR-16-1 is deregulated in human CLL cells, but also to generate miRNA expression signatures that are associated with well-defined clinicopathological features of human CLL (Calin, G. A., et al., *Proc. Natl. Acad. Sci. U.S.A.* 101:1175-11760 (2004)).

Identification of microRNAs that are differentially-expressed in pancreatic cancer cells may help pinpoint specific miRNAs that are involved in pancreatic cancer (e.g., pancreatic endocrine tumors, acinar carcinomas). Furthermore, the identification of putative targets of these miRNAs may help to unravel their pathogenic role. The present invention provides novel methods and compositions for the diagnosis, prognosis and treatment of pancreatic cancer.

SUMMARY OF THE INVENTION

The present invention is based, in part, on the identification of specific miRNAs associated with altered expression levels in pancreatic cancer cells.

Accordingly, the invention encompasses methods of diagnosing whether a subject has, or is at risk for developing, pancreatic cancer. According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in the control sample, is indicative of the subject either having, or being at risk for developing, pancreatic cancer.

In one embodiment, the level of the at least one miR gene product in the test sample is greater than the level of the corresponding miR gene product in the control sample. In another embodiment, the at least one miR gene product is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In yet another embodiment, the at least one miR gene product is selected from the group consisting of miR-103, miR-107 and a combination thereof. In still another embodiment, the at least one miR gene product is selected from the group consisting of miR-23a, miR-26b, miR-192, miR-342 and a combination thereof.

In one embodiment, the level of the at least one miR gene product in the test sample is less than the level of the corresponding miR gene product in the control sample. In another embodiment, the at least one miR gene product is selected from the group consisting of miR-326, miR-155, miR-339, miR-34c, miR-345, miR-152, miR-372, miR-128a and a combination thereof. In yet another embodiment, the at least one miR gene product is miR-155.

In one embodiment, the at least one miR gene product is selected from the group consisting of miR-103, is miR-107, miR-155 and a combination thereof. In another embodiment, the at least one miR gene product is miR-103, which is upregulated in the test sample, as compared to the control sample. In yet another embodiment, the at least one miR gene product is miR-107, which is upregulated in the test sample, as compared to the control sample. In still another embodiment, the at least one miR gene product is miR-155, which is downregulated in the test sample, as compared to the control sample. In a particular embodiment, all three of these miRs (miR-103, miR-107 and miR-155) are compared to the corresponding miRs in the control sample.

In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. In still another embodiment, the diagnostic method can be used to diagnose any type of pancreatic cancer.

In one embodiment, the invention is a method of diagnosing whether a subject has, or is at risk for developing, pancreatic acinar cell carcinoma (PACC). In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, PACC. In one embodiment, the level of the at least one miR gene product in the test sample is greater than the level of the corresponding miR gene product in the control sample. In another embodiment, the at least one miR gene product is selected from the group consisting of miR-103-2, miR-25, miR-200c, miR-335, miR-21, miR-103-1, miR-92-1, miR-181b-2, miR-191, miR-93, miR-26a-1, miR-17, miR-20, miR-107, miR-26b, miR-215, miR-92-2, miR-192, miR-342, miR-100, miR-3p21-v, miR-106a, miR-15a, miR-23a, miR-181b-1, miR-128b, miR-106b, miR-194-1, miR-219-1, miR-242 and a combination thereof. In yet another embodiment, the level of the at least one miR gene product in the test sample is less than the level of the corresponding miR gene product in the control sample. In still another embodiment, the at least one miR gene product is selected from the group consisting of miR-218-2, miR-339, miR-326, miR-34c, miR-152, miR-138-2, miR-128a and a combination thereof.

In one embodiment, the invention is a method of diagnosing the type of pancreatic cancer that a subject has. In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the type of pancreatic cancer.

In one embodiment, the type of pancreatic cancer that is diagnosed is selected from the group consisting of a pancreatic endocrine tumor (PET) and a pancreatic acinar cell carcinoma (PACC). In another embodiment, the level of the at least one miR gene product in the test sample is greater than the level of the corresponding miR gene product in the control sample. In another embodiment, the type of pancreatic cancer is a pancreatic endocrine tumor (PET) and the at least one miR gene product is selected from the group consisting of miR-125a, miR-99a, miR-99b, miR-125b-1, miR-342, miR-130a, miR-100, miR-132, miR-129-2, miR-125b-2 and a combination thereof. In yet another embodiment, the level of the at least one miR gene product in the test sample is less than the level of the corresponding miR gene product in the control sample. In still another embodiment, the type of pancreatic cancer is a pancreatic acinar cell carcinoma (PACC) and the at least one miR gene product is selected from the group consisting of miR-125a, miR-99a, miR-99b, miR-125b-1, miR-342, miR-130a, miR-100, miR-132, miR-129-2, miR-125b-2 and a combination thereof.

In one embodiment, the type of pancreatic cancer that is diagnosed is selected from the group consisting of a well-differentiated endocrine carcinoma (WDEC) and a pancreatic acinar cell carcinoma (PACC). In another embodiment, the level of the at least one miR gene product in the test sample is greater than the level of the corresponding miR gene product in the control sample. In yet another embodiment, the type of pancreatic cancer is a well-differentiated endocrine carcinoma (WDEC) and the at least one miR gene product is selected from the group consisting of miR-125a, miR-99a, miR-132 and a combination thereof. In another embodiment, the level of the at least one miR gene product in the test sample is less than the level of the corresponding miR gene product in the control sample. In still another embodiment, the type of pancreatic cancer is a well-differentiated endocrine carcinoma (WDEC) and the at least one miR gene product is miR-148a.

In one embodiment, the type of pancreatic cancer that is diagnosed is selected from the group consisting of an insulinoma and a non-functioning pancreatic endocrine tumor (NF-PET). In one embodiment, the level of the at least one miR gene product in the test sample is greater than the level of the corresponding miR gene product in the control sample. In another embodiment, the type of pancreatic cancer is an insulinoma and the at least one miR gene product is selected from the group consisting of miR-204, miR-203, miR-211 and a combination thereof.

In one embodiment, the invention is a method of determining the prognosis of a subject with pancreatic cancer. In this method, the level of at least one miR gene product, which is associated with an adverse prognosis in pancreatic cancer, is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of an adverse prognosis.

In one embodiment, the level of the at least one miR gene product in the test sample is greater than the level of the corresponding miR gene product in a control sample. In another embodiment, the at least one miR gene product that is measured is miR-21. In yet another embodiment, the pancreatic cancer is associated with metastasis and/or a high proliferation index.

In one embodiment, the invention is a method of determining whether a pancreatic cancer in a subject is metastatic. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of metastasis. In one embodiment, the level of the at least one miR gene product in the test sample is greater than the level of the corresponding miR gene product in the control sample. In another embodiment, the at least one miR gene product is miR-21.

In one embodiment, the invention is a method of determining whether a pancreatic cancer in a subject has a high proliferation index. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of a high proliferation index. In one embodiment, the level of the at least one miR gene product in the test sample is greater than the level of the corresponding miR gene product in the control sample. In another embodiment, the at least one miR gene product is miR-21.

In one embodiment, the invention is a method of determining the prognosis of a subject with pancreatic cancer. In this method, the level of PDCD4 is measured in a test sample (e.g., a pancreatic cancer sample) from the subject. An alteration (e.g., an increase, a decrease) in the level of PDCD4 in the test sample, relative to the level of PDCD4 in a control sample, is indicative of an adverse prognosis. In one embodiment, the level of PDCD4 in the test sample is less than the level of PDCD4 in the control sample. In another embodiment, the pancreatic cancer is associated with metastasis and/or a high proliferation index.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, pancreatic cancer. In one embodiment, the signal of at least one miRNA is upregulated, relative to the signal generated from the control sample. In another embodiment, the signal of at least one miRNA is downregulated, relative to the signal generated from the control sample. In a particular embodiment, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR- 133a-1, miR-200c, miR-194-1, miR-210, miR-181c, miR-192, miR-220, miR-213, miR-323, miR-375, miR-326, miR-155, miR-339, miR-34c, miR-345, miR-152, miR-372, miR-128a and a combination thereof.

The invention also provides methods of diagnosing whether a subject has, or is at risk for developing, a pancreatic cancer with an adverse prognosis. In this method, the level of at least one miR gene product, which is associated with an adverse prognosis in pancreatic cancer, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a pancreatic cancer with an adverse prognosis. In one embodiment, an alteration in the signal of miR-21 is indicative of the subject either having, or being at risk for developing, a pancreatic cancer with an adverse prognosis.

The invention also encompasses methods of treating pancreatic cancer in a subject, wherein at least one miR gene product is deregulated (e.g., downregulated, upregulated) in the cancer cells of the subject. When at least one isolated miR gene product is downregulated in the pancreatic cancer cells, the method comprises administering an effective amount of an isolated miR gene product, or an isolated variant or biologically-active fragment thereof, such that proliferation of cancer cells in the subject is inhibited. In one embodiment, the at least one isolated miR gene product that is administered to the subject is selected from the group consisting of miR-326, miR-155, miR-339, miR-34c, miR-345, miR-152, miR-372, miR-128a and a combination thereof (or an isolated variant or biologically-active fragment of one or more of these miRs). When at least one isolated miR gene product is upregulated in the cancer cells, the method comprises administering to the subject an effective amount of at least one compound for inhibiting expression of the at least one miR gene product, such that proliferation of pancreatic cancer cells is inhibited. In one embodiment, the compound for inhibiting expression of the at least one miR gene product inhibits a miR gene product selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

In a related embodiment, the methods of treating pancreatic cancer in a subject additionally comprise the step of first determining the amount of at least one miR gene product in pancreatic cancer cells from the subject, and comparing that level of the miR gene product to the level of a corresponding miR gene product in control cells. If expression of the miR gene product is deregulated (e.g., downregulated, upregulated) in pancreatic cancer cells, the methods further comprise altering the amount of the at least one miR gene product expressed in the pancreatic cancer cells. In one embodiment, the amount of the miR gene product expressed in the cancer cells is less than the amount of the miR gene product expressed in control cells, and an effective amount of the miR gene product, or an isolated variant or biologically-active fragment thereof, is administered to the subject. In another embodiment, the amount of the miR gene product expressed in the cancer cells is greater than the amount of the miR gene product expressed in control cells, and an effective amount of at least one compound for inhibiting expression of the at least one miR gene is administered to the subject. Suitable miRs and compounds that inhibit expression of miR genes include, for example, those described herein.

The invention further provides pharmaceutical compositions for treating pancreatic cancer. In one embodiment, the pharmaceutical compositions comprise at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in pancreatic cancer cells relative to suitable control cells (i.e., it is downregulated). In a certain embodiment, the isolated miR gene product is selected from the group consisting of miR-326, miR-155, miR-339, miR-34c, miR-345, miR-152, miR-372, miR-128a and a combination thereof.

In another embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in pancreatic cancer cells than control cells (i.e., it is upregulated). In certain embodiments, the miR expression-inhibition compound is specific for one or more miR gene products selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

The invention also encompasses methods of identifying an anti-pancreatic cancer agent, comprising providing a test agent to a cell and measuring the level of at least one miR gene product in the cell. In one embodiment, the method comprises providing a test agent to a cell and measuring the level of at least one miR gene product associated with decreased expression levels in pancreatic cancer cells. An increase in the level of the miR gene product in the cell, relative to a suitable control cell, is indicative of the test agent being an anti-pancreatic cancer agent. In a particular embodiment, the at least one miR gene product associated with decreased expression levels in pancreatic cancer cells is selected from the group consisting of miR-326, miR-155, miR-339, miR-34c, miR-345, miR-152, miR-372, miR-128a and a combination thereof.

In other embodiments, the method comprises providing a test agent to a cell and measuring the level of at least one miR gene product associated with increased expression levels in pancreatic cancer cells. A decrease in the level of the miR gene product associated with increased expression levels in pancreatic cancer in the cell, relative to a suitable control cell, is indicative of the test agent being an anti-pancreatic cancer agent. In a particular embodiment, the at least one miR gene product associated with increased expression levels in pancreatic cancer cells is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figures 1A, 1B, 1C, 1D, 1E:
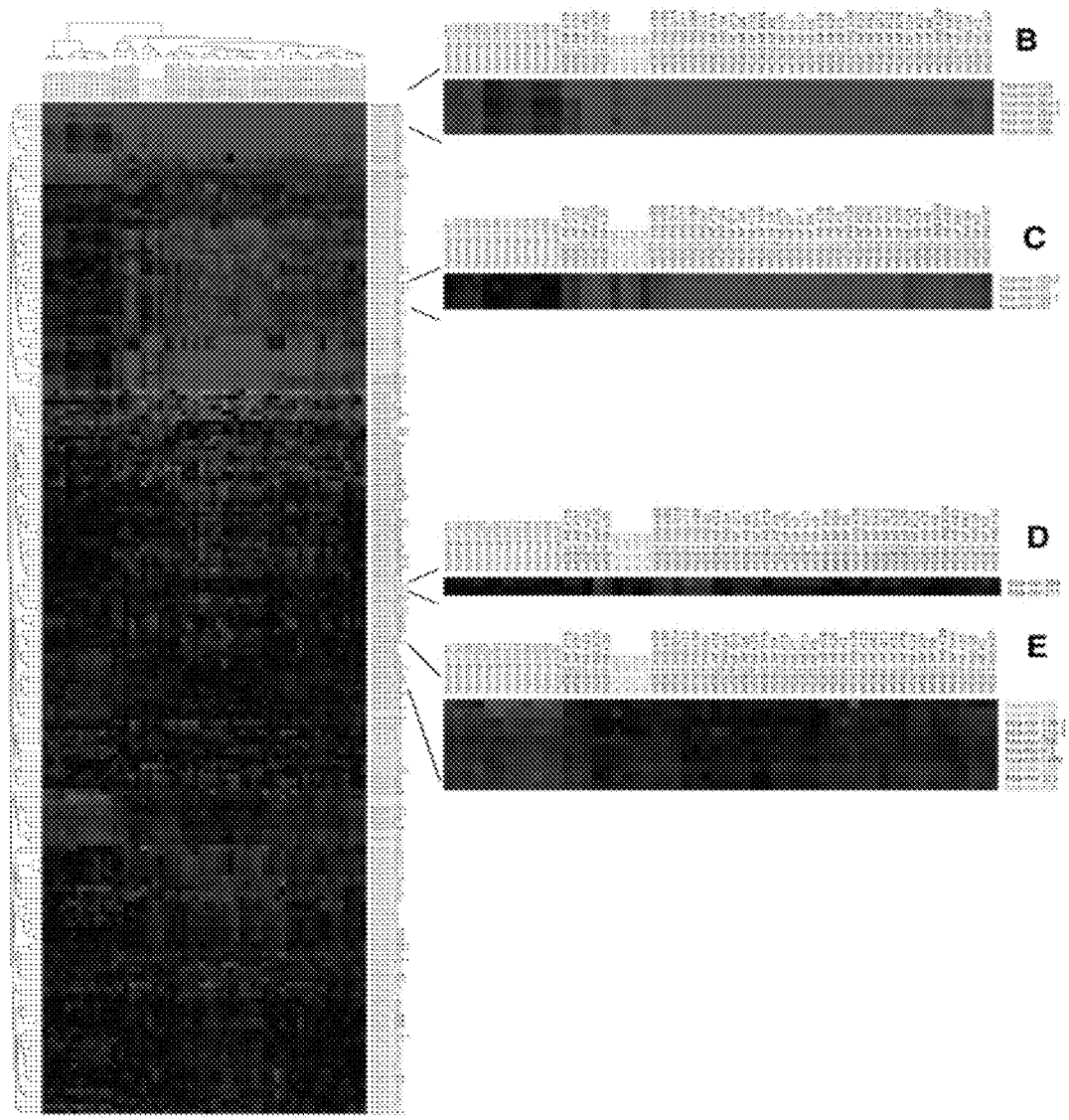
FIG. 1A depicts an miRNA expression unsupervised hierarchical cluster view of 12 normal pancreas (Normal) and 44 pancreatic tumors, including 22 well-differentiated pancreatic endocrine tumors (WDET), 18 well-differentiated pancreatic endocrine carcinomas (WDEC) and 4 pancreatic acinar cell carcinomas (ACC) (listed at top). WDET samples included 11 insulinomas (INS) and 1 Non-functioning PET (NF); WDEC samples included 1 INS and 17 NF-PET. The analysis was performed using the aggregate values of replicate spots obtained applying median polish algorithm and selecting the first 200 probes with the higher interquartile range, which contained the mature microRNA sequences. Notably, PACC samples fell in a unique cluster that was part of the wider cluster including all PETs, while there was no distinctive pattern between insulinomas and NF-PET. As is depicted, a common microRNA expression pattern distinguishes pancreatic endocrine and acinar tumors from normal pancreas.
FIG. 1B depicts particular microRNAs that are found to be upregulated in PET versus Normal tissue (upregulated microRNAs are listed in red).
FIG. 1C depicts particular microRNAs that are found to be upregulated in PET versus Normal tissue (upregulated microRNAs are listed in red).
FIG. 1D depicts two microRNAs that are upregulated in insulinoma versus Non-functioning PET ((upregulated microRNAs are listed in blue).
FIG. 1E depicts particular microRNAs that are found to be downregulated in PET versus Normal tissue (downregulated microRNAs are listed in green).

The present invention is based, in part, on the identification of particular microRNAs having altered expression in pancreatic cancer cells relative to normal control cells, and on association of these microRNAs with particular diagnostic, prognostic and therapeutic features. As described herein:

i) a common pattern of microRNA expression distinguishes pancreatic tumor types from normal pancreas, and thereby implicates the involvement of particular microRNAs in pancreatic tumorigenesis;

ii) the expression of miR-103 and miR-107, associated with lack of expression of miR-155, discriminates pancreatic tumors from normal pancreas;

iii) at least 10 microRNAs distinguishes endocrine tumors from acinar tumors, and implicates particular microRNAs in endocrine differentiation and/or endocrine tumorigenesis;

iv) miR-204 is primarily expressed in insulinomas and correlates with immunohistochemical expression of insulin; and v) over-expression of miR-21 is strongly associated with both a high Ki67 proliferation index and the presence of liver metastasis.

These results imply that alteration in microRNA expression is related to endocrine and acinar neoplastic transformation and progression of malignancy. Accordingly, expression of particular microRNAs, as well as alterations of such microRNA expression, can be used in the diagnostic, prognostic and therapeutic methods described herein.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., E. coli RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, pancreatic cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, pancreatic cancer. In a preferred embodiment, the subject is a human who has, or is suspected of having, pancreatic cancer.

The pancreatic cancer can be any form of pancreatic cancer, for example, pancreatic cancers of differing histology (e.g., exocrine tumors, endocrine tumors, carcinomas, lymphomas). In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. Furthermore, as described herein, the pancreatic cancer may be associated with a particular prognosis (e.g., low survival rate, fast progression). Tables 1a and 1b depict the nucleotide sequences of particular precursor and mature human microRNAs.

TABLE 1a

Human microRNA Precursor Sequences.

| Precursor Name | Sequence (5' To 3')* | SEQ ID NO. |
|---|---|---|
| let-7a-1 | CACUGUGGG<u>AUGAGGUAGUAGGUUGUAUAGUU</u>UAGGGUCACACCCACCACUGGGAGAUAACUAUACAAUCUACUGUCUUUCCUAACGUG | 1 |

TABLE 1a-continued

Human microRNA Precursor Sequences.

| Precursor Name | Sequence (5' To 3')* | SEQ ID NO. |
|---|---|---|
| let-7a-2 | AGGUUGAGGUAGUAGGUUGUAUAGUUUAGAAUUACA UCAAGGGAGAUAACUGUACAGCCUCCUAGCUUUCCU | 2 |
| let-7a-3 | GGGUGAGGUAGUAGGUUGUAUAGUUUGGGGCUCUGC CCUGCUAUGGGAUAACUAUACAAUCUACUGUCUUUC CU | 3 |
| let-7a-4 | GUGACUGCAUGCUCCCAGGUUGAGGUAGUAGGUUGU AUAGUUUAGAAUUACACAAGGGAGAUAACUGUACAG CCUCCUAGCUUUCCUUGGGUCUUGCACUAAACAAC | 4 |
| let-7b | GGCGGGGUGAGGUAGUAGGUUGUGUGGUUUCAGGGC AGUGAUGUUGCCCCUCGGAAGAUAACUAUACAACCU ACUGCCUUCCCUG | 5 |
| let-7c | GCAUCCGGGUUGAGGUAGUAGGUUGUAUGGUUUAGA GUUACACCCUGGGAGUUAACUGUACAACCUUCUAGC UUUCCUUGGAGC | 6 |
| let-7d | CCUAGGAAGAGGUAGUAGGUUGCAUAGUUUUAGGGC AGGGAUUUUGCCCACAAGGAGGUAACUAUACGACCU GCUGCCUUUCUUAGG | 7 |
| let-7d-v1 | CUAGGAAGAGGUAGUAGUUUGCAUAGUUUUAGGGCA AAGAUUUUGCCCACAAGUAGUUAGCUAUACGACCUG CAGCCUUUUGUAG | 8 |
| let-7d-v2 | CUGGCUGAGGUAGUAGUUUGUGCUGUUGGUCGGGUU GUGACAUUGCCCGCUGUGGAGAUAACUGCGCAAGCU ACUGCCUUGCUAG | 9 |
| let-7e | CCCGGGCUGAGGUAGGAGGUUGUAUAGUUGAGGAGG ACACCCAAGGAGAUCACUAUACGGCCUCCUAGCUUUC CCAGG | 10 |
| let-7f-1 | UCAGAGUGAGGUAGUAGAUUGUAUAGUUGUGGGGUA GUGAUUUUACCCUGUUCAGGAGAUAACUAUACAAUC UAUUGCCUUCCCUGA | 11 |
| let-7f-2-1 | CUGUGGGAUGAGGUAGUAGAUUGUAUAGUUGUGGGG UAGUGAUUUUACCCUGUUCAGGAGAUAACUAUACAA UCUAUUGCCUUCCCUGA | 12 |
| let-7f-2-2 | CUGUGGGAUGAGGUAGUAGAUUGUAUAGUUUUAGGG UCAUACCCCAUCUUGGAGAUAACUAUACAGUCUACU GUCUUUCCCACGG | 13 |
| let-7g | UUGCCUGAUUCCAGGCUGAGGUAGUAGUUUGUACAG UUUGAGGGUCUAUGAUACCACCCGGUACAGGAGAUA ACUGUACAGGCCACUGCCUUGCCAGGAACAGCGCG | 14 |
| let-7i | CUGGCUGAGGUAGUAGUUUGUGCUGUUGGUCGGGUU GUGACAUUGCCCGCUGUGGAGAUAACUGCGCAAGCU ACUGCCUUGCUAG | 15 |
| miR-1b-1-1 | ACCUACUCAGAGUACAUACUUCUUUAUGUACCCAUA UGAACAUACAAUGCUAUGGAAUGUAAAGAAGUAUGU AUUUUUGGUAGGC | 16 |
| miR-1b-1-2 | CAGCUAACAACUUAGUAAUACCUACUCAGAGUACAU ACUUCUUUAUGUACCCAUAUGAACAUACAAUGCUAU GGAAUGUAAAGAAGUAUGUAUUUUUGGUAGGCAAUA | 17 |
| miR-1b-2 | GCCUGCUUGGGAAACAUACUUCUUUAUAUGCCCAUA UGGACCUGCUAAGCUAUGGAAUGUAAAGAAGUAUGU AUCUCAGGCCGGG | 18 |
| miR-1b | UGGGAAACAUACUUCUUUAUAUGCCCAUAUGGACCU GCUAAGCUAUGGAAUGUAAAGAAGUAUGUAUCUCA | 19 |
| miR-1d | ACCUACUCAGAGUACAUACUUCUUUAUGUACCCAUA UGAACAUACAAUGCUAUGGAAUGUAAAGAAGUAUGU AUUUUUGGUAGGC | 20 |

TABLE 1a-continued

Human microRNA Precursor Sequences.

| Precursor Name | Sequence (5' To 3')* | SEQ ID NO. |
|---|---|---|
| miR-7-1a | UGGAUGUUGGCCUAGUUCUGUGUGGAAGACUAGUGAUUUUGUUGUUUUUAGAUAACUAAAUCGACAACAAAUCACAGUCUGCCAUAUGGCACAGGCCAUGCCUCUACA | 21 |
| miR-7-1b | UUGGAUGUUGGCCUAGUUCUGUGUGGAAGACUAGUGAUUUUGUUGUUUUUAGAUAACUAAAUCGACAACAAAUCACAGUCUGCCAUAUGGCACAGGCCAUGCCUCUACAG | 22 |
| miR-7-2 | CUGGAUACAGAGUGGACCGGCUGGCCCCAUCUGGAAGACUAGUGAUUUUGUUGUUGUCUUACUGCGCUCAACAACAAAUCCCAGUCUACCUAAUGGUGCCAGCCAUCGCA | 23 |
| miR-7-3 | AGAUUAGAGUGGCUGUGGUCUAGUGCUGUGUGGAAGACUAGUGAUUUUGUUGUUCUGAUGUACUACGACAACAAGUCACAGCCGGCCUCAUAGCGCAGACUCCCUUCGAC | 24 |
| miR-9-1 | CGGGGUUGGUUGUUAUCUUUGGUUAUCUAGCUGUAUGAGUGGUGUGGAGUCUUCAUAAAGCUAGAUAACCGAAAGUAAAAAUAACCCCA | 25 |
| miR-9-2 | GGAAGCGAGUUGUUAUCUUUGGUUAUCUAGCUGUAUGAGUGUAUGGUCUUCAUAAAGCUAGAUAACCGAAAGUAAAAACUCCUUCA | 26 |
| miR-9-3 | GGAGGCCCGUUUCUCUCUUUGGUUAUCUAGCUGUAUGAGUGCCACAGAGCCGUCAUAAAGCUAGAUAACCGAAAGUAGAAAUGAUUCUCA | 27 |
| miR-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | 28 |
| miR-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | 29 |
| miR-15a-2 | GCGCGAAUGUGUGUUUAAAAAAAAUAAAACCUUGGAGUAAAGUAGCAGCACAUAAUGGUUUGUGGAUUUUGAAAAGGUGCAGGCCAUAUUGUGCUGCCUCAAAAAUAC | 30 |
| miR-15a | CCUUGGAGUAAAGUAGCAGCACAUAAUGGUUUGUGGAUUUUGAAAAGGUGCAGGCCAUAUUGUGCUGCCUCAAAAAUACAAGG | 31 |
| miR-15b-1 | CUGUAGCAGCACAUCAUGGUUUACAUGCUACAGUCAAGAUGCGAAUCAUUAUUUGCUGCUCUAG | 32 |
| miR-15b-2 | UUGAGGCCUUAAAGUACUGUAGCAGCACAUCAUGGUUUACAUGCUACAGUCAAGAUGCGAAUCAUUAUUUGCUGCUCUAGAAAUUUAAGGAAAUUCAU | 33 |
| miR-16-1 | GUCAGCAGUGCCUUAGCAGCACGUAAAUAUUGGCGUUAAGAUUCUAAAAUUAUCUCCAGUAUUAACUGUGCUGCUGAAGUAAGGUUGAC | 34 |
| miR-16-2 | GUUCCACUCUAGCAGCACGUAAAUAUUGGCGUAGUGAAAUAUAUAUUAAACACCAAUAUUACUGUGCUGCUUUAGUGUGAC | 35 |
| miR-16-13 | GCAGUGCCUUAGCAGCACGUAAAUAUUGGCGUUAAGAUUCUAAAAUUAUCUCCAGUAUUAACUGUGCUGCUGAAGUAAGGU | 36 |
| miR-17 | GUCAGAAUAAUGUCAAAGUGCUUACAGUGCAGGUAGUGAUAUGUGCAUCUACUGCAGUGAAGGCACUUGUAGCAUUAUGGUGAC | 37 |
| miR-18 | UGUUCUAAGGUGCAUCUAGUGCAGAUAGUGAAGUAGAUUAGCAUCUACUGCCCUAAGUGCUCCUUCUGGCA | 38 |

TABLE 1a-continued

Human microRNA Precursor Sequences.

| Precursor Name | Sequence (5' To 3')* | SEQ ID NO. |
|---|---|---|
| miR-18-13 | UUUUUGUUCUAAGGUGCAUCUAGUGCAGAUAGUGAAGUAGAUUAGCAUCUACUGCCCUAAGUGCUCCUUCUGGCAUAAGAA | 39 |
| miR-19a | GCAGUCCUCUGUUAGUUUUGCAUAGUUGCACUACAAGAAGAAUGUAGUUGUGCAAAUCUAUGCAAAACUGAUGGUGGCCUGC | 40 |
| miR-19a-13 | CAGUCCUCUGUUAGUUUUGCAUAGUUGCACUACAAGAAGAAUGUAGUUGUGCAAAUCUAUGCAAAACUGAUGUGGCCUG | 41 |
| miR-19b-1 | CACUGUUCUAUGGUUAGUUUUGCAGGUUUGCAUCCAGCUGUGUGAUAUUCUGCUGUGCAAAUCCAUGCAAAACUGACUGUGGUAGUG | 42 |
| miR-19b-2 | ACAUUGCUACUUACAAUUAGUUUUGCAGGUUUGCAUUUCAGCGUAUAUAUGUAUAUGUGGCUGUGCAAAUCCAUGCAAAACUGAUUGUGAUAAUGU | 43 |
| miR-19b-13 | UUCUAUGGUUAGUUUUGCAGGUUUGCAUCCAGCUGUGUGAUAUUCUGCUGUGCAAAUCCAUGCAAAACUGACUGUGGUAG | 44 |
| miR-19b-X | UUACAAUUAGUUUUGCAGGUUUGCAUUUCAGCGUAUAUAUGUAUAUGUGGCUGUGCAAAUCCAUGCAAAACUGAUUGUGAU | 45 |
| miR-20 (miR-20a) | GUAGCACUAAAGUGCUUAUAGUGCAGGUAGUGUUUAGUUAUCUACUGCAUUAUGAGCACUUAAAGUACUGC | 46 |
| miR-21 | UGUCGGGUAGCUUAUCAGACUGAUGUUGACUGUUGAAUCUCAUGGCAACACCAGUCGAUGGGCUGUCUGACA | 47 |
| miR-21-17 | ACCUUGUCGGGUAGCUUAUCAGACUGAUGUUGACUGUUGAAUCUCAUGGCAACACCAGUCGAUGGGCUGUCUGACAUUUUG | 48 |
| miR-22 | GGCUGAGCCGCAGUAGUUCUUCAGUGGCAAGCUUUAUGUCCUGACCCAGCUAAAGCUGCCAGUUGAAGAACUGUUGCCCUCUGCC | 49 |
| miR-23a | GGCCGGCUGGGGUUCCUGGGGAUGGGAUUUGCUUCCUGUCACAAAUCACAUUGCCAGGGAUUUCCAACCGACC | 50 |
| miR-23b | CUCAGGUGCUCUGGCUGCUUGGGUUCCUGGCAUGCUGAUUUGUGACUUAAGAUUAAAAUCACAUUGCCAGGGAUUACCACGCAACCACGACCUUGGC | 51 |
| miR-23-19 | CCACGGCCGGCUGGGGUUCCUGGGGAUGGGAUUUGCUUCCUGUCACAAAUCACAUUGCCAGGGAUUUCCAACCGACCCUGA | 52 |
| miR-24-1 | CUCCGGUGCCUACUGAGCUGAUAUCAGUUCUCAUUUUACACACUGGCUCAGUUCAGCAGGAACAGGAG | 53 |
| miR-24-2 | CUCUGCCUCCCGUGCCUACUGAGCUGAAACACAGUUGGUUUGUGUACAUGGCUCAGUUCAGCAGGAACAGGG | 54 |
| miR-24-19 | CCCUGGGCUCUGCCUCCCGUGCCUACUGAGCUGAAACACAGUUGGUUUGUGUACAUGGCUCAGUUCAGCAGGAACAGGGG | 55 |
| miR-24-9 | CCCUCCGGUGCCUACUGAGCUGAUAUCAGUUCUCAUUUUACACACUGGCUCAGUUCAGCAGGAACAGCAUC | 56 |
| miR-25 | GGCCAGUGUUGAGAGGCGGAGACUUGGGCAAUUGCUGGACGCUGCCCUGGGCAUUGCACUUGUCUCGGUCUGACAGUGCCGGCC | 57 |
| miR-26a | AGGCCGUGGCCUCGUUCAAGUAAUCCAGGAUAGGCUGUGCAGGUCCCAAUGGGCCUAUCUUGGUUACUUGCACGGGGACGCGGGCCU | 58 |

TABLE 1a-continued

Human microRNA Precursor Sequences.

| Precursor Name | Sequence (5' To 3')* | SEQ ID NO. |
|---|---|---|
| miR-26a-1 | GUGGCCUCGUUCAAGUAAUCCAGGAUAGGCUGUGCA GGUCCCAAUGGGCCUAUUCUUGGUUACUUGCACGGG GACGC | 59 |
| miR-26a-2 | GGCUGUGGCUGGAUUCAAGUAAUCCAGGAUAGGCUG UUUCCAUCUGUGAGGCCUAUUCUUGAUUACUUGUUU CUGGAGGCAGCU | 60 |
| miR-26b | CCGGGACCCAGUUCAAGUAAUUCAGGAUAGGUUGUG UGCUGUCCAGCCUGUUCUCCAUUACUUGGCUCGGGG ACCGG | 61 |
| miR-27a | CUGAGGAGCAGGGCUUAGCUGCUUGUGAGCAGGGUC CACACCAAGUCGUGUUCACAGUGGCUAAGUUCCGCCC CCCAG | 62 |
| miR-27b-1 | AGGUGCAGAGCUUAGCUGAUUGGUGAACAGUGAUUG GUUUCCGCUUUGUUCACAGUGGCUAAGUUCUGCACC U | 63 |
| miR-27b-2 | ACCUCUCUAACAAGGUGCAGAGCUUAGCUGAUUGGU GAACAGUGAUUGGUUUCCGCUUUGUUCACAGUGGCU AAGUUCUGCACCUGAAGAGAAGGUG | 64 |
| miR-27-19 | CCUGAGGAGCAGGGCUUAGCUGCUUGUGAGCAGGGU CCACACCAAGUCGUGUUCACAGUGGCUAAGUUCCGCC CCCCAGG | 65 |
| miR-28 | GGUCCUUGCCCUCAAGGAGCUCACAGUCUAUUGAGU UACCUUUCUGACUUUCCCACUAGAUUGUGAGCUCCU GGAGGGCAGGCACU | 66 |
| miR-29a-2 | CCUUCUGUGACCCCUUAGAGGAUGACUGAUUUCUUU UGGUGUUCAGAGUCAAUAUAAUUUUCUAGCACCAUC UGAAAUCGGUUAUAAUGAUUGGGGAAGAGCACCAUG | 67 |
| miR-29a | AUGACUGAUUUCUUUUGGUGUUCAGAGUCAAUAUAA UUUUCUAGCACCAUCUGAAAUCGGUUAU | 68 |
| miR-29b-1 | CUUCAGGAAGCUGGUUUCAUAUGGUGGUUUAGAUUU AAAUAGUGAUUGUCUAGCACCAUUUGAAAUCAGUGU UCUUGGGGG | 69 |
| miR-29b-2 | CUUCUGGAAGCUGGUUUCACAUGGUGGCUUAGAUUU UUCCAUCUUUGUAUCUAGCACCAUUUGAAAUCAGUG UUUUAGGAG | 70 |
| miR-29c | ACCACUGGCCCAUCUCUUACACAGGCUGACCGAUUUC UCCUGGUGUUCAGAGUCUGUUUUUGUCUAGCACCAU UUGAAAUCGGUUAUGAUGUAGGGGGAAAAGCAGCAG C | 71 |
| miR-30a | GCGACUGUAAACAUCCUCGACUGGAAGCUGUGAAGC CACAGAUGGGCUUUCAGUCGGAUGUUUGCAGCUGC | 72 |
| miR-30b-1 | AUGUAAACAUCCUACACUCAGCUGUAAUACAUGGAU UGGCUGGGAGGUGGAUGUUUACGU | 73 |
| miR-30b-2 | ACCAAGUUUCAGUUCAUGUAAACAUCCUACACUCAG CUGUAAUACAUGGAUUGGCUGGGAGGUGGAUGUUUA CUUCAGCUGACUUGGA | 74 |
| miR-30c | AGAUACUGUAAACAUCCUACACUCUCAGCUGUGGAA AGUAAGAAAGCUGGGAGAAGGCUGUUUACUCUUUCU | 75 |
| miR-30d | GUUGUUGUAAACAUCCCCGACUGGAAGCUGUAAGAC ACAGCUAAGCUUUCAGUCAGAUGUUUGCUGCUAC | 76 |
| miR-30e | CUGUAAACAUCCUUGACUGGAAGCUGUAAGGUGUUC AGAGGAGCUUUCAGUCGGAUGUUUACAG | 77 |
| miR-31 | GGAGAGGAGGCAAGAUGCUGGCAUAGCUGUUGAACU GGGAACCUGCUAUGCCAACAUAUUGCCAUCUUUCC | 78 |

TABLE 1a-continued

Human microRNA Precursor Sequences.

| Precursor Name | Sequence (5' To 3')* | SEQ ID NO. |
|---|---|---|
| miR-32 | GGAGAUAUUGCACAUUACUAAGUUGCAUGUUGUCAC GGCCUCAAUGCAAUUUAGUGUGUGUGAUAUUUUC | 79 |
| miR-33b | GGGGGCCGAGAGAGGCGGGCGGCCCCGCGGUGCAUU GCUGUUGCAUUGCACGUGUGUGAGGCGGGUGCAGUG CCUCGGCAGUGCAGCCCGGAGCCGGCCCCUGGCACCA C | 80 |
| miR-33b-2 | ACCAAGUUUCAGUUCAUGUAAACAUCCUACACUCAG CUGUAAUACAUGGAUUGGCUGGGAGGUGGAUGUUUA CUUCAGCUGACUUGGA | 81 |
| miR-33 | CUGUGGUGCAUUGUAGUUGCAUUGCAUGUUCUGGUG GUACCCAUGCAAUGUUUCCACAGUGCAUCACAG | 82 |
| miR-34-a | GGCCAGCUGUGAGUGUUUCUUUGGCAGUGUCUUAGC UGGUUGUUGUGAGCAAUAGUAAGGAAGCAAUCAGCA AGUAUACUGCCCUAGAAGUGCUGCACGUUGUGGGGC CC | 83 |
| miR-34-b | GUGCUCGGUUUGUAGGCAGUGUCAUUAGCUGAUUGU ACUGUGGUGGUUUACAAUCACUAACUCCACUGCCAUC AAAACAAGGCAC | 84 |
| miR-34-c | AGUCUAGUUACUAGGCAGUGUAGUUAGCUGAUUGCU AAUAGUACCAAUCACUAACCACACGGCCAGGUAAAA AGAUU | 85 |
| miR-91-13 | UCAGAAUAAUGUCAAAGUGCUUACAGUGCAGGUAGU GAUAUGUGCAUCUACUGCAGUGAAGGCACUUGUAGC AUUAUGGUGA | 86 |
| miR-92-1 | CUUUCUACACAGGUUGGGAUCGGUUGCAAUGCUGUG UUUCUGUAUGGUAUUGCACUUGUCCCGGCCUGUUGA GUUUGG | 87 |
| miR-92-2 | UCAUCCCUGGGUGGGGAUUUGUUGCAUUACUUGUGU UCUAUAUAAAGUAUUGCACUUGUCCCGGCCUGUGGA AGA | 88 |
| miR-93-1 (miR-93-2) | CUGGGGGCUCCAAAGUGCUGUUCGUGCAGGUAGUGU GAUUACCCAACCUACUGCUGAGCUAGCACUUCCCGAG CCCCCGG | 89 |
| miR-95-4 | AACACAGUGGGCACUCAAUAAAUGUCUGUUGAAUUG AAAUGCGUUACAUUCAACGGGUAUUUAUUGAGCACC CACUCUGUG | 90 |
| miR-96-7 | UGGCCGAUUUUGGCACUAGCACAUUUUUGCUUGUGU CUCUCCGCUCUGAGCAAUCAUGUGCAGUGCCAAUAU GGGAAA | 91 |
| miR-97-6 (miR-30*) | GUGAGCGACUGUAAACAUCCUCGACUGGAAGCUGUG AAGCCACAGAUGGGCUUUCAGUCGGAUGUUUGCAGC UGCCUACU | 92 |
| miR-98 | GUGAGGUAGUAAGUUGUAUUGUUGUGGGGUAGGGAU AUUAGGCCCCAAUUAGAAGAUAACUAUACAACUUAC UACUUUCC | 93 |
| miR-99b | GGCACCCACCCGUAGAACCGACCUUGCGGGGCCUUCG CCGCACACAAGCUCGUGUCUGUGGGUCCGUGUC | 94 |
| miR-99a | CCCAUUGGCAUAAACCCGUAGAUCCGAUCUUGUGGU GAAGUGGACCGCACAAGCUCGCUUCUAUGGGUCUGU GUCAGUGUG | 95 |
| miR-100-1/2 | AAGAGAGAAGAUAUUGAGGCCUGUUGCCACAAACCC GUAGAUCCGAACUUGUGGUAUUAGUCCGCACAAGCU UGUAUCUAUAGGUAUGUGUCUGUUAGGCAAUCUCAC | 96 |
| miR-100-11 | CCUGUUGCCACAAACCCGUAGAUCCGAACUUGUGG AUUAGUCCGCACAAGCUUGUAUCUAUAGGUAUGUGU CUGUUAGG | 97 |

TABLE 1a-continued

Human microRNA Precursor Sequences.

| Precursor Name | Sequence (5' To 3')* | SEQ ID NO. |
|---|---|---|
| miR-101-1/2 | AGGCUGCCCUGGCUCAGUUAUCACAGUGCUGAUGCU GUCUAUUCUAAAGGUACAGUACUGUGAUAACUGAAG GAUGGCAGCCAUCUUACCUUCCAUCAGAGGAGCCUCA C | 98 |
| miR-101 | UCAGUUAUCACAGUGCUGAUGCUGUCCAUUCUAAAG GUACAGUACUGUGAUAACUGA | 99 |
| miR-101-1 | UGCCCUGGCUCAGUUAUCACAGUGCUGAUGCUGUCU AUUCUAAAGGUACAGUACUGUGAUAACUGAAGGAUG GCA | 100 |
| miR-101-2 | ACUGUCCUUUUCGGUUAUCAUGGUACCGAUGCUGU AUAUCUGAAAGGUACAGUACUGUGAUAACUGAAGAA UGGUGGU | 101 |
| miR-101-9 | UGUCCUUUUCGGUUAUCAUGGUACCGAUGCUGUAU AUCUGAAAGGUACAGUACUGUGAUAACUGAAGAAUG GUG | 102 |
| miR-102-1 | CUUCUGGAAGCUGGUUUCACAUGGUGGCUUAGAUUU UUCCAUCUUUUGUAUCUAGCACCAUUUGAAAUCAGUG UUUUAGGAG | 103 |
| miR-102-7.1 (miR-102-7.2) | CUUCAGGAAGCUGGUUUCAUAUGGUGGUUUAGAUUU AAAUAGUGAUUGUCUAGCACCAUUUGAAAUCAGUGU UCUUGGGGG | 104 |
| miR-103-2 | UUGUGCUUUCAGCUUCUUUACAGUGCUGCCUUGUAG CAUUCAGGUCAAGCAACAUUGUACAGGGCUAUGAAA GAACCA | 105 |
| miR-103-1 | UACUGCCCUCGGCUUCUUUACAGUGCUGCCUUGUUGC AUAUGGAUCAAGCAGCAUUGUACAGGGCUAUGAAGG CAUUG | 106 |
| miR-104-17 | AAAUGUCAGACAGCCCAUCGACUGGUGUUGCCAUGA GAUUCAACAGUCAACAUCAGUCUGAUAAGCUACCCG ACAAGG | 107 |
| miR-105-1 | UGUGCAUCGUGGUCAAAUGCUCAGACUCCUGUGGUG GCUGCUCAUGCACCACGGAUGUUUGAGCAUGUGCUA CGGUGUCUA | 108 |
| miR-105-2 | UGUGCAUCGUGGUCAAAUGCUCAGACUCCUGUGGUG GCUGCUUAUGCACCACGGAUGUUUGAGCAUGUGCUA UGGUGUCUA | 109 |
| miR-106-a | CCUUGGCCAUGUAAAAGUGCUUACAGUGCAGGUAGC UUUUUGAGAUCUACUGCAAUGUAAGCACUUCUUACA UUACCAUGG | 110 |
| miR-106-b | CCUGCCGGGGCUAAAGUGCUGACAGUGCAGAUAGUG GUCCUCUCCGUGCUACCGCACUGUGGGUACUUGCUGC UCCAGCAGG | 111 |
| miR-107 | CUCUCUGCUUUCAGCUUCUUUACAGUGUUGCCUUGU GGCAUGGAGUUCAAGCAGCAUUGUACAGGGCUAUCA AAGCACAGA | 112 |
| miR-108-1-small | ACACUGCAAGAACAAUAAGGAUUUUUAGGGGCAUUA UGACUGAGUCAGAAAACACAGCUGCCCCUGAAAGUC CCUCAUUUUUCUUGCUGU | 113 |
| miR-108-2-small | ACUGCAAGAGCAAUAAGGAUUUUUAGGGGCAUUAUG AUAGUGGAAUGGAAACACAUCUGCCCCCAAAAGUCC CUCAUUUU | 114 |
| miR-122a-1 | CCUUAGCAGAGCUGUGGAGUGUGACAAUGGUGUUUG UGUCUAAACUAUCAAACGCCAUUAUCACACUAAAUA GCUACUGCUAGGC | 115 |
| miR-122a-2 | AGCUGUGGAGUGUGACAAUGGUGUUUGUGUCCAAAC UAUCAAACGCCAUUAUCACACUAAAUAGCU | 116 |

TABLE 1a-continued

Human microRNA Precursor Sequences.

| Precursor Name | Sequence (5' To 3')* | SEQ ID NO. |
|---|---|---|
| miR-123 | ACAUUAUUACUUUUGGUACGCGCUGUGACACUUCAA ACUCGUACCGUGAGUAAUAAUGCGC | 117 |
| miR-124a-1 | AGGCCUCUCUCUCCGUGUUCACAGCGGACCUUGAUUU AAAUGUCCAUACAAUUAAGGCACGCGGUGAAUGCCA AGAAUGGGGCUG | 118 |
| miR-124a-2 | AUCAAGAUUAGAGGCUCUGCUCUCCGUGUUCACAGC GGACCUUGAUUUAAUGUCAUACAAUUAAGGCACGCG GUGAAUGCCAAGAGCGGAGCCUACGGCUGCACUUGA AG | 119 |
| miR-124a-3 | UGAGGGCCCCUCUGCGUGUUCACAGCGGACCUUGAU UUAUGUCUAUACAAUUAAGGCACGCGGUGAAUGCC AAGAGAGGCGCCUCC | 120 |
| miR-124a | CUCUGCGUGUUCACAGCGGACCUUGAUUUAAUGUCU AUACAAUUAAGGCACGCGGUGAAUGCCAAGAG | 121 |
| miR-124b | CUCUCCGUGUUCACAGCGGACCUUGAUUUAAUGUCA UACAAUUAAGGCACGCGGUGAAUGCCAAGAG | 122 |
| miR-125a-1 | UGCCAGUCUCUAGGUCCCUGAGACCCUUUAACCUGUG AGGACAUCCAGGGUCACAGGUGAGGUUCUUGGGAGC CUGGCGUCUGGCC | 123 |
| miR-125a-2 | GGUCCCUGAGACCCUUUAACCUGUGAGGACAUCCAG GGUCACAGGUGAGGUUCUUGGGAGCCUGG | 124 |
| miR-125b-1 | UGCGCUCCUCUCAGUCCCUGAGACCCUAACUUGUGAU GUUUACCGUUUAAAUCCACGGGUUAGGCUCUUGGGA GCUGCGAGUCGUGCU | 125 |
| miR-125b-2 | ACCAGACUUUUCCUAGUCCCUGAGACCCUAACUUGUG AGGUAUUUUAGUAACAUCACAAGUCAGGCUCUUGGG ACCUAGGCGGAGGGGA | 126 |
| miR-126-1 | CGCUGGCGACGGGACAUUAUUACUUUUGGUACGCGC UGUGACACUUCAAACUCGUACCGUGAGUAAUAAUGC GCCGUCCACGGCA | 127 |
| miR-126-2 | ACAUUAUUACUUUUGGUACGCGCUGUGACACUUCAA ACUCGUACCGUGAGUAAUAAUGCGC | 128 |
| miR-127-1 | UGUGAUCACUGUCUCCAGCCUGCUGAAGCUCAGAGG GCUCUGAUUCAGAAAGAUCAUCGGAUCCGUCUGAGC UUGGCUGGUCGGAAGUCUCAUCAUC | 129 |
| miR-127-2 | CCAGCCUGCUGAAGCUCAGAGGGCUCUGAUUCAGAA AGAUCAUCGGAUCCGUCUGAGCUUGGCUGGUCGG | 130 |
| miR-128a | UGAGCUGUUGGAUUCGGGGCCGUAGCACUGUCUGAG AGGUUUACAUUUCUCACAGUGAACCGGUCUCUUUUU CAGCUGCUUC | 131 |
| miR-128b | GCCCGGCAGCCACUGUGCAGUGGGAAGGGGGCCGA UACACUGUACGAGAGUGAGUAGCAGGUCUCACAGUG AACCGGUCUCUUUCCCUACUGUGUCACACUCCUAAUG G | 132 |
| miR-128 | GUUGGAUUCGGGGCCGUAGCACUGUCUGAGAGGUUU ACAUUUCUCACAGUGAACCGGUCUCUUUUUCAGC | 133 |
| miR-129-1 | UGGAUCUUUUUGCGGUCUGGGCUUGCUGUUCCUCUC AACAGUAGUCAGGAAGCCCUUACCCCAAAAAGUAUC UA | 134 |
| miR-129-2 | UGCCCUUCGCGAAUCUUUUUGCGGUCUGGGCUUGCU GUACAUAACUCAAUAGCCGGAAGCCCUUACCCCAAAA AGCAUUUGCGGAGGGCG | 135 |
| miR-130a | UGCUGCUGGCCAGAGCUCUUUUCACAUUGUGCUACU GUCUGCACCUGUCACUAGCAGUGCAAUGUUAAAAGG GCAUUGGCCGUGUAGUG | 136 |

TABLE 1a-continued

Human microRNA Precursor Sequences.

| Precursor Name | Sequence (5' To 3')* | SEQ ID NO. |
| --- | --- | --- |
| miR-131-1 | GCCAGGAGGCGGGGUUGGUUGUUAUCUUUGGUUAUC UAGCUGUAUGAGUGGUGUGGAGUCUUCAUAAAGCUA GAUAACCGAAAGUAAAAAUAACCCCAUACACUGCGC AG | 137 |
| miR-131-3 | CACGGCGCGGCAGCGGCACUGGCUAAGGGAGGCCCGU UUCUCUCUUUGGUUAUCUAGCUGUAUGAGUGCCACA GAGCCGUCAUAAAGCUAGAUAACCGAAAGUAGAAAU G | 138 |
| miR-131 | GUUGUUAUCUUUGGUUAUCUAGCUGUAUGAGUGUAU UGGUCUUCAUAAAGCUAGAUAACCGAAAGUAAAAAC | 139 |
| miR-132-1 | CCGCCCCCGCGUCUCCAGGGCAACCGUGGCUUUCGAU UGUUACUGUGGGAACUGGAGGUAACAGUCUACAGCC AUGGUCGCCCCGCAGCACGCCCACGCGC | 140 |
| miR-132-2 | GGGCAACCGUGGCUUUCGAUUGUUACUGUGGGAACU GGAGGUAACAGUCUACAGCCAUGGUCGCCC | 141 |
| miR-133a-1 | ACAAUGCUUUGCUAGAGCUGGUAAAAUGGAACCAAA UCGCCUCUUCAAUGGAUUUGGUCCCCUUCAACCAGCU GUAGCUAUGCAUUGA | 142 |
| miR-133a-2 | GGGAGCCAAAUGCUUUGCUAGAGCUGGUAAAAUGGA ACCAAAUCGACUGUCCAAUGGAUUUGGUCCCCUUCA ACCAGCUGUAGCUGUGCAUUGAUGGCGCCG | 143 |
| miR-133 | GCUAGAGCUGGUAAAAUGGAACCAAAUCGCCUCUUC AAUGGAUUUGGUCCCCUUCAACCAGCUGUAGC | 144 |
| miR-133b | CCUCAGAAGAAAGAUGCCCCCUGCUCUGGCUGGUCAA ACGGAACCAAGUCCGUCUUCCUGAGAGGUUUGGUCC CCUUCAACCAGCUACAGCAGGGCUGGCAAUGCCCAGU CCUUGGAGA | 145 |
| miR-133b-small | GCCCCCUGCUCUGGCUGGUCAAACGGAACCAAGUCCG UCUUCCUGAGAGGUUUGGUCCCCUUCAACCAGCUACA GCAGGG | 146 |
| miR-134-1 | CAGGGUGUGUGACUGGUUGACCAGAGGGGCAUGCAC UGUGUUCACCCUGUGGGCCACCUAGUCACCAACCCUC | 147 |
| miR-134-2 | AGGGUGUGUGACUGGUUGACCAGAGGGGCAUGCACU GUGUUCACCCUGUGGGCCACCUAGUCACCAACCCU | 148 |
| miR-135a-1 | AGGCCUCGCUGUUCUCUAUGGCUUUUUAUUCCUAUG UGAUUCUACUGCUCACUCAUAUAGGGAUUGGAGCCG UGGCGCACGGCGGGGACA | 149 |
| miR-135a-2 (miR-135-2) | AGAUAAAUUCACUCUAGUGCUUUAUGGCUUUUUAUU CCUAUGUGAUAGUAAUAAAGUCUCAUGUAGGGAUGG AAGCCAUGAAAUACAUUGUGAAAAAUCA | 150 |
| miR-135 | CUAUGGCUUUUUAUUCCUAUGUGAUUCUACUGCUCA CUCAUAUAGGGAUUGGAGCCGUGG | 151 |
| miR-135b | CACUCUGCUGUGGCCUAUGGCUUUUCAUUCCUAUGU GAUUGCUGUCCCAAACUCAUGUAGGGCUAAAAGCCA UGGGCUACAGUGAGGGGCGAGCUCC | 152 |
| miR-136-1 | UGAGCCCUCGGAGGACUCCAUUUGUUUUGAUGAUGG AUUCUUAUGCUCCAUCAUCGUCUCAAAUGAGUCUUC AGAGGGUUCU | 153 |
| miR-136-2 | GAGGACUCCAUUUGUUUUGAUGAUGGAUUCUUAUGC UCCAUCAUCGUCUCAAAUGAGUCUUC | 154 |
| miR-137 | CUUCGGUGACGGGUAUUCUUGGGUGGAUAAUACGGA UUACGUUGUUAUUGCUUAAGAAUACGCGUAGUCGAG G | 155 |
| miR-138-1 | CCCUGGCAUGGUGUGGUGGGGGCAGCUGGUGUUGUGA AUCAGGCCGUUGCCAAUCAGAGAACGGCUACUUCAC AACACCAGGGCCACACCACACUACAGG | 156 |

TABLE 1a-continued

Human microRNA Precursor Sequences.

| Precursor Name | Sequence (5' To 3')* | SEQ ID NO. |
|---|---|---|
| miR-138-2 | CGUUGCUGCAGCUGGUGUUGUGAAUCAGGCCGACGA GCAGCGCAUCCUCUUACCCGGCUAUUUCACGACACCA GGGUUGCAUCA | 157 |
| miR-138 | CAGCUGGUGUUGUGAAUCAGGCCGACGAGCAGCGCA UCCUCUUACCCGGCUAUUUCACGACACCAGGGUUG | 158 |
| miR-139 | GUGUAUUCUACAGUGCACGUGUCUCCAGUGUGGCUC GGAGGCUGGAGACGCGGCCCUGUUGGAGUAAC | 159 |
| miR-140 | UGUGUCUCUCUCUGUGUCCUGCCAGUGGUUUUACCC UAUGGUAGGUUACGUCAUGCUGUUCUACCACAGGGU AGAACCACGGACAGGAUACCGGGGCACC | 160 |
| miR-140as | UCCUGCCAGUGGUUUUACCCUAUGGUAGGUUACGUC AUGCUGUUCUACCACAGGGUAGAACCACGGACAGGA | 161 |
| miR-140s | CCUGCCAGUGGUUUUACCCUAUGGUAGGUUACGUCA UGCUGUUCUACCACAGGGUAGAACCACGGACAGG | 162 |
| miR-141-1 | CGGCCGGCCCUGGGUCCAUCUUCCAGUACAGUGUUGG AUGGUCUAAUUGUGAAGCUCCUAACACUGUCUGGUA AAGAUGGCUCCCGGGUGGGUUC | 163 |
| miR-141-2 | GGGUCCAUCUUCCAGUACAGUGUUGGAUGGUCUAAU UGUGAAGCUCCUAACACUGUCUGGUAAAGAUGGCCC | 164 |
| miR-142 | ACCCAUAAAGUAGAAAGCACUACUAACAGCACUGGA GGGUGUAGUGUUUCCUACUUUAUGGAUG | 165 |
| miR-143-1 | GCGCAGCGCCCUGUCUCCCAGCCUGAGGUGCAGUGCU GCAUCUCUGGUCAGUUGGGAGUCUGAGAUGAAGCAC UGUAGCUCAGGAAGAGAGAAGUUGUUCUGCAGC | 166 |
| miR-143-2 | CCUGAGGUGCAGUGCUGCAUCUCUGGUCAGUUGGGA GUCUGAGAUGAAGCACUGUAGCUCAGG | 167 |
| miR-144-1 | UGGGGCCCUGGCUGGGAUAUCAUCAUAUACUGUAAAG UUUGCGAUGAGACACUACAGUAUAGAUGAUGUACUA GUCCGGGCACCCCC | 168 |
| miR-144-2 | GGCUGGGAUAUCAUCAUAUACUGUAAGUUUGCGAUG AGACACUACAGUAUAGAUGAUGUACUAGUC | 169 |
| miR-145-1 | CACCUUGUCCUCACGGUCCAGUUUUCCCAGGAAUCCC UUAGAUGCUAAGAUGGGGAUUCCUGGAAAUACUGUU CUUGAGGUCAUGGUU | 170 |
| miR-145-2 | CUCACGGUCCAGUUUUCCCAGGAAUCCCUUAGAUGCU AAGAUGGGGAUUCCUGGAAAUACUGUUCUUGAG | 171 |
| miR-146-1 | CCGAUGUGUAUCCUCAGCUUUGAGAACUGAAUUCCA UGGGUUGUGUCAGUGUCAGACCUCUGAAAUUCAGUU CUUCAGCUGGGAUAUCUCUGUCAUCGU | 172 |
| miR-146-2 | AGCUUUGAGAACUGAAUUCCAUGGGUUGUGUCAGUG UCAGACCUGUGAAAUUCAGUUCUUCAGCU | 173 |
| miR-147 | AAUCUAAAGACAACAUUUCUGCACACACACCAGACU AUGGAAGCCAGUGUGUGGAAAUGCUUCUGCUAGAUU | 174 |
| miR-148a (miR-148) | GAGGCAAAGUUCUGAGACACUCCGACUCUGAGUAUG AUAGAAGUCAGUGCACUACAGAACUUUGUCUC | 175 |
| miR-148b | CAAGCACGAUUAGCAUUUGAGGUGAAGUUCUGUUAU ACACUCAGGCUGUGGCUCUCUGAAAGUCAGUGCAUC ACAGAACUUUGUCUCGAAAGCUUUCUA | 176 |
| miR-148b-small | AAGCACGAUUAGCAUUUGAGGUGAAGUUCUGUUAUA CACUCAGGCUGUGGCUCUCUGAAAGUCAGUGCAU | 177 |
| miR-149-1 | GCCGGCGCCCGAGCUCUGGCUCCGUGUCUUCACUCCC GUGCUUGUCCGAGGAGGGAGGGAGGGACGGGGGCUG UGCUGGGGCAGCUGGA | 178 |

TABLE 1a-continued

Human microRNA Precursor Sequences.

| Precursor Name | Sequence (5' To 3')* | SEQ ID NO. |
|---|---|---|
| miR-149-2 | GCUCUGGCUCCGUGUCUUCACUCCCGUGCUUGUCCGAGGAGGGAGGGAGGGAC | 179 |
| miR-150-1 | CUCCCCAUGGCCCUGUCUCCCAACCCUUGUACCAGUGCUGGGCUCAGACCCUGUACAGGCCUGGGGACAGGGACCUGGGGAC | 180 |
| miR-150-2 | CCCUGUCUCCCAACCCUUGUACCAGUGCUGGGCUCAGACCCUGGUACAGGCCUGGGGACAGGG | 181 |
| miR-151 | UUUCCUGCCCUCGAGGAGCUCACAGUCUAGUAUGUCUCAUCCCCUACUAGACUGAAGCUCCUUGAGGACAGG | 182 |
| miR-151-2 | CCUGUCCUCAAGGAGCUUCAGUCUAGUAGGGGAUGAGACAUACUAGACUGUGAGCUCCUCGAGGGCAGG | 183 |
| miR-152-1 | UGUCCCCCCGGCCCAGGUUCUGUGAUACACUCCGACUCGGGCUCUGGAGCAGUCAGUGCAUGACAGAACUUGGGCCCGGAAGGACC | 184 |
| miR-152-2 | GGCCCAGGUUCUGUGAUACACUCCGACUCGGGCUCUGGAGCAGUCAGUGCAUGACAGAACUUGGGCCCCGG | 185 |
| miR-153-1-1 | CUCACAGCUGCCAGUGUCAUUUUUGUGAUCUGCAGCUAGUAUUCUCACUCCAGUUGCAUAGUCACAAAAGUGAUCAUUGGCAGGUGUGGC | 186 |
| miR-153-1-2 | UCUCUCUCUCCCUCACAGCUGCCAGUGUCAUUGUCACAAAAGUGAUCAUUGGCAGGUGUGGCUGCUGCAUG | 187 |
| miR-153-2-1 | AGCGGUGGCCAGUGUCAUUUUUGUGAUGUUGCAGCUAGUAAUAUGAGCCCAGUUGCAUAGUCACAAAAGUGAUCAUUGGAAACUGUG | 188 |
| miR-153-2-2 | CAGUGUCAUUUUUGUGAUGUUGCAGCUAGUAAUAUGAGCCCAGUUGCAUAGUCACAAAAGUGAUCAUUG | 189 |
| miR-154-1 | GUGGUACUUGAAGAUAGGUUAUCCGUGUUGCCUUCGCUUUAUUUGUGACGAAUCAUACACGGUUGACCUAUUUUUCAGUACCAA | 190 |
| miR-154-2 | GAAGAUAGGUUAUCCGUGUUGCCUUCGCUUUAUUUGUGACGAAUCAUACACGGUUGACCUAUUUUU | 191 |
| miR-155 | CUGUUAAUGCUAAUCGUGAUAGGGGUUUUUGCCUCCAACUGACUCCUACAUAUUAGCAUUAACAG | 192 |
| miR-156 = miR-157 = overlap miR-141 | CCUAACACUGUCUGGUAAAGAUGGCUCCCGGGUGGGUUCUCUCGGCAGUAACCUUCAGGGAGCCCUGAAGACCAUGGAGGAC | 193 |
| miR-158-small = miR-192 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | 194 |
| miR-159-1-small | UCCCGCCCCCUGUAACAGCAACUCCAUGUGGAAGUGCCCACUGGUUCCAGUGGGGCUGCUGUUAUCUGGGGCGAGGGCCA | 195 |
| miR-161-small | AAAGCUGGGUUGAGAGGGCGAAAAAGGAUGAGGUGACUGGUCUGGGCUACGCUAUGCUGCGGCGCUCGGG | 196 |
| miR-163-1b-small | CAUUGGCCUCCUAAGCCAGGGAUUGUGGGUUCGAGUCCCACCCGGGGUAAAGAAAGGCCGAAUU | 197 |
| miR-163-3-small | CCUAAGCCAGGGAUUGUGGGUUCGAGUCCCACCUGGGGUAGAGGUGAAAGUUCCUUUUACGGAAUUUUUU | 198 |
| miR-162 | CAAUGUCAGCAGUGCCUUAGCAGCACGUAAAUAUUGGCGUUAAGAUUCUAAAAUUAUCUCCAGUAUUAACUGUGCUGCUGAAGUAAGGUUGACCAUACUCUACAGUUG | 199 |

TABLE 1a-continued

Human microRNA Precursor Sequences.

| Precursor Name | Sequence (5' To 3')* | SEQ ID NO. |
|---|---|---|
| miR-175-small = miR-224 | GGGCUUUCAAGUCACUAGUGGUUCCGUUUAGUAGAU GAUUGUGCAUUGUUUCAAAAUGGUGCCCUAGUGACU ACAAAGCCC | 200 |
| miR-177-small | ACGCAAGUGUCCUAAGGUGAGCUCAGGGAGCACAGA AACCUCCAGUGGAACAGAAGGGCAAAAGCUCAUU | 201 |
| miR-180-small | CAUGUGUCACUUUCAGGUGGAGUUUCAAGAGUCCCU UCCUGGUUCACCGUCUCCUUUGCUCUUCCACAAC | 202 |
| miR-181a | AGAAGGGCUAUCAGGCCAGCCUUCAGAGGACUCCAA GG<u>AACAUUCAACGCUGUCGGUGAGUUUGGGAUUUGA</u> AAAAACCACUGACCGUUGACUGUACCUUGGGGUCCU UA | 203 |
| miR-181b-1 | CCUGUGCAGAGAUUAUUUUUAAAAGGUCACAAUC<u>A ACAUUCAUUGCUGUCGGUGGGUU</u>GAACUGUGUGGAC AAGCUCACUGAACAAUGAAUGCAACUGUGGCCCCGC UU | 204 |
| miR-181b-2 | CUGAUGGCUGCACUC<u>AACAUUCAUUGCUGUCGGUGG GUUU</u>GAGUCUGAAUCAACUCACUGAUCAAUGAAUGC AAACUGCGGACCAAACA | 205 |
| miR-181c | CGGAAAAUUUGCCAAGGGUUUGGGGG<u>AACAUUCAAC CUGUCGGUGAGUUUGGG</u>CAGCUCAGGCAAACCAUCG ACCGUUGAGUGGACCCUGAGGCCUGGAAUUGCCAUC CU | 206 |
| miR-182-as | GAGCUGCUUGCCUCCCCCGUUU<u>UUGGCAAUGGUAG AACUCACA</u>CUGGUGAGGUAACAGGAUCCG<u>UGGUUC UAGACUUGCCAACUA</u>UGGGGCGAGGACUCAGCCGGC AC | 207 |
| miR-182 | <u>UUUUUGGCAAUGGUAGAACUCACAC</u>UGGUGAGGUAA CAGGAUCCGG<u>UGGUUCUAGACUUGCCAACUA</u>UGG | 208 |
| miR-183 | CCGCAGAGUGUGACUCCUGUUCUGUGU<u>AUGGCACUG GUAGAAUUCACUG</u>UGAACAGUCUCAGUCAGUGAAUU ACCGAAGGGCCAUAAACAGAGCAGAGACAGAUCCAC GA | 209 |
| miR-184-1 | CCAGUCACGUCCCCUUAUCACUUUUCCAGCCCAGCUU UGUGACUGUAAGUGU<u>UGGACGGAGAACUGAUAAGGG UAGG</u>UGAUUGA | 210 |
| miR-184-2 | CCUUAUCACUUUUCCAGCCCAGCUUUGUGACUGUAA GUGU<u>UGGACGGAGAACUGAUAAGGG</u>UAGG | 211 |
| miR-185-1 | AGGGGGCGAGGGAU<u>UGGAGAGAAAGGCAGUUCC</u>UGA UGGUCCCCUCCCCAGGGGCUGGCUUUCCUCUGGUCCU UCCCUCCCA | 212 |
| miR-185-2 | AGGGAU<u>UGGAGAGAAAGGCAGUUCC</u>UGAUGGUCCCC UCCCCAGGGGCUGGCUUUCCUCUGGUCCUU | 213 |
| miR-186-1 | UGCUUGUAACUUUC<u>CAAAGAAUUCUCCUUUUGGGCU</u> UUCUGGUUUUAUUUUAAGCCCAAAGGUGAAUUUUUU GGGAAGUUUGAGCU | 214 |
| miR-186-2 | ACUUUC<u>CAAAGAAUUCUCCUUUUGGGCUU</u>UCUGGUU UUAUUUUAAGCCCAAAGGUGAAUUUUUUGGGAAGU | 215 |
| miR-187 | GGUCGGGCUCACCAUGACACAGUGUGAGACUCGGGC UACAACACAGGACCCGGGGCGCUGCUCUGACCCC<u>UCG UGUCUUGUGUUGCAGCCGG</u>AGGGACGCAGGUCCGCA | 216 |
| miR-188-1 | UGCUCCCUCUCUCA<u>CAUCCCUUGCAUGGUGGAGGGUG</u> AGCUUUCUGAAAACCCCUCCCACAUGCAGGGUUUGCA GGAUGGCGAGCC | 217 |
| miR-188-2 | UCUCA<u>CAUCCCUUGCAUGGUGGAGGGUG</u>AGCUUUCU GAAAACCCCUCCCACAUGCAGGGUUUGCAGGA | 218 |

TABLE 1a-continued

Human microRNA Precursor Sequences.

| Precursor Name | Sequence (5' To 3')* | SEQ ID NO. |
| --- | --- | --- |
| miR-189-1 | CUGUCGAUUGGACCCGCCCUCCGGUGCCUACUGAGCUGAUAUCAGUUCUCAUUUUACACACUGGCUCAGUUCAGCAGGAACAGGAGUCGAGCCCUUGAGCAA | 219 |
| miR-189-2 | CUCCGGUGCCUACUGAGCUGAUAUCAGUUCUCAUUUUACACACUGGCUCAGUUCAGCAGGAACAGGAG | 220 |
| miR-190-1 | UGCAGGCCUCUGUGUGAUAUGUUUGAUAUAUUAGGUUGUUAUUUAAUCCAACUAUAUAUCAAACAUAUUCCUACAGUGUCUUGCC | 221 |
| miR-190-2 | CUGUGUGAUAUGUUUGAUAUAUUAGGUUGUUAUUUAAUCCAACUAUAUAUCAAACAUAUUCCUACAG | 222 |
| miR-191-1 | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU | 223 |
| miR-191-2 | AGCGGGCAACGGAAUCCCAAAAGCAGCUGUUGUCUCCAGAGCAUUCCAGCUGCGCUUGGAUUUCGUCCCCUGCU | 224 |
| miR-192-2/3 | CCGAGACCGAGUGCACAGGGCUCUGACCUAUGAAUUGACAGCCAGUGCUCUCGUCUCCCCUCUGGCUGCAAUUCCAUAGGUCACAGGUAUGUUCGCCUCAAUGCCAG | 225 |
| miR-192 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | 226 |
| miR-193-1 | CGAGGAUGGGAGCUGAGGGCUGGGUCUUUGCGGGCGAGAUGAGGGUGUCGGAUCAACUGGCCUACAAAGUCCCAGUUCUCGGCCCCCG | 227 |
| miR-193-2 | GCUGGGUCUUUGCGGGCGAGAUGAGGGUGUCGGAUCAACUGGCCUACAAAGUCCCAGU | 228 |
| miR-194-1 | AUGGUGUUAUCAAGUGUAACAGCAACUCCAUGUGGACUGUGUACCAAUUUCCAGUGGAGAUGCUGUUACUUUUGAUGGUUACCAA | 229 |
| miR-194-2 | GUGUAACAGCAACUCCAUGUGGACUGUGUACCAAUUUCCAGUGGAGAUGCUGUUACUUUUGAU | 230 |
| miR-195-1 | AGCUUCCUGGCUCUAGCAGCACAGAAAUAUUGGCACAGGGAAGCGAGUCUGCCAAUAUUGGCUGUGCUGCUCCAGGCAGGGUGGUG | 231 |
| miR-195-2 | UAGCAGCACAGAAAUAUUGGCACAGGGAAGCGAGUCUGCCAAUAUUGGCUGUGCUGCU | 232 |
| miR-196-1 | CUAGAGCUUGAAUUGGAACUGCUGAGUGAAUUAGGUAGUUUCAUGUUGUUGGGCCUGGGUUUCUGAACACAACAACAUUAAACCACCCGAUUCACGGCAGUUACUGCUCC | 233 |
| miR-196a-1 | GUGAAUUAGGUAGUUUCAUGUUGUUGGGCCUGGGUUUCUGAACACAACAACAUUAAACCACCCGAUUCAC | 234 |
| miR-196a-2 (miR-196-2) | UGCUCGCUCAGCUGAUCUGUGGCUUAGGUAGUUUCAUGUUGUUGGGAUUGAGUUUUGAACUCGGCAACAAGAAACUGCCUGAGUUACAUCAGUCGGUUUUCGUCGAGGGC | 235 |
| miR-196 | GUGAAUUAGGUAGUUUCAUGUUGUUGGGCCUGGGUUUCUGAACACAACAACAUUAAACCACCCGAUUCAC | 236 |
| miR-196b | ACUGGUCGUGAUUUAGGUAGUUUCCUGUUGUUGGGAUCCACCUUUCUCUCGACAGCACGACACUGCCUUCAUUACUUCAGUUG | 237 |
| miR-197 | GGCUGUGCCGGGUAGAGAGGGCAGUGGGAGGUAAGAGCUCUUCACCCUUCACCACCUUCUCCACCCAGCAUGGCC | 238 |

TABLE 1a-continued

Human microRNA Precursor Sequences.

| Precursor Name | Sequence (5' To 3')* | SEQ ID NO. |
|---|---|---|
| miR-197-2 | GUGCAUGUGUAUGUAUGUGUGCAUGUGCAUGUGUAUGUGUAUGAGUGCAUGCGUGUGUGC | 239 |
| miR-198 | UCAUUGGUCCAGAGGGGAGAUAGGUUCCUGUGAUUUUUCCUUCUUCUCUAUAGAAUAAAUGA | 240 |
| miR-199a-1 | GCCAACCCAGUGUUCAGACUACCUGUUCAGGAGGCUCUCAAUGUGUACAGUAGUCUGCACAUUGGUUAGGC | 241 |
| miR-199a-2 | AGGAAGCUUCUGGAGAUCCUGCUCCGUCGCCCCAGUGUUCAGACUACCUGUUCAGGACAAUGCCGUUGUACAGUAGUCUGCACAUUGGUUAGACUGGGCAAGGGAGAGCA | 242 |
| miR-199b | CCAGAGGACACCUCCACUCCGUCUACCCAGUGUUUAGACUAUCUGUUCAGGACUCCCAAAUUGUACAGUAGUCUGCACAUUGGUUAGGCUGGGCUGGGUUAGACCCUCGG | 243 |
| miR-199s | GCCAACCCAGUGUUCAGACUACCUGUUCAGGAGGCUCUCAAUGUGUACAGUAGUCUGCACAUUGGUUAGGC | 244 |
| miR-200a | GCCGUGGCCAUCUUACUGGGCAGCAUUGGAUGGAGUCAGGUCUCUAAUACUGCCUGGUAAUGAUGACGGC | 245 |
| miR-200b | CCAGCUCGGGCAGCCGUGGCCAUCUUACUGGGCAGCAUUGGAUGGAGUCAGGUCUCUAAUACUGCCUGGUAAUGAUGACGGCGGAGCCCUGCACG | 246 |
| miR-200c | CCCUCGUCUUACCCAGCAGUGUUUGGGUGCGGUUGGGAGUCUCUAAUACUGCCGGGUAAUGAUGGAGG | 247 |
| miR-202 | GUUCCUUUUCCUAUGCAUAUACUUCUUUGAGGAUCUGGCCUAAAGAGGUAUAGGGCAUGGGAAGAUGGAGC | 248 |
| miR-203 | GUGUUGGGGACUCGCGCGCUGGGUCCAGUGGUUCUUAACAGUUCAACAGUUCUGUAGCGCAAUUGUGAAAUGUUUAGGACCACUAGACCCGGCGGGCGCGGCGACAGCGA | 249 |
| miR-204 | GGCUACAGUCUUUCUUCAUGUGACUCGUGGACUUCCCUUUGUCAUCCUAUGCCUGAGAAUAUAUGAAGGAGGCUGGGAAGGCAAAGGGACGUUCAAUUGUCAUCACUGGC | 250 |
| miR-205 | AAAGAUCCUCAGACAAUCCAUGUGCUUCUCUUGUCCUUCAUUCCACCGGAGUCUGUCUCAUACCCAACCAGAUUUCAGUGGAGUGAAGUUCAGGAGGCAUGGAGCUGACA | 251 |
| miR-206-1 | UGCUUCCCGAGGCCACAUGCUUCUUUAUAUCCCCAUAUGGAUUACUUUGCUAUGGAAUGUAAGGAAGUGUGUGGUUUCGGCAAGUG | 252 |
| miR-206-2 | AGGCCACAUGCUUCUUUAUAUCCCCAUAUGGAUUACUUUGCUAUGGAAUGUAAGGAAGUGUGUGGUUUU | 253 |
| miR-208 | UGACGGGCGAGCUUUUGGCCCGGGUUAUACCUGAUGCUCACGUAUAAGACGAGCAAAAAGCUUGUUGGUCA | 254 |
| miR-210 | ACCCGGCAGUGCCUCCAGGCGCAGGGCAGCCCCUGCCCACCGCACACUGCGCUGCCCCAGACCCACUGUGCGUGUGACAGCGGCUGAUCUGUGCCUGGGCAGCGCGACCC | 255 |
| miR-211 | UCACCUGGCCAUGUGACUUGUGGGCUUCCCUUUGUCAUCCUUCGCCUAGGGCUCUGAGCAGGGCAGGGACAGCAAAGGGGUGCUCAGUUGUCACUUCCCACAGCACGGAG | 256 |
| miR-212 | CGGGGCACCCCGCCCGGACAGCGCGCCGGCACCUUGGCUCUAGACUGCUUACUGCCCGGGCCGCCCUCAGUAACAGUCUCCAGUCACGGCCACCGACGCCUGGCCCCGCC | 257 |

TABLE 1a-continued

Human microRNA Precursor Sequences.

| Precursor Name | Sequence (5' To 3')* | SEQ ID NO. |
|---|---|---|
| miR-213-2 | CCUGUGCAGAGAUUAUUUUUUAAAAGGUCACAAUCA<u>ACAUUCAUUGCUGUCGGUGGGUU</u>GAACUGUGUGGAC AAGCUCACUGAACAAUGAAUGCAACUGUGGCCCCGC UU | 258 |
| miR-213 | GAGUUUUGAGGUUGCUUCAGUGAACAUUCAACGCUG UCGGUGAGUUUGGAAUUAAAAUCAAA<u>ACCAUCGACC GUUGAUUGUACCC</u>UAUGGCUAACCAUCAUCUACUCC | 259 |
| miR-214 | GGCCUGGCUGGACAGAGUUGUCAUGUGUCUGCCUGU CUACACUUGCUGUGCAGAACAUCCGCUCACCUGU<u>ACA GCAGGCACAGACAGGCAG</u>UCACAUGACAACCCAGCCU | 260 |
| miR-215 | AUCAUUCAGAAAUGGUAUACAGGAAA<u>AUGACCUAUG AAUUGACAGAC</u>AAUAUAGCUGAGUUUGUCUGUCAUU UCUUUAGGCCAAUAUUCUGUAUGACUGUGCUACUUC AA | 261 |
| miR-216 | GAUGGCUGUGAGUUGGCU<u>UAAUCUCAGCUGGCAACU GUG</u>AGAUGUUCAUACAAUCCCUCACAGUGGUCUCUG GGAUUAUGCUAAACAGAGCAAUUUCCUAGCCCUCAC GA | 262 |
| miR-217 | AGUAUAAUUAUUACAUAGUUUUUGAUGUCGCAGAU<u>A CUGCAUCAGGAACUGAUUGGAU</u>AAGAAUCAGUCACC AUCAGUUCCUAAUGCAUUGCCUUCAGCAUCUAAACA AG | 263 |
| miR-218-1 | GUGAUAAUGUAGCGAGAUUUUCUG<u>UUGUGCUUGAUC UAACCAUGUGGUU</u>GCGAGGUAUGAGUAAAACAUGGU UCCGUCAAGCACCAUGGAACGUCACGCAGCUUUCUAC A | 264 |
| miR-218-2 | GACCAGUCGCUGCGGGGCUUUCC<u>UUUGUGCUUGAUC UAACCAUGUGGUGG</u>AACGAUGGAAACGGAACAUGGU UCUGUCAAGCACCGCGGAAAGCACCGUGCUCUCCUGC A | 265 |
| miR-219 | CCGCCCCGGGCCGCGGCUCC<u>UGAUUGUCCAAACGCAA UUCU</u>CGAGUCUAUGGCUCCGGCCGAGAGUUGAGUCU GGACGUCCCGAGCCGCCGCCCCCAAACCUCGAGCGGG | 266 |
| miR-219-1 | CCGCCCCGGGCCGCGGCUCC<u>UGAUUGUCCAAACGCAA UUCU</u>CGAGUCUAUGGCUCCGGCCGAGAGUUGAGUCU GGACGUCCCGAGCCGCCGCCCCCAAACCUCGAGCGGG | 267 |
| miR-219-2 | ACUCAGGGGCUUCGCCAC<u>UGAUUGUCCAAACGCAAU UCU</u>UGUACGAGUCUGCGGCCAACCGAGAAUUGUGGC UGGACAUCUGUGGCUGAGCUCCGGG | 268 |
| miR-220 | GACAGUGUGGCAUUGUAGGGCU<u>CCACACCGUAUCUG ACACUUUG</u>GGCGAGGGCACCAUGCUGAAGGUGUUCA UGAUGCGGUCUGGGAACUCCUCACGGAUCUUACUGA UG | 269 |
| miR-221 | UGAACAUCCAGGUCUGGGGCAUGAACCUGGCAUACA AUGUAGAUUUCUGUGUUCGUUAGGCAAC<u>AGCUACAU UGUCUGCUGGGUUUC</u>AGGCUACCUGGAAACAUGUUC UC | 270 |
| miR-222 | GCUGCUGGAAGGUGUAGGUACCCUCAAUGGCUCAGU AGCCAGUGUAGAUCCUGUCUUUCGUAAUCAG<u>AGCU ACAUCUGGCUACUGGGUCUC</u>UGAUGGCAUCUUCUAG CU | 271 |
| miR-223 | CCUGGCCUCCUGCAGUGCCACGCUCCGUGUAUUUGAC AAGCUGAGUUGGACACUCCAUGUGGUAGAGUGUCAG <u>UUUGUCAAAUACCCC</u>AAGUGCGGCACAUGCUUACCA G | 272 |
| miR-224 | GGGCUUUC<u>AAGUCACUAGUGGUUCCGUUUAGUAGAU GAUUGUGCAUUGUUUCAAAAUGGUGCCCUAGUGACU</u> ACAAAGCCC | 273 |

TABLE 1a-continued

Human microRNA Precursor Sequences.

| Precursor Name | Sequence (5' To 3')* | SEQ ID NO. |
|---|---|---|
| miR-294-1(chr16) | CAAUCUUCCUUUAUCAUGGUAUUGAUUUUUCAGUGCUUCCCUUUUGUGUGAGAGAAGAUA | 274 |
| miR-296 | AGGACCCUUCCAGAGGGCCCCCCCUCAAUCCUGUUGUGCCUAAUUCAGAGGGUUGGGUGGAGGCUCUCCUGAAGGGCUCU | 275 |
| miR-299 | AAGAAAUGGUUUACCGUCCCACAUACAUUUUGAAUAUGUAUGUGGGAUGGUAAACCGCUUCUU | 276 |
| miR-301 | ACUGCUAACGAAUGCUCUGACUUUAUUGCACUACUGUACUUUACAGCUAGCAGUGCAAUAGUAUUGUCAAAGCAUCUGAAAGCAGG | 277 |
| miR-302a | CCACCACUUAAACGUGGAUGUACUUGCUUUGAAACUAAAGAAGUAAGUGCUUCCAUGUUUUGGUGAUGG | 278 |
| miR-302b | GCUCCCUUCAACUUUAACAUGGAAGUGCUUUCUGUGACUUUAAAAGUAAGUGCUUCCAUGUUUUAGUAGGAGU | 279 |
| miR-302c | CCUUUGCUUUAACAUGGGGGUACCUGCUGUGUGAAACAAAAGUAAGUGCUUCCAUGUUUCAGUGGAGG | 280 |
| miR-302d | CCUCUACUUUAACAUGGAGGCACUUGCUGUGACAUGACAAAAAUAAGUGCUUCCAUGUUUGAGUGUGG | 281 |
| miR-320 | GCUUCGCUCCCCUCCGCCUUCUCUUCCCGGUUCUUCCCGGAGUCGGGAAAAGCUGGGUUGAGAGGGCGAAAAAGGAUGAGGU | 282 |
| miR-321 | UUGGCCUCCUAAGCCAGGGAUUGUGGGUUCGAGUCCCACCCGGGGUAAAGAAAGGCCGA | 283 |
| miR-323 | UUGGUACUUGGAGAGAGGUGGUCCGUGGCGCGUUCGCUUUAUUUAUGGCGCACAUUACACGGUCGACCUCUUUGCAGUAUCUAAUC | 284 |
| miR-324 | CUGACUAUGCCUCCCCGCAUCCCCUAGGGCAUUGGUGUAAAGCUGGAGACCCACUGCCCCAGGUGCUGCUGGGGGUUGUAGUC | 285 |
| miR-325 | AUACAGUGCUUGGUUCCUAGUAGGUGUCCAGUAAGUGUUUGUGACAUAAUUUGUUUAUUGAGGACCUCCUAUCAAUCAAGCACUGUGCUAGGCUCUGG | 286 |
| miR-326 | CUCAUCUGUCUGUUGGGCUGGAGGCAGGGCCUUUGUGAAGGCGGGUGGUGCUCAGAUCGCCUCUGGGCCCUUCCUCCAGCCCCGAGGCGGAUUCA | 287 |
| miR-328 | UGGAGUGGGGGGCAGGAGGGGCUCAGGGAGAAAGUGCAUACAGCCCCUGGCCCUCUCUGCCCUUCCGUCCCCUG | 288 |
| miR-330 | CUUUGGCGAUCACUGCCUCUCUGGGCCUGUGUCUUAGGCUCUGCAAGAUCAACCGAGCAAAGCACACGGCCUGCAGAGAGGCAGCGCUCUGCCC | 289 |
| miR-331 | GAGUUUGGUUUUGUUUGGGUUUGUUCUAGGUAUGGUCCCAGGGAUCCCAGAUCAAACCAGGCCCCUGGGCCUAUCCUAGAACCAACCUAAGCUC | 290 |
| miR-335 | UGUUUUGAGCGGGGGUCAAGAGCAAUAACGAAAAAUGUUUGUCAUAAACCGUUUUUCAUUAUUGCUCCUGACCUCCUCUCAUUUGCUAUAUUCA | 291 |
| miR-337 | GUAGUCAGUAGUUGGGGGUGGGAACGGCUUCAUACAGGAGUUGAUGCACAGUUAUCCAGCUCCUAUAUGAUGCCUUUCUUCAUCCCCUUCAA | 292 |
| miR-338 | UCUCCAACAAUAUCCUGGUGCUGAGUGAUGACUCAGGCGACUCCAGCAUCAGUGAUUUUGUUGAAGA | 293 |

TABLE 1a-continued

Human microRNA Precursor Sequences.

| Precursor Name | Sequence (5' To 3')* | SEQ ID NO. |
|---|---|---|
| miR-339 | CGGGGCGGCCGCUCUCCCUGUCCUCCAGGAGCUCAC GUGUGCCUGCCUGUGAGCGCCUCGACGACAGAGCCG GCGCCUGCCCCAGUGUCUGCGC | 294 |
| miR-340 | UUGUACCUGGUGUGAUUAUAAAGCAAUGAGACUGA UUGUCAUAUGUCGUUUGUGGGAUCCGUCUCAGUUA CUUUAUAGCCAUACCUGGUAUCUUA | 295 |
| miR-342 | GAAACUGGGCUCAAGGUGAGGGGUGCUAUCUGUGA UUGAGGGACAUGGUUAAUGGAAUUGUCUCACACAG AAAUCGCACCCGUCACCUUGGCCUACUUA | 296 |
| miR-345 | ACCCAAACCCUAGGUCUGCUGACUCCUAGUCCAGGG CUCGUGAUGGCUGGUGGGCCCUGAACGAGGGGUCU GGAGGCCUGGGUUUGAAUAUCGACAGC | 297 |
| miR-346 | GUCUGUCUGCCCGCAUGCCUGCCUCUCUGUUGCUCU GAAGGAGGCAGGGGCUGGGCCUGCAGCUGCCUGGG CAGAGCGGCUCCUGC | 298 |
| miR-367 | CCAUUACUGUUGCUAAUAUGCAACUCUGUUGAAUA UAAAUUGGAAUUGCACUUUAGCAAUGGUGAUGG | 299 |
| miR-368 | AAAAGGUGGAUAUUCCUUCUAUGUUUAUGUUAUUU AUGGUUAAACAUAGAGGAAAUUCCACGUUUU | 300 |
| miR-369 | UUGAAGGGAGAUCGACCGUGUUAUAUUCGCUUUAU UGACUUCGAAUAAUACAUGGUUGAUCUUUUCUCAG | 301 |
| miR-370 | AGACAGAGAAGCCAGGUCACGUCUCUGCAGUUACA CAGCUCACGAGUGCCUGCUGGGGUGGAACCUGGUC UGUCU | 302 |
| miR-371 | GUGGCACUCAAACUGUGGGGGCACUUUCUGCUCUC UGGUGAAAGUGCCGCCAUCUUUUGAGUGUUAC | 303 |
| miR-372 | GUGGGCCUCAAAUGUGGAGCACUAUUCUGAUGUCC AAGUGGAAAGUGCUGCGACAUUUGAGCGUCAC | 304 |
| miR-373 | GGGAUACUCAAAAUGGGGCGCUUUCCUUUUUGUC UGUACUGGGAAGUGCUUCGAUUUUGGGGUGUCCC | 305 |
| miR-374 | UACAUCGGCCAUUAUAAUACAACCUGAUAAGUGUU AUAGCACUUAUCAGAUUGUAUUGUAAUUGUCUGUG UA | 306 |
| miR-hes1 | AUGGAGCUGCUCACCCUGUGGGCCUCAAAUGUGGA GGAACUAUUCUGAUGUCCAAGUGGAAAGUGCUGCG ACAUUUGAGCGUCACCGGUGACGCCCAUAUCA | 307 |
| miR-hes2 | GCAUCCCCUCAGCCUGUGGCACUCAAACUGUGGGGG CACUUUCUGCUCUCUGGUGAAAGUGCCGCCAUCUU UUGAGUGUUACCGCUUGAGAAGACUCAACC | 308 |
| miR-hes3 | CGAGGAGCUCAUACUGGGAUACUCAAAAUGGGGGC GCUUUCCUUUUUGUCUGUUACUGGGAAGUGCUUCG AUUUUGGGGUGUCCCUGUUUUGAGUAGGGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | ugagguaguagguuguauaguu | 310 | let-7a-1; let-7a-2; let-7a-3; let-7a-4 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7b | ugagguaguagguugugugguu | 311 | let-7b |
| let-7c | ugagguaguagguuguaugguu | 312 | let-7c |
| let-7d | agagguaguagguugcauagu | 313 | let-7d; let-7d-v1 |
| let-7e | ugagguaggagguuguauagu | 314 | let-7e |
| let-7f | ugagguaguagauuguauaguu | 315 | let-7f-1; let-7f-2-1; let-7f-2-2 |
| let-7g | ugagguaguaguuuguacagu | 316 | let-7g |
| let-7i | ugagguaguaguuugugcu | 317 | let-7i |
| miR-1 | uggaauguaaagaaguaugua | 318 | miR-1b; miR-1b-1, miR-1b-2 |
| miR-7 | uggaagacuagugauuuuguu | 319 | miR-7-1; miR-7-1a; miR-7-2; miR-7-3 |
| miR-9 | ucuuugguuaucuagcuguauga | 320 | miR-9-1; miR-9-2, miR-9-3 |
| miR-9* | uaaagcuagauaaccgaaagu | 321 | miR-9-1; miR-9-2; miR-9-3 |
| miR-10a | uacccuguagauccgaauuugug | 322 | miR-10a |
| miR-10b | uacccuguagaaccgaauuugu | 323 | miR-10b |
| miR-15a | uagcagcacauaaugguuugug | 324 | miR-15a; miR-15a-2 |
| miR-15b | uagcagcacaucaugguuuaca | 325 | miR-15b |
| miR-16 | uagcagcacguaaauauuggcg | 326 | miR-16-1; miR-16-2; miR-16-13 |
| miR-17-5p | caaagugcuuacagugcagguagu | 327 | miR-17 |
| miR-17-3p | acugcagugaaggcacuugu | 328 | miR-17 |
| miR-18 | uaaggugcaucuagugcagaua | 329 | miR-18; miR-18-13 |
| miR-19a | ugugcaaaucuaugcaaaacuga | 330 | miR-19a; miR-19a-13 |
| miR-19b | ugugcaaauccaugcaaaacuga | 331 | miR-19b-1; miR-19b-2 |
| miR-20 | uaaagugcuuauagugcaggua | 332 | miR-20 (miR-20a) |
| miR-21 | uagcuuaucagacugauguuga | 333 | miR-21; miR-21-17 |
| miR-22 | aagcugccaguugaagaacugu | 334 | miR-22 |
| miR-23a | aucacauugccagggauuucc | 335 | miR-23a |
| miR-23b | aucacauugccagggauuaccac | 336 | miR-23b |
| miR-24 | uggcucaguucagcaggaacag | 337 | miR-24-1; miR-24-2; miR-24-19; miR-24-9 |
| miR-25 | cauugcacuugucucggucuga | 338 | miR-25 |
| miR-26a | uucaaguaauccaggauaggcu | 339 | miR-26a; miR-26a-1; miR-26a-2 |
| miR-26b | uucaaguaauucaggauaggu | 340 | miR-26b |
| miR-27a | uucacaguggcuaaguuccgcc | 341 | miR-27a |
| miR-27b | uucacaguggcuaaguucug | 342 | miR-27b-1; miR-27b-2 |
| miR-28 | aaggagcucacagucuauugag | 343 | miR-28 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-29a | cuagcaccaucugaaaucgguu | 344 | miR-29a-2; miR-29a |
| miR-29b | uagcaccauuugaaaucagu | 345 | miR-29b-1; miR-29b-2 |
| miR-29c | uagcaccauuugaaaucgguua | 346 | miR-29c |
| miR-30a-5p | uguaaacauccucgacuggaagc | 347 | miR-30a |
| miR-30a-3p | cuuucagucggauguuugcagc | 348 | miR-30a |
| miR-30b | uguaaacauccuacacucagc | 349 | miR-30b-1; miR-30b-2 |
| miR-30c | uguaaacauccuacacucucagc | 350 | miR-30c |
| miR-30d | uguaaacauccccgacuggaag | 351 | miR-30d |
| miR-30e | uguaaacauccuugacugga | 352 | miR-30e |
| miR-31 | ggcaagaugcuggcauagcug | 353 | miR-31 |
| miR-32 | uauugcacauuacuaaguugc | 354 | miR-32 |
| miR-33 | gugcauuguaguugcauug | 355 | miR-33; miR-33b |
| miR-34a | uggcagugucuuagcugguugu | 356 | miR-34a |
| miR-34b | aggcagugucauuagcugauug | 357 | miR-34b |
| miR-34c | aggcaguguaguuagcugauug | 358 | miR-34c |
| miR-92 | uauugcacuugucccggccugu | 359 | miR-92-2; miR-92-1 |
| miR-93 | aaagugcuguucgugcagguag | 360 | miR-93-1; miR-93-2 |
| miR-95 | uucaacgguauuuauugagca | 361 | miR-95 |
| miR-96 | uuuggcacuagcacauuuuugc | 362 | miR-96 |
| miR-98 | ugagguaguaaguuguauuguu | 363 | miR-98 |
| miR-99a | aacccguagauccgaucuugug | 364 | miR-99a |
| miR-99b | cacccguagaaccgaccuugcg | 365 | miR-99b |
| miR-100 | uacaguacugugauaacugaag | 366 | miR-100 |
| miR-101 | uacaguacugugauaacugaag | 367 | miR-101-1; miR-101-2 |
| miR-103 | agcagcauuguacagggcuauga | 368 | miR-103-1 |
| miR-105 | ucaaaugcucagacuccugu | 369 | miR-105 |
| miR-106-a | aaaagugcuuacagugcagguagc | 370 | miR-106-a |
| miR-106-b | uaaagugcugacagugcagau | 371 | miR-106-b |
| miR-107 | agcagcauuguacagggcuauca | 372 | miR-107 |
| miR-122a | uggagugugacaauggguguuugu | 373 | miR-122a-1; miR-122a-2 |
| miR-124a | uuaaggcacgcggugaaugcca | 374 | miR-124a-1; miR-124a-2; miR-124a-3 |
| miR-125a | ucccugagacccuuuaaccugug | 375 | miR-125a-1; miR-125a-2 |
| miR-125b | ucccugagacccuaacuuguga | 376 | miR-125b-1; miR-125b-2 |
| miR-126* | cauuauuacuuuugguacgcg | 377 | miR-126-1; miR-126-2 |
| miR-126 | ucguaccgugaguaauaaugc | 378 | miR-126-1; miR-126-2 |
| miR-127 | ucggauccgucugagcuuggcu | 379 | miR-127-1; miR-127-2 |
| miR-128a | ucacagugaaccggucucuuuu | 380 | miR-128; miR-128a |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-128b | ucacagugaaccggucucuuuc | 381 | miR-128b |
| miR-129 | cuuuuugcggucugggcuugc | 382 | miR-129-1; miR-129-2 |
| miR-130a | cagugcaauguuaaaagggc | 383 | miR-130a |
| miR-130b | cagugcaaugaugaaagggcau | 384 | miR-130b |
| miR-132 | uaacagucuacagccauggucg | 385 | miR-132-1 |
| miR-133a | uugguccccuucaaccagcugu | 386 | miR-133a-1; miR-133a-2 |
| miR-133b | uugguccccuucaaccagcua | 387 | miR-133b |
| miR-134 | ugugacugguugaccagaggg | 388 | miR-134-1; miR-134-2 |
| miR-135a | uauggcuuuuuauuccuauguga | 389 | miR-135a; miR-135a-2 (miR-135-2) |
| miR-135b | uauggcuuuucauuccuaugug | 390 | miR-135b |
| miR-136 | acuccauuuguuuugaugaugga | 391 | miR-136-1; miR-136-2 |
| miR-137 | uauugcuuaagaauacgcguag | 392 | miR-137 |
| miR-138 | agcuggguugugaauc | 393 | miR-138-1; miR-138-2 |
| miR-139 | ucuacagugcacgugucu | 394 | miR-139 |
| miR-140 | agugguuuuacccuaughguag | 395 | miR-140; miR-140as; miR-140s |
| miR-141 | aacacugucugguaaagaugg | 396 | miR-141-1; miR-141-2 |
| miR-142-3p | uguaguguuuccuacuuuaugga | 397 | miR-142 |
| miR-142-5p | cauaaaguagaaagcacuac | 398 | miR-142 |
| miR-143 | ugagaugaagcacuguagcuca | 399 | miR-143-1 |
| miR-144 | uacaguauagaugauguacuag | 400 | miR-144-1; miR-144-2 |
| miR-145 | guccaguuuucccaggaaucccuu | 401 | miR-145-1; miR-145-2 |
| miR-146 | ugagaacugaauuccauggguu | 402 | miR-146-1; miR-146-2 |
| miR-147 | guguguggaaaugcuucugc | 403 | miR-147 |
| miR-148a | ucagugcacuacagaacuuugu | 404 | miR-148a (miR-148) |
| miR-148b | ucagugcaucacagaacuuugu | 405 | miR-148b |
| miR-149 | ucuggcuccgugucuucacucc | 406 | miR-149 |
| miR-150 | ucucccaacccuuguaccagug | 407 | miR-150-1; miR-150-2 |
| miR-151 | acuagacugaagcuccuugagg | 408 | miR-151 |
| miR-152 | ucagugcaugacagaacuugg | 409 | miR-152-1; miR-152-2 |
| miR-153 | uugcauagucacaaaaguga | 410 | miR-153-1-1; miR-153-1-2; miR-153-2-1; miR-153-2-2 |
| miR-154 | uagguuauccguguugccuucg | 411 | miR-154-1; miR-154-2 |
| miR-154* | aaucauacacgguugaccuauu | 412 | miR-154-1; miR-154-2 |
| miR-155 | uuaaugcuaaucgugauagggg | 413 | miR-155 |
| miR-181a | aacauucaacgcugucggugagu | 414 | miR-181a |
| miR-181b | aacauucauugcugucgguggguu | 415 | miR-181b-1; miR-181b-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-181c | aacauucaaccugucgugagu | 416 | miR-181c |
| miR-182 | uuuggcaaugguagaacucaca | 417 | miR-182; miR-182as |
| miR-182* | ugguucuagacuugccaacua | 418 | miR-182; miR-182as |
| miR-183 | uauggcacugguagaauucacug | 419 | miR-183 |
| miR-184 | uggacggagaacugauaagggu | 420 | miR-184-1; miR-184-2 |
| miR-185 | uggagagaaaggcaguuc | 421 | miR-185-1; miR-185-2 |
| miR-186 | caaagaauucuccuuuugggcuu | 422 | miR-186-1; miR-186-2 |
| miR-187 | ucgugucuuguguugcagccg | 423 | miR-187 |
| miR-188 | caucccuugcaugguggagggu | 424 | miR-188 |
| miR-189 | gugccuacugagcugauaucagu | 425 | miR-189-1; miR-189-2 |
| miR-190 | ugauauguuugauauauuaggu | 426 | miR-190-1; miR-190-2 |
| miR-191 | caacggaaucccaaaagcagcu | 427 | miR-191-1; miR-191-2 |
| miR-192 | cugaccuaugaauugacagcc | 428 | miR-192 |
| miR-193 | aacuggccuacaaaguccag | 429 | miR-193-1; miR-193-2 |
| miR-194 | uguaacagcaacuccaugugga | 430 | miR-194-1; miR-194-2 |
| miR-195 | uagcagcacagaaauauuggc | 431 | miR-195-1; miR-195-2 |
| miR-196a | uagguaguuucauguuguugg | 432 | miR-196a; miR196a-2 (miR196-2) |
| miR-196b | uagguaguuuccuguuguugg | 433 | miR-196b |
| miR-197 | uucaccaccuucuccacccagc | 434 | miR-197 |
| miR-198 | gguccagaggggagauagg | 435 | miR-198 |
| miR-199a | cccaguguucagacuaccuguuc | 436 | miR-199a-1; miR-199a-2 |
| miR-199a* | uacaguagucugcacauugguu | 437 | miR-199a-1; miR-199a-2; miR-199s; miR-199b |
| miR-199b | cccaguguuuagacuaucuguuc | 438 | miR-199b |
| miR-200a | uaacacugucugguaacgaugu | 439 | miR-200a |
| miR-200b | cucuaauacugccugguaaugaug | 440 | miR-200b |
| miR-200c | aauacugccggguaaugaugga | 441 | miR-200c |
| miR-202 | agagguauagggcaugggaaga | 442 | miR-202 |
| miR-203 | gugaaauguuuaggaccacuag | 443 | miR-203 |
| miR-204 | uucccuuugucauccuaugccu | 444 | miR-204 |
| miR-205 | uccuucauuccaccggagucug | 445 | miR-205 |
| miR-206 | uggaauguaaggaagugugugg | 446 | miR-206-1; miR-206-2 |
| miR-208 | auaagacgagcaaaaagcuugu | 447 | miR-208 |
| miR-210 | cugugcgugugacagcggcug | 448 | miR-210 |
| miR-211 | uucccuuugucauccuucgccu | 449 | miR-211 |
| miR-212 | uaacagucuccagucacggcc | 450 | miR-212 |
| miR-213 | accaucgaccguugauuguacc | 451 | miR-213 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-214 | acagcaggcacagacaggcag | 452 | miR-214 |
| miR-215 | augaccaugaauugacagac | 453 | miR-215 |
| miR-216 | uaaucucagcuggcaacugug | 454 | miR-216 |
| miR-217 | uacugcaucaggaacugauuggau | 455 | miR-217 |
| miR-218 | uugugcuugaucuaaccaugu | 456 | miR-218-1; miR-218-2 |
| miR-219 | ugauuguccaaacgcaauucu | 457 | miR-219; miR-219-1; miR-219-2 |
| miR-220 | ccacaccguaucugacacuuu | 458 | miR-220 |
| miR-221 | agcuacauugucugcugdgguuuc | 459 | miR-221 |
| miR-222 | agcuacaucuggcuacuggducuc | 460 | miR-222 |
| miR-223 | ugucaguuugucaaauacccc | 461 | miR-223 |
| miR-224 | caagucacuaguguuccguuua | 462 | miR-224 |
| miR-296 | agggccccccucaauccugu | 463 | miR-296 |
| miR-299 | ugguuuaccgucccacauacau | 464 | miR-299 |
| miR-301 | cagugcaauaguauugucaaagc | 465 | miR-301 |
| miR-302a | uaagugcuuccauguuuugguga | 466 | miR-302a |
| miR-302b* | acuuuaacauggaagugcuuucu | 467 | miR-302b |
| miR-302b | uaagugcuuccauguuuuaguag | 468 | miR-302b |
| miR-302c* | uuuaacaugggdgguaccugcug | 469 | miR-302c |
| miR-302c | uaagugcuuccauguuucagugg | 470 | miR-302c |
| miR-302d | uaagugcuuccauguuugagugu | 471 | miR-302d |
| miR-320 | aaaagcugggduugagagggcgaa | 472 | miR-320 |
| miR-321 | uaagccagggauugugdgguuc | 473 | miR-321 |
| miR-323 | gcacauuacacggucgaccucu | 474 | miR-323 |
| miR-324-5p | cgaucccuagggcauuggugu | 475 | miR-324 |
| miR-324-3p | ccacugccccaggugcugcugg | 476 | miR-324 |
| miR-325 | ccuaguagguguccaguaagu | 477 | miR-325 |
| miR-326 | ccucugggcccuucccuccag | 478 | miR-326 |
| miR-328 | cuggcccucucugcccuuccgu | 479 | miR-328 |
| miR-330 | gcaaagcacacggccugcagaga | 480 | miR-330 |
| miR-331 | gccccugggccuauccuagaa | 481 | miR-331 |
| miR-335 | ucaagagcaauaacgaaaaaugu | 482 | miR-335 |
| miR-337 | uccagcuccuauaugaugccuuu | 483 | miR-337 |
| miR-338 | uccagcaucagugauuuuguuga | 484 | miR-338 |
| miR-339 | ucccuguccuccaggagcuca | 485 | miR-339 |
| miR-340 | uccgucucaguuacuuuauagcc | 486 | miR-340 |
| miR-342 | ucucacacagaaaucgcacccguc | 487 | miR-342 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-345 | ugcugacuccuaguccagggc | 488 | miR-345 |
| miR-346 | ugucugcccgcaugccugccucu | 489 | miR-346 |
| miR-367 | aauugcacuuuagcaaugguga | 490 | miR-367 |
| miR-368 | acauagaggaaauuccacguuu | 491 | miR-368 |
| miR-369 | aauaauacaugguugaucuuu | 492 | miR-369 |
| miR-370 | gccugcugggguggaaccugg | 493 | miR-370 |
| miR-371 | gugccgccaucuuuugagugu | 494 | miR-371 |
| miR-372 | aaagugcugcgacauuugagcgu | 495 | miR-372 |
| miR-373* | acucaaaauggggcgcuuucc | 496 | miR-373 |
| miR-373 | gaagugcuucgauuuugggugu | 497 | miR-373 |
| miR-374 | uuauaauacaaccugauaagug | 498 | miR-374 |

The level of at least one miR gene product can be measured in cells of a biological sample obtained from the subject. For example, a tissue sample can be removed from a subject suspected of having pancreatic cancer by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "upregulated"). As used herein, expression of a miR gene product is "upregulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "downregulated"). As used herein, expression of a miR gene is "downregulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of pancreatic cancer in the subject. In one embodiment, the level of the at least one miR gene product in the test sample is greater than the level of the corresponding miR gene product in the control sample. miR gene products having higher expression levels in pancreatic cancer than normal pancreatic tissue are described herein (see, e.g., Exemplification). In one embodiment, the at least one miR gene product is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In another embodiment, the at least one miR gene product is selected from the group consisting of miR-103, miR-107 and a combination thereof. In yet another embodiment, the at least one miR gene product is selected from the group consisting of miR-23a, miR-26b, miR-192, miR-342 and a combination thereof.

In one embodiment, the level of the at least one miR gene product in the test sample is less than the level of the corresponding miR gene product in the control sample. miR gene products having lower expression levels in pancreatic cancer than normal pancreatic tissue are described herein (see, e.g., Exemplification). In one embodiment, the at least one miR gene product is selected from the group consisting of miR-326, miR-155, miR-339, miR-34c, miR-345, miR-152, miR-372, miR-128a and a combination thereof. In another embodiment, the at least one miR gene product is miR-155.

In one embodiment, the at least one miR gene product is selected from the group consisting of miR-103, is miR-107, miR-155 and a combination thereof. In another embodiment, the at least one miR gene product is miR-103, which is upregulated in the test sample, as compared to the control sample. In yet another embodiment, the at least one miR gene product is miR-107, which is upregulated in the test sample, as compared to the control sample. In still another embodiment, the at least one miR gene product is miR-155, which is downregulated in the test sample, as compared to the control sample. In a particular embodiment, all three of these miRs (miR-103, miR-107 and miR-155) are compared to the corresponding miRs in the control sample. As described and exemplified herein, the expression of miR-103 and miR-107, associated with lack of expression of miR-155, discriminates pancreatic tumors from normal pancreas.

In one embodiment, the pancreatic cancer that is diagnosed is a pancreatic endocrine tumor (PET). In another embodiment, the pancreatic cancer that is diagnosed is a pancreatic exocrine tumor (e.g., an adenocarcinoma). In yet another embodiment, the pancreatic cancer that is diagnosed is selected from the group consisting of a pancreatic endocrine tumor (PET) and a pancreatic exocrine tumor (e.g., an adenocarcinoma). In a particular embodiment, the pancreatic cancer that is diagnosed is selected from the group consisting of an acinar cell carcinoma (PACC) and an insulinoma. In yet another embodiment, the pancreatic cancer that is diagnosed is selected from the group consisting of a pancreatic endocrine tumor (PET), a pancreatic acinar cell carcinoma (PACC) and an insulinoma. In still another embodiment, the diagnostic method can be used to diagnose any type of pancreatic cancer.

In one embodiment, the invention is a method of diagnosing whether a subject has, or is at risk for developing, pancreatic acinar cell carcinoma (PACC). In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, PACC. In one embodiment, the level of the at least one miR gene product in the test sample is greater than the level of the corresponding miR gene product in the control sample. In another embodiment, the at least one miR gene product that is upregulated is selected from the group consisting of miR-103-2, miR-25, miR-200c, miR-335, miR-21, miR-103-1, miR-92-1, miR-181b-2, miR-191, miR-93, miR-26a-1, miR-17, miR-20, miR-107, miR-26b, miR-215, miR-92-2, miR-192, miR-342, miR-100, miR-3p21-v, miR-106a, miR-15a, miR-23a, miR-181b-1, miR-128b, miR-106b, miR-194-1, miR-219-1, miR-242 and a combination thereof. In yet another embodiment, the level of the at least one miR gene product in the test sample is less than the level of the corresponding miR gene product in the control sample. In still another embodiment, the at least one miR gene product that is downregulated is selected from the group consisting of miR-218-2, miR-339, miR-326, miR-34c, miR-152, miR-138-2, miR-128a and a combination thereof.

In one embodiment, the invention is a method of diagnosing the type of pancreatic cancer that a subject has. In this method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the type of pancreatic cancer.

In a particular embodiment, the type of pancreatic cancer that is diagnosed is selected from the group consisting of a pancreatic endocrine tumor (PET) and a pancreatic acinar cell carcinoma (PACC). In another embodiment, the level of the at least one miR gene product in the test sample is greater than the level of the corresponding miR gene product in the control sample. In another embodiment, the type of pancreatic cancer is a pancreatic endocrine tumor (PET) and the at least one miR gene product that is upregulated is selected from the group consisting of miR-125a, miR-99a, miR-99b, miR-125b-1, miR-342, miR-130a, miR-100, miR-132, miR-129-2, miR-125b-2 and a combination thereof. In yet another embodiment, the level of the at least one miR gene product in the test sample is less than the level of the corresponding miR gene product in the control sample. In still another embodiment, the type of pancreatic cancer is a pancreatic acinar cell carcinoma (PACC) and the at least one miR gene product that is downregulated is selected from the group consisting of miR-125a, miR-99a, miR-99b, miR-125b-1, miR-342, miR-130a, miR-100, miR-132, miR-129-2, miR-125b-2 and a combination thereof. As described herein, the expression of particular miR gene products can distinguish between PET and PACC (see, e.g., Exemplification).

In one embodiment, the type of pancreatic cancer that is diagnosed is selected from the group consisting of a well-differentiated endocrine carcinoma (WDEC) and a pancreatic acinar cell carcinoma (PACC). In another embodiment, the level of the at least one miR gene product in the test sample is greater than the level of the corresponding miR gene product in the control sample. In yet another embodiment, the type of pancreatic cancer is a well-differentiated endocrine carcinoma (WDEC) and the at least one miR gene product that is upregulated is selected from the group consisting of miR-125a, miR-99a, miR-132 and a combination thereof. In another embodiment, the level of the at least one miR gene product in the test sample is less than the level of the corresponding miR gene product in the control sample. In still another embodiment, the type of pancreatic cancer is a well-differentiated endocrine carcinoma (WDEC) and the at least one miR gene product that is down-regulated is miR-148a. As described herein, the expression of particular miR gene products can distinguish between WDEC and PACC (see, e.g., Exemplification).

In one embodiment, the type of pancreatic cancer that is diagnosed is selected from the group consisting of an insulinoma and a non-functioning pancreatic endocrine tumor (NF-PET). In one embodiment, the level of the at least one miR gene product in the test sample is greater than the level of the corresponding miR gene product in the control sample. In another embodiment, the type of pancreatic cancer is an insulinoma and the at least one miR gene product that is upregulated is selected from the group consisting of miR-204, miR-203, miR-211 and a combination thereof. As described herein, the expression of particular miR gene products can distinguish between WDEC and PACC (see, e.g., Exemplification).

The invention also provides methods of determining the prognosis of a subject with pancreatic cancer. In this method, the level of at least one miR gene product, which is associated with a particular prognosis in pancreatic cancer (e.g., a good or positive prognosis, a poor or adverse prognosis), is measured in a test sample from the subject. An alteration (e.g., an increase, a decrease) in the level of the miR gene product in the test sample, relative to the level of a corresponding miR gene product in a control sample, is indicative of the subject having a pancreatic cancer with a particular prognosis. In one embodiment, the miR gene product is associated with an adverse (i.e., poor) prognosis. Examples of an adverse prognosis include, but are not limited to, low survival rate and rapid disease progression. In one embodiment, the level of the at least one miR gene product in the test sample is greater than the level of the corresponding miR gene product in a control sample. In another embodiment, the at least one miR gene product that is upregulated, and which is measured, is miR-21. In yet another embodiment, the pancreatic cancer is associated with metastasis and/or a high proliferation index. As described herein, the expression of particular miR gene products, which are associated with an adverse prognosis in pancreatic cancer, can prognosticate the severity of a subject's pancreatic cancer (see, e.g., Exemplification). In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

In one embodiment, the invention is a method of determining whether a pancreatic cancer in a subject is metastatic. As described herein, most PET-related deaths are caused by liver metastasis. Thus, identification of metastatic pancreatic cancer can aid in determining appropriate treatment options. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of metastasis. In one embodiment, the level of the at least one miR gene product in the test sample is greater than the level of the corresponding miR gene product in the control sample. In another embodiment, the at least one miR gene product that is upregulated is miR-21.

In one embodiment, the invention is a method of determining whether a pancreatic cancer in a subject has a high proliferation index. As is known, pancreatic cancers having a high proliferation index have an adverse prognosis and, therefore, identification of pancreatic cancers having a high proliferation index can also aid in determining appropriate treatment options. In this method, the level of at least one miR gene product is measured in a test sample (e.g., a pancreatic cancer sample) from the subject. An alteration (e.g., an increase, a decrease) in the level of the miR gene product in the test sample, relative to the level of a corresponding miR gene product in a control sample, is indicative of a high proliferation index. In one embodiment, the level of the at least one miR gene product in the test sample is greater than the level of the corresponding miR gene product in the control sample. In another embodiment, the at least one miR gene product that is upregulated is miR-21.

Identification of targets of particular miR gene products (e.g., those miR gene products exhibiting upregulated or downregulated expression relative to a control sample) can aid in elucidating mechanisms of action of microRNAs. As exemplified herein, particular putative targets of select microRNAs, namely miR-103/miR-107, miR-155, miR-204/miR-211 and miR-21, were identified. Analysis revealed numerous upregulated (28 target genes) and downregulated (7 target genes) target genes of particular microRNAs in pancreatic cancer samples. As described in Table 10, 28 upregulated target genes and 7 downregulated target genes of miR-103/miR-107 were identified in pancreatic cancer samples (Exemplification and Table 10). In addition, 2 upregulated target genes and 2 downregulated target genes of miR-103/miR-107, and 1 upregulated target gene and 1 downregulated target gene of miR-21 were identified in pancreatic cancer samples (Exemplification and Table 10). Thus, in one embodiment, expression of target genes of particular microRNAs (e.g., those listed in Table 10) can be used to diagnose cancer (e.g., pancreatic cancer). One of skill in the art can measure the expression levels of any of these target genes using known methods and/or methods described herein for measuring the expression levels of microRNAs (e.g., quantitative or semi-quantitative RT-PCR, Northern blot analysis, solution hybridization detection, microarray analysis), without undue experimentation. In one embodiment, the target gene that is measured is Programmed Cell Death 4 (PDCD4).

In one embodiment, the invention is a method of determining the prognosis of a subject with pancreatic cancer. In this method, the level of PDCD4 is measured in a test sample (e.g., a pancreatic cancer sample) from the subject. An alteration (e.g., an increase, a decrease) in the level of PDCD4 in the test sample, relative to the level of PDCD4 in a control sample, is indicative of an adverse prognosis. In one embodiment, the level of PDCD4 in the test sample is less than the level of PDCD4 in the control sample. In another embodiment, the pancreatic cancer is associated with metastasis and/or a high proliferation index.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, pancreatic cancer. In one embodiment, the signal of at least one miRNA is upregulated, relative to the signal generated from the control sample. In another embodiment, the signal of at least one miRNA is downregulated, relative to the signal generated from the control sample. In a particular embodiment, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of miR-103-2, miR-107, miR-103-1, miR-342, miR-100, miR-24-2, miR-23a, miR-125a, miR-26a-1, miR-24-1, miR-191, miR- 15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375, miR-326, miR-155, miR-339, miR-34c, miR-345, miR-152, miR-372, miR-128a and a combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., pancreatic cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of diagnosing whether a subject has, or is at risk for developing, a pancreatic cancer with an adverse prognosis. In this method, the level of at least one miR gene product, which is associated with an adverse prognosis in pancreatic cancer, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a pancreatic cancer with an adverse prognosis. In one embodiment, an alteration in the signal of miR-21 is indicative of the subject either having, or being at risk for developing, a pancreatic cancer with an adverse prognosis.

In particular embodiments of the diagnostic, prognostic and therapeutic methods of the invention, the miR gene product is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described herein, the level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in Table 1a and Table 1b and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer (e.g., pancreatic cancer). Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microR- NAs have an altered expression level in pancreatic cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from pancreatic cancer tissue, and within pancreatic cancer tissue, different prognosis states (for example, good or poor long term survival prospects) may be determined. By comparing expression profiles of pancreatic cancer tissue in different states, information regarding which genes are important (including both upregulation and downregulation of genes) in each of these states is obtained. The identification of sequences that are differentially expressed in pancreatic cancer tissue or normal pancreatic tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the pancreatic cancer expression profile or convert a poor prognosis profile to a better prognosis profile.

Without wishing to be bound by any one theory, it is believed that alterations in the level of one or more miR gene products in cells can result in the deregulation of one or more intended targets for these miRs, which can lead to the formation of pancreatic cancer. Therefore, altering the level of the miR gene product (e.g., by decreasing the level of a miR that is upregulated in pancreatic cancer cells, by increasing the level of a miR that is downregulated in pancreatic cancer cells) may successfully treat the pancreatic cancer.

Accordingly, the present invention encompasses methods of treating pancreatic cancer in a subject, wherein at least one miR gene product is deregulated (e.g., downregulated, upregulated) in the cells (e.g., pancreatic cancer cells) of the subject. In one embodiment, the level of at least one miR gene product in a test sample (e.g., a pancreatic cancer sample) is greater than the level of the corresponding miR gene product in a control sample. In another embodiment, the level of at least one miR gene product in a test sample (e.g., a pancreatic cancer sample is less than the level of the corresponding miR gene product in a control sample. When the at least one isolated miR gene product is downregulated in the pancreatic cancer cells, the method comprises administering an effective amount of the at least one isolated miR gene product, or an isolated variant or biologically-active fragment thereof, such that proliferation of cancer cells in the subject is inhibited. For example, when a miR gene product is downregulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in Table 1a or Table 1b) that is downregulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with pancreatic cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with pancreatic cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is upregulated in the cancer cells, the method comprises administering to the subject an effective amount of a compound that inhibits expression of the at least one miR gene product, such that proliferation of pancreatic cancer cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

In a certain embodiment, the isolated miR gene product that is deregulated in pancreatic cancer (and which is administered to the subject) is selected from the group consisting of miR-326, miR-155, miR-339, miR-34c, miR-345, miR-152, miR-372, miR-128a and a combination thereof (or an isolated variant or biologically-active fragment of one or more of these miRs). In a particular embodiment, the miR gene product that is administered is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described, when the at least one isolated miR gene product is upregulated in cancer cells, the method comprises administering to the subject an effective amount of at least one compound for inhibiting expression of the at least one miR gene product, such that proliferation of pancreatic cancer cells is inhibited. In one embodiment, the compound for inhibiting expression of the at least one miR gene product inhibits a miR gene product selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof.

In a related embodiment, the methods of treating pancreatic cancer in a subject additionally comprise the step of first determining the amount of at least one miR gene product in pancreatic cancer cells from the subject, and comparing that level of the miR gene product to the level of a corresponding miR gene product in control cells. If expression of the miR gene product is deregulated (e.g., downregulated, upregulated) in pancreatic cancer cells, the methods further comprise altering the amount of the at least one miR gene product expressed in the pancreatic cancer cells. In one embodiment, the amount of the miR gene product expressed in the cancer cells is less than the amount of the miR gene product expressed in control cells, and an effective amount of the miR gene product, or an isolated variant or biologically-active fragment thereof, is administered to the subject. In another embodiment, the amount of the miR gene product expressed in the cancer cells is greater than the amount of the miR gene product expressed in control cells, and an effective amount of at least one compound for inhibiting expression of the at least one miR gene is administered to the subject. Suitable miRs and compounds that inhibit expression of miR genes include, for example, those described herein.

The terms "treat", "treating" and "treatment", as used herein, refer to ameliorating symptoms associated with a disease or condition, for example, pancreatic cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from pancreatic cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating pancreatic cancer in a subject (e.g., a human). Isolated miR gene products can be obtained using a number of standard techniques.

For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. Nos. 5,252,479; 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., pancreatic cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in Table 1a and Table 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), Science 261:1004 and U.S. Pat. No. 5,849,902 to Woolf et al., the entire disclosures of which are incorporated herein by reference. Expression of a given miR gene can also be inhibited by an enzymatic nucleic acid.

As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucleic Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., pancreatic cancer). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Minis Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells.

Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating pancreatic cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in pancreatic cancer cells relative to suitable control cells (i.e., it is downregulated). In a certain embodiment, the isolated miR gene product is selected from the group consisting of miR-326, miR-155, miR-339, miR-34c, miR-345, miR-152, miR-372, miR-128a and a combination thereof. In one embodiment, the isolated miR gene product is not miR-15a or miR-16-1. In an additional embodiment, the miR gene product is not miR-210 or miR-212. In another embodiment, the miR gene product is not miR-21, miR-143, miR-205 or miR-9. In yet another embodiment, the miR gene product is not miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9.

In other embodiments, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in pancreatic cancer cells than control cells (i.e., it is upregulated). In certain embodiments, the miR expression-inhibition compound is specific for one or more miR gene products selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In one embodiment, the isolated miR gene product is not specific for miR-15a or miR-16-1. In another embodiment, the miR gene product is not specific for miR-210 or miR-212. In yet another embodiment, the miR gene product is not specific for miR-21, miR-143, miR-205 or miR-9. In still another embodiment, the miR gene product is not specific for miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-pancreatic cancer agent, comprising providing a test agent to a cell and measuring the level of at least one miR gene product in the cell. In one embodiment, the method comprises providing a test agent to a cell and measuring the level of at least one miR gene product associated with decreased expression levels in pancreatic cancer cells. An increase in the level of the miR gene product in the cell, relative to a to a suitable control (e.g., the level of the miR gene product in a control cell), is indicative of the test agent being an anti-pancreatic cancer agent. In a particular embodiment, the at least one miR gene product associated with decreased expression levels in pancreatic cancer cells is selected from the group consisting of miR-326, miR-155, miR-339, miR-34c, miR-345, miR-152, miR-372, miR-128a and a combination thereof. In one embodiment, the miR gene product is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR- 146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

In other embodiments, the method comprises providing a test agent to a cell and measuring the level of at least one miR gene product associated with increased expression levels in pancreatic cancer cells. A decrease in the level of the miR gene product associated with increased expression levels in pancreatic cancer in the cell, relative to a suitable control (e.g., the level of the miR gene product in a control cell), is indicative of the test agent being an anti-pancreatic cancer agent. In a particular embodiment, the at least one miR gene product associated with increased expression levels in pancreatic cancer cells is selected from the group consisting of miR-103-2, miR-107, miR-103-1, miR-342, miR-100, miR-24-2, miR-23a, miR-125a, miR-26a-1, miR-24-1, miR-191, miR-15a, miR-368, miR-26b, miR-125b-2, miR-125b-1, miR-26a-2, miR-335, miR-126, miR-1-2, miR-21, miR-25, miR-92-2, miR-130a, miR-93, miR-16-1, miR-145, miR-17, miR-99b, miR-181b-1, miR-146, miR-181b-2, miR-16-2, miR-99a, miR-197, miR-10a, miR-224, miR-92-1, miR-27a, miR-221, miR-320, miR-7-1, miR-29b-2, miR-150, miR-30d, miR-29a, miR-23b, miR-135a-2, miR-223, miR-3p21-v, miR-128b, miR-30b, miR-29b-1, miR-106b, miR-132, miR-214, miR-7-3, miR-29c, miR-367, miR-30c-2, miR-27b, miR-140, miR-10b, miR-20, miR-129-1, miR-340, miR-30a, miR-30c-1, miR-106a, miR-32, miR-95, miR-222, miR-30e, miR-129-2, miR-345, miR-143, miR-182, miR-1-1, miR-133a-1, miR-200c, miR-194-1, miR-210, miR-181c, miR-192, miR-220, miR-213, miR-323, miR-375 and a combination thereof. In one embodiment, the miR gene product is not one or more of let7a-2, let-7c, let-7g, let-71, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

EXEMPLIFICATION

Materials and Methods

Patient Data, Neoplastic-Cell Enrichment and RNA Extraction.

The clinicopathological characteristics of 40 PET and four PACC, retrieved from the frozen tissue bank of the Pathology Department of the University of Verona, Italy, are reported in Table 2. All tumors were sporadic, as assessed by personal and family histories obtained by direct interview of patients. PET were diagnosed by histopathologic and cell marker analysis, and classified according to WHO criteria (Kloppel, G., et al., "The Gastroenteropancreatic Neuroendocrine Cell System and Its Tumors: The WHO Classification." *Ann. N. Y. Acad. Sci.* 1014:13-27 (2004)). They included 28 nonfunctional and 12 functional tumors. The 28 NF-PET included 11 well-differentiated endocrine tumors (WDET) and 18 well differentiated endocrine carcinomas (WDEC). The 12 F-PET were insulinomas, comprising 11 WDET and 1 WDEC. WDET were considered with either benign or uncertain biological behavior in accordance with the WHO criteria, that considers tumor size, Ki-67 proliferation index and vascular invasion (Table 2). Diagnosis of PACC was confirmed by immunohistochemical expression of lipase, amylase and trypsin in neoplastic cells. As a control, normal pancreas was taken in 12 corresponding patient specimens.

A neoplastic cellularity of more than 90% was obtained in all cases by microdissection or cryostat enrichment. Total RNA was extracted with Trizol (Invitrogen, Carlsbad, Calif.) according to the manufacturer's instructions from at least ten 20-30 μm thick cryostat sections, checking the cell composition of the sample every five sections. The integrity of total RNA was confirmed in each case using the Agilent 2100 Bioanalyzer (Agilent Technologies, Palo Alto, Calif.).

TABLE 2

Clinicopathological data of the pancreatic endocrine and acinar tumors.

| | Case[a] | Sex | Age | Size (Cm) | Diagnosis[b] | Invasion[c] | Metastases LN[f] | Liver | Vascular Invasion | Insulin[d] IHC | Ki67[e] (%) |
|---|---|---|---|---|---|---|---|---|---|---|---|
| F- | K29 | F | 46 | 9 | WDEC | yes | yes | yes | yes | pos-w | 20 |
| F- | K11 | F | 46 | 1.5 | WDET-b | no | no | no | no | pos | 2 |
| F- | K36 | M | 23 | 1.3 | WDET-b | no | no | no | no | pos-w | 2 |
| F- | Q2 | M | 51 | 1.5 | WDET-b | no | no | no | no | pos | 2 |
| F- | Q4 | F | 63 | 1.2 | WDET-b | no | no | no | no | pos-w | 1 |
| F- | Q6 | M | 51 | 1.3 | WDET-b | no | no | no | no | pos | 1 |
| F- | K20 | F | 27 | 5 | WDET-u | no | no | no | no | pos | 5 |
| F- | K47 | M | 66 | 2.5 | WDET-u | no | no | no | no | pos-w | 1 |
| F- | K66 | M | 33 | 5 | WDET-u | no | no | no | yes | pos-w | 10 |
| F- | K69 | M | 67 | 2.5 | WDET-u | no | no | no | no | pos | n.a.[g] |
| F- | K80 | F | 35 | 4 | WDET-u | no | no | no | no | pos | 1 |
| F- | Q14 | M | 41 | 1.3 | WDET-u | no | no | no | no | pos | 3 |

TABLE 2-continued

Clinicopathological data of the pancreatic endocrine and acinar tumors.

| Case[a] | | Sex | Age | Size (Cm) | Diagnosis[b] | Invasion[c] | Metastases LN[f] | Liver | Vascular Invasion | Insulin[d] IHC | Ki67[e] (%) |
|---|---|---|---|---|---|---|---|---|---|---|---|
| NF- | K14 | M | 48 | 11 | WDEC | yes | no | no | yes | neg | 5 |
| NF- | K15 | M | 44 | 18 | WDEC | yes | yes | no | yes | neg | 20 |
| NF- | K16 | M | 48 | 6.5 | WDEC | yes | yes | no | yes | n.a. | 3 |
| NF- | K19 | F | 37 | 4 | WDEC | no | yes | no | no | neg | 30 |
| NF- | K23 | M | 56 | 7 | WDEC | yes | yes | yes | yes | pos | 5 |
| NF- | K25 | F | 60 | 2 | WDEC | yes | no | no | yes | neg | 2 |
| NF- | K3 | M | 42 | 4.5 | WDEC | yes | yes | yes | yes | neg | 8 |
| NF- | K31 | F | 54 | 3 | WDEC | yes | yes | yes | yes | neg | 20 |
| NF- | K32 | F | 61 | 4.5 | WDEC | no | no | yes | yes | neg | 15 |
| NF- | K37 | F | 35 | 3 | WDEC | no | yes | no | no | neg | 2 |
| NF- | K42 | F | 65 | 4.5 | WDEC | yes | yes | no | no | neg | 2 |
| NF- | K43 | M | 53 | 4 | WDEC | yes | yes | yes | yes | pos-w | 10 |
| NF- | K6 | F | 51 | 12 | WDEC | no | no | yes | yes | neg | 7 |
| NF- | K76 | F | 40 | 5.5 | WDEC | no | yes | no | yes | neg | 5 |
| NF- | K9 | F | 70 | 5.5 | WDEC | yes | yes | yes | yes | n.a. | 25 |
| NF- | Q12 | M | 56 | 4.5 | WDEC | yes | no | no | yes | neg | 2 |
| NF- | Q5 | M | 38 | 3 | WDEC | yes | yes | yes | yes | neg | 3 |
| NF- | K63 | M | 58 | 1.2 | WDET-b | no | no | no | no | neg | 2 |
| NF- | K8 | F | 42 | 1.5 | WDET-b | no | no | no | no | neg | 2 |
| NF- | K10 | F | 66 | 1.5 | WDET-u | no | no | no | no | neg | 2 |
| NF- | K13 | F | 66 | 2 | WDET-u | no | no | no | no | neg | 2 |
| NF- | K2 | M | 68 | 1.5 | WDET-u | no | no | no | yes | n.a. | 1 |
| NF- | K24 | F | 49 | 11 | WDET-u | no | no | no | no | neg | 1 |
| NF- | K35 | M | 40 | 8 | WDET-u | no | no | no | no | neg | 2 |
| NF- | K41 | M | 39 | 3 | WDET-u | no | no | no | yes | neg | 1 |
| NF- | K7 | M | 57 | 2 | WDET-u | no | no | no | no | neg | 3 |
| NF- | K75 | F | 69 | 2.5 | WDET-u | no | no | no | no | neg | 1 |
| NF- | Q13 | F | 65 | 3 | WDET-u | no | no | no | yes | neg | 2 |
| AC- | K53 | M | 36 | 7 | ACC | no | no | no | yes | neg | 10 |
| AC- | K54 | M | 64 | 5 | ACC | no | no | no | no | neg | 12 |
| AC- | K58 | M | 39 | 6 | ACC | yes | yes | no | yes | neg | 15 |
| AC- | K60 | M | 52 | 17 | ACC | yes | yes | no | yes | neg | n.a. |

[a]Cases are identified by a random assigned number precede by F or NF if they are functioning or nonfunctioning endocrine tumors, respectively.
[b]WDEC, well differentiated endocrine carcinoma; WDET-b, well differentiated endocrine tumor with benign behavior; WDET-u, well differentiated endocrine tumor with uncertain biological behavior.
[c]Invasion of peripancreatic fat and/or adjacent organs (e.g. duodenum, choledocus, spleen).
[d]IHC, immunohistochemistry; pos, positive; pos-w, positive with weak signal; neg, negative.
[e]Proliferation index measured by Ki67 immunohistochemistry.
[f]LN, lymph nodes.
[g]n.a., not available.

MicroRNA Microarray Hybridization and Quantification.

MicroRNA labeling and hybridization on microRNA microarray chips were performed as previously described (Liu, C. G., et al., "An Oligonucleotide Microchip for Genome-Wide microRNA Profiling in Human and Mouse Tissues." *Proc. Natl. Acad. Sci. USA* 101:9740-44 (2004)). Briefly, 5 μg of total RNA from each sample was reverse transcribed using biotin end-labeled random octamers. Hybridization was carried out on our custom microRNA microarray chip (OSU-CCC version 2.0), which contains probes for 460 mature microRNAs (235 *Homo sapiens*, 222 *Mus musculus*, and 3 *Arabidopsis thaliana*) spotted in quadruplicate with annotated active sites. Often, more than one probe set exists for a given mature microRNA. Additionally, there are quadruplicate probes corresponding to most pre-microRNA for detecting the microRNA precursor. The microarray also includes probes for several splicing snRNAs, including U6. Hybridization signals were detected with Streptavidin-Alexa647 conjugate and scanned using Axon 4000B. Scan images were quantified using the Genepix 6.0 software (Axon Instruments (now Molecular Devices Corp.), Sunnyvale, Calif.).

Computational Analyses of microRNA Microarray Data.

Most of the analysis and graphics were generated using R software v. 2.0.1 and Bioconductor v. 1.6 packages (Gentleman, R. C., et al., "Bioconductor: Open Software Development for Computational Biology and Bioinformatics." *Genome Biol.* 5:R80 (2004)). Sequentially, the blank and probe controls spots were removed from the dataset of the 56 microRNA microarrays, and the local background was then subtracted from the median signal. Next, the data was normalized using a variance-stabilizing transformation stratified, within each array, by grid in the vsn package. Subsequently, genefilter package was used to remove all the spots whose intensities were lower than $99^{th}$ percentile of the blank spots in all the arrays. The relative hybridization to blank/negative control probes and subsequent Northern analysis indicated that the absolute value of log-transformed signals less than 4.5 are unreliable.

The data obtained were further analyzed by direct two class unpaired comparison using the samr package. The tables of differentially expressed microRNAs were obtained applying the input criteria (based on fold-change and delta value) that are specifically reported in their title. In order to increase stringency, microRNA probes were further filtered retaining those that had at least three significant replicas.

Hierarchical cluster analysis was performed using the aggregate values of replicate spots obtained applying Tukey's median polish algorithm. The analysis was done using the first 200 probes with the highest interquartile range, which contained the mature microRNA sequences. The distance metrics used to cluster samples and genes were Pearson correlation and Euclidean distance, respectively. The agglomerative method was the complete-linkage. The output was visualized using Maple Tree (version 0.2.3.2) (www.mapletree.sourceforge.net). All data were submitted using MIAMExpress to the Array Express database.
The level of coordinate expression between microRNAs was measured by Pearson correlation and microRNA genes were assigned to the same cluster when their distance was below 50 kb (Baskerville, S, and D. P. Bartel, "Microarray Profiling of microRNAs Reveals Frequent Coexpression with Neighboring miRNAs and Host Genes." *RNA* 11: 241-47 (2005)). Next, the set of correlation values measured between microRNAs belonging to the same cluster were compared to the set of correlation values measured between each microRNA in a cluster vs. all other microRNAs out of that cluster using Mann-Whitney non-parametric test.

Northern Blotting.

Five 1 μg of total RNAs were run on 15% Criterion precast PAGE/Urea gels (Bio-Rad, Hercules, Calif.), transferred onto Hybond-N+ membrane (Amersham Biosciences, Piscataway, N.J.) and hybridized overnight with $^{32}$P end-labeled DNA probes at 37° C. in ULTRAhyb™-Oligo hybridization buffer (Ambion, Austin, Tex.). Membranes were washed at 37° C. twice for 30 minutes each with 2×SSC/0.5% SDS. The DNA probes were antisense oligonucleotides relative to the mature microRNAs and to 5S RNA as a control. Filters were analyzed using a Typhoon 9410 phoshorimager (Amersham Biosciences, Piscataway, N.J.) and quantified using ImageQuant TL (Amersham Biosciences, Piscataway, N.J.). Blots were stripped by boiling in 0.1% aqueous SDS for five minutes and were reprobed several times.

Results

MicroRNA expression profiles were determined for 12 normal pancreas samples and 44 pancreatic tumors, including 40 PETs and four PACCs, using a custom microarray. This platform was proved to give robust results, as validated by several previous studies (Liu, C. G., et al., *Proc. Natl. Acad. Sci. USA* 101:9740-44 (2004); Calin, G., et al., *New Engl. J. Med.* 353(17):1793-1801 (2005); Iorio, M. V., et al., *Cancer Res.* 65:7065-70 (2005)). Further support was provided by the finding that microRNAs that are physically linked in genomic clusters were coexpressed, confirming that grouped microRNA genes show coordinate expression (Baskerville, S., and D. P. Bartel, *RNA* 11:241-47 (2005); Altuvia, Y., et al., *Nucleic Acids Res.* 33:2697-2706 (2005)).

The unsupervised analysis by hierarchical clustering, using the two hundred most variable microRNAs, showed a common microRNA expression pattern distinguishing pancreatic endocrine and acinar tumors from normal pancreas (FIGS. 1A-1E). Notably, PACCs fell into a unique cluster that was part of the wider cluster including all PETs, while there was no distinctive pattern between insulinomas and NF-PET.

Class comparison analysis confirmed the differential expression of several microRNAs between PACC or PET and normal tissue, while a smaller number of microRNAs were differentially expressed between PET and PACC, as well as between the WDEC subgroup of PET and PACC. In particular, PET showed 87 upregulated and 8 downregulated microRNAs, as compared to normal pancreas (Table 3), while PACC had 30 microRNAs upregulated and 7 downregulated (Table 4). Only ten microRNAs were differentially expressed between PET and PACC (Table 5), and four were unique to WDEC, with respect to PACC (Table 6).

TABLE 3

Differentially-expressed microRNAs between PETs and Normal Bulk Pancreas
(FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| Upregulated microRNAs | | | | | | | |
| hsa-mir-103-2 | 12.017 | 14.52 | 0 | MI0000108 | 20p13 | Yes | 20 |
| hsa-mir-107 | 11.885 | 15.94 | 0 | MI0000114 | 10q23.31 | Yes | 20 |
| hsa-mir-103-1 | 11.296 | 14.18 | 0 | MI0000109 | 5q34 | Yes | 20 |
| hsa-mir-342 | 10.970 | 10.09 | 0 | MI0000805 | 14q32.2 | Yes | 186 |
| hsa-mir-100 | 10.277 | 9.71 | 0 | MI0000102 | 11q24.1 | Yes | 17 |
| hsa-mir-24-2 | 10.116 | 6.20 | 0 | MI0000081 | 19p13.12 | Yes | 38 |
| hsa-mir-23a | 9.468 | 7.11 | 0 | MI0000079 | 19p13.12 | Yes | 32 |
| hsa-mir-125a | 9.011 | 7.52 | 0 | MI0000469 | 19q13.41 | Yes | 9 |
| hsa-mir-26a-1 | 8.787 | 5.34 | 0 | MI0000083 | 3p22.3 | Yes | 39 |
| hsa-mir-24-1 | 8.762 | 4.67 | 0 | MI0000080 | 9q22.32 | Yes | 38 |
| hsa-mir-191 | 8.570 | 5.78 | 0 | MI0000465 | 3p21.31 | Yes | 176 |
| hsa-mir-15a | 7.774 | 3.94 | 0 | MI0000069 | 13q14.2 | Yes | 24 |
| hsa-mir-368 | 7.718 | 6.61 | 0 | MI0000776 | 14q32.31 | Yes | 124 |
| hsa-mir-26b | 7.710 | 5.15 | 0 | MI0000084 | 2q35 | Yes | 39 |
| hsa-mir-125b-2 | 7.687 | 6.52 | 0 | MI0000470 | 21q21.1 | Yes | 9 |
| hsa-mir-125b-1 | 7.623 | 8.08 | 0 | MI0000446 | 11q24.1 | Yes | 9 |
| hsa-mir-26a-2 | 7.498 | 5.52 | 0 | MI0000750 | 12q14.1 | Yes | 39 |
| hsa-mir-335 | 7.361 | 2.94 | 0 | MI0000816 | 7q32.2 | Yes | 192 |
| hsa-mir-126 | 7.210 | 6.06 | 0 | MI0000471 | 9q34.3 | Yes | 127 |
| hsa-mir-1-2 | 7.170 | 6.58 | 0 | MI0000437 | 18q11.2 | Yes | 35 |
| hsa-mir-21 | 7.030 | 5.78 | 0 | MI0000077 | 17q23.2 | Yes | 61 |
| hsa-mir-25 | 7.017 | 4.16 | 0 | MI0000082 | 7q22.1 | Yes | 69 |
| hsa-mir-92-2 | 7.005 | 3.86 | 0 | MI0000094 | Xq26.2 | Yes | 30 |
| hsa-mir-130a | 6.985 | 4.32 | 0 | MI0000448 | 11q12.1 | Yes | 50 |
| hsa-mir-93 | 6.971 | 3.56 | 0 | MI0000095 | 7q22.1 | Yes | 2 |
| hsa-mir-16-1 | 6.785 | 4.57 | 0 | MI0000070 | 13q14.2 | Yes | 46 |
| hsa-mir-145 | 6.770 | 4.49 | 0 | MI0000461 | 5q32 | Yes | 70 |
| hsa-mir-17 | 6.759 | 4.03 | 0 | MI0000071 | 13q31.3 | Yes | 2 |
| hsa-mir-99b | 6.681 | 5.91 | 0 | MI0000746 | 19q13.41 | Yes | 17 |
| hsa-mir-181b-1 | 6.645 | 4.80 | 0 | MI0000270 | 1q31.3 | Yes | 44 |
| hsa-mir-146 | 6.639 | 4.29 | 0 | MI0000477 | 5q33.3 | Yes | 109 |

TABLE 3-continued

Differentially-expressed microRNAs between PETs and Normal Bulk Pancreas
(FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| hsa-mir-181b-2 | 6.613 | 4.45 | 0 | MI0000683 | 9q33.3 | Yes | 44 |
| hsa-mir-16-2 | 6.613 | 3.90 | 0 | MI0000115 | 3q25.33 | Yes | 46 |
| hsa-mir-99a | 6.561 | 4.35 | 0 | MI0000101 | 21q21.1 | Yes | 17 |
| hsa-mir-197 | 6.512 | 2.44 | 0 | MI0000239 | 1p13.3 | Yes | 112 |
| hsa-mir-10a | 6.447 | 4.44 | 0 | MI0000266 | 17q21.32 | Yes | 33 |
| hsa-mir-224 | 6.445 | 2.93 | 0 | MI0000301 | Xq28 | Yes | 85 |
| hsa-mir-92-1 | 6.442 | 3.08 | 0 | MI0000085 | 13q31.3 | Yes | 30 |
| hsa-mir-27a | 6.255 | 3.34 | 0 | MI0000085 | 19p13.12 | Yes | 40 |
| hsa-mir-221 | 6.171 | 8.97 | 0 | MI0000298 | Xp11.3 | Yes | 90 |
| hsa-mir-320 | 6.143 | 2.38 | 0 | MI0000542 | 8p21.3 | Yes | 162 |
| hsa-mir-7-1 | 6.133 | 4.84 | 0 | MI0000263 | 9q21.32 | Yes | 12 |
| hsa-mir-29b-2 | 6.110 | 4.07 | 0 | MI0000107 | 1q32.2 | Yes | 8 |
| hsa-mir-150 | 6.033 | 2.63 | 0 | MI0000479 | 19q13.33 | Yes | 178 |
| hsa-mir-30d | 5.930 | 5.11 | 0 | MI0000255 | 8q24.22 | Yes | 28 |
| hsa-mir-29a | 5.930 | 3.87 | 0 | MI0000087 | 7q32.3 | Yes | 8 |
| hsa-mir-23b | 5.803 | 3.02 | 0 | MI0000439 | 9q22.32 | Yes | 32 |
| hsa-mir-135a-2 | 5.675 | 2.86 | 0 | MI0000453 | 12q23.1 | Yes | 31 |
| hsa-mir-223 | 5.580 | 3.46 | 0 | MI0000300 | Xq12 | Yes | 68 |
| hsa-mir-3p21-v | 5.579 | 2.32 | 0 | NA | NA | Yes | NA |
| hsa-mir-128b | 5.557 | 4.35 | 0 | MI0000727 | 3p22.3 | Yes | 51 |
| hsa-mir-30b | 5.551 | 4.25 | 0 | MI0000441 | 8q24.22 | Yes | 27 |
| hsa-mir-29b-1 | 5.456 | 3.14 | 0 | MI0000105 | 7q32.3 | Yes | 8 |
| hsa-mir-106b | 5.448 | 2.37 | 0 | MI0000734 | 7q22.1 | Yes | 2 |
| hsa-mir-132 | 5.445 | 6.39 | 0 | MI0000449 | 17p13.3 | Yes | 110 |
| hsa-mir-214 | 5.440 | 2.58 | 0 | MI0000290 | 1q24.3 | Yes | 62 |
| hsa-mir-7-3 | 5.418 | 4.72 | 0 | MI0000265 | 19p13.3 | Yes | 12 |
| hsa-mir-29c | 5.406 | 3.12 | 0 | MI0000735 | 1q32.2 | Yes | 8 |
| hsa-mir-367 | 5.398 | 3.47 | 0 | MI0000775 | 4q25 | Yes | NA |
| hsa-mir-30c-2 | 5.356 | 4.10 | 0 | MI0000254 | 6q13 | Yes | 27 |
| hsa-mir-27b | 5.344 | 2.98 | 0 | MI0000440 | 9q22.32 | Yes | 40 |
| hsa-mir-140 | 5.251 | 3.09 | 0 | MI0000456 | 16q22.1 | Yes | 95 |
| hsa-mir-10b | 5.218 | 3.46 | 0 | MI0000267 | 2q31.1 | Yes | 33 |
| hsa-mir-20 | 5.208 | 3.45 | 0 | MI0000076 | 13q31.3 | Yes | 2 |
| hsa-mir-129-1 | 5.143 | 3.97 | 0 | MI0000252 | 7q32.1 | No | 93 |
| hsa-mir-340 | 5.123 | 2.67 | 0 | MI0000802 | 5q35.3 | Yes | 181 |
| hsa-mir-30a | 5.119 | 3.29 | 0 | MI0000088 | 6q13 | Yes | 28 |
| hsa-mir-30c-1 | 5.065 | 3.88 | 0 | MI0000736 | 1p34.2 | Yes | 27 |
| hsa-mir-106a | 4.974 | 2.81 | 0 | MI0000113 | Xq26.2 | Yes | 2 |
| hsa-mir-32 | 4.763 | 2.34 | 0 | MI0000090 | 9q31.3 | Yes | 63 |
| hsa-mir-95 | 4.582 | 2.53 | 0 | MI0000097 | 4p16.1 | Yes | 87 |
| hsa-mir-222 | 4.417 | 3.48 | 0 | MI0000299 | Xp11.3 | Yes | 103 |
| hsa-mir-30e | 4.149 | 4.01 | 0 | MI0000749 | 1p34.2 | Yes | 28 |
| hsa-mir-129-2 | 3.946 | 2.27 | 0 | MI0000473 | 11p11.2 | Yes | 93 |
| hsa-mir-345 | 3.909 | 2.31 | 0 | MI0000825 | 14q32.2 | Yes | 193 |
| hsa-mir-143 | 3.808 | 2.58 | 0 | MI0000459 | 5q32 | Yes | 74 |
| hsa-mir-182 | 3.762 | 3.78 | 0 | MI0000272 | 7q32.2 | Yes | 126 |
| hsa-mir-1-1 | 3.674 | 2.22 | 0 | MI0000651 | 20q13.33 | Yes | 35 |
| hsa-mir-133a-1 | 3.583 | 2.66 | 0 | MI0000450 | 18q11.2 | Yes | 25 |
| hsa-mir-200c | 3.463 | 3.08 | 0 | MI0000650 | 12p13.31 | Yes | 111 |
| hsa-mir-194-1 | 3.345 | 3.57 | 0 | MI0000488 | 1q41 | Yes | 54 |
| hsa-mir-210 | 3.330 | 2.73 | 0 | MI0000286 | 11p15.5 | Yes | 134 |
| hsa-mir-181c | 3.116 | 2.38 | 0 | MI0000271 | 19p13.12 | Yes | 21 |
| hsa-mir-192 | 2.905 | 2.71 | 0 | MI0000234 | 11q13.1 | Yes | 64 |
| hsa-mir-220 | 2.877 | 2.45 | 0 | MI0000297 | Xq25 | Yes | 101 |
| hsa-mir-213 | 2.825 | 2.61 | 0 | MI0000289 | 1q31.3 | Yes | 21 |
| hsa-mir-323 | 2.589 | 3.75 | 0 | MI0000807 | 14q32.31 | Yes | 23 |
| Downregulated microRNAs | | | | | | | |
| hsa-mir-326 | −6.697 | 0.36 | 0 | MI0000808 | 11q13.4 | Yes | 148 |
| hsa-mir-155 | −6.357 | 0.21 | 0 | MI0000681 | 21p21.3 | Yes | 150 |
| hsa-mir-339 | −5.531 | 0.41 | 0 | MI0000815 | 7q22.3 | Yes | 191 |
| hsa-mir-34c | −4.924 | 0.42 | 0 | MI0000743 | 11q23.1 | Yes | 94 |
| hsa-mir-345 | −4.873 | 0.49 | 0 | MI0000825 | 14q32.2 | Yes | 193 |
| hsa-mir-152 | −4.837 | 0.50 | 0 | MI0000462 | 17q21.32 | No | 59 |
| hsa-mir-372 | −4.221 | 0.43 | 0 | MI0000780 | 19q13.42 | Yes | 217 |
| hsa-mir-128a | −4.149 | 0.50 | 0 | MI0000447 | 2q21.3 | No | 51 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 4

Differentially-expressed microRNAs between ACCss and Normal Bulk Pancreas
(FDR: 0% on the 90th percentile and 2-Fold).

| MicroRNA Name | Score (a) | Fold Change | q-value (b) | Accession ID | Chromosome | Active site (c) | microRNA Families (d) |
|---|---|---|---|---|---|---|---|
| Upregulated microRNAs | | | | | | | |
| hsa-mir-103-2 | 3.926 | 6.46 | 0 | MI0000108 | 20p13 | Yes | 20 |
| hsa-mir-25 | 3.871 | 4.79 | 0 | MI0000082 | 7q22.1 | Yes | 69 |
| hsa-mir-200c | 3.828 | 3.88 | 0 | MI0000650 | 12p13.31 | Yes | 111 |
| hsa-mir-335 | 3.702 | 3.46 | 0 | MI0000816 | 7q32.2 | Yes | 192 |
| hsa-mir-21 | 3.532 | 5.22 | 0 | MI0000077 | 17q23.2 | Yes | 61 |
| hsa-mir-103-1 | 3.474 | 6.09 | 0 | MI0000109 | 5q34 | Yes | 20 |
| hsa-mir-92-1 | 3.419 | 3.13 | 0 | MI0000093 | 13q31.3 | Yes | 30 |
| hsa-mir-181b-2 | 3.369 | 3.35 | 0 | MI0000683 | 9q33.3 | Yes | 44 |
| hsa-mir-191 | 3.344 | 4.95 | 0 | MI0000465 | 3p21.31 | Yes | 176 |
| hsa-mir-93 | 3.299 | 3.60 | 0 | MI0000095 | 7q22.1 | Yes | 2 |
| hsa-mir-26a-1 | 3.248 | 3.85 | 0 | MI0000083 | 3p22.3 | Yes | 39 |
| hsa-mir-17 | 3.211 | 3.76 | 0 | MI0000071 | 13q31.3 | Yes | 2 |
| hsa-mir-20 | 3.201 | 3.37 | 0 | MI0000076 | 13q31.3 | Yes | 2 |
| hsa-mir-107 | 3.195 | 6.16 | 0 | MI0000114 | 10q23.31 | Yes | 20 |
| hsa-mir-26b | 3.185 | 4.15 | 0 | MI0000084 | 2q35 | Yes | 39 |
| hsa-mir-215 | 3.123 | 4.70 | 0 | MI0000291 | 1q41 | Yes | 64 |
| hsa-mir-92-2 | 3.088 | 3.60 | 0 | MI0000094 | Xq26.2 | Yes | 30 |
| hsa-mir-192 | 3.044 | 3.24 | 0 | MI0000234 | 11q13.1 | Yes | 64 |
| hsa-mir-342 | 2.997 | 3.37 | 0 | MI0000805 | 14q32.2 | Yes | 186 |
| hsa-mir-100 | 2.918 | 3.36 | 0 | MI0000102 | 11q24.1 | Yes | 17 |
| hsa-mir-3p21-v | 2.895 | 2.35 | 0 | NA | NA | Yes | NA |
| hsa-mir-106a | 2.833 | 3.02 | 0 | MI0000113 | Xq26.2 | Yes | 2 |
| hsa-mir-15a | 2.809 | 2.83 | 0 | MI0000069 | 13q14.2 | Yes | 24 |
| hsa-mir-23a | 2.748 | 4.23 | 0 | MI0000079 | 19p13.12 | Yes | 32 |
| hsa-mir-181b-1 | 2.732 | 4.00 | 0 | MI0000270 | 1q31.3 | Yes | 44 |
| hsa-mir-128b | 2.709 | 2.58 | 0 | MI0000727 | 3p22.3 | Yes | 51 |
| hsa-mir-106b | 2.485 | 2.50 | 0 | MI0000734 | 7q22.1 | Yes | 2 |
| hsa-mir-194-1 | 2.432 | 3.21 | 0 | MI0000488 | 1q41 | Yes | 54 |
| hsa-mir-219-1 | 2.404 | 2.06 | 0 | MI0000296 | 6q21.32 | Yes | 47 |
| hsa-mir-24-2 | 2.388 | 3.27 | 0 | MI0000081 | 19p13.12 | Yes | 38 |
| Downregulated microRNAs | | | | | | | |
| hsa-mir-218-2 | −4.346 | 0.27 | 0 | MI0000295 | 5q34 | Yes | 29 |
| hsa-mir-339 | −4.272 | 0.27 | 0 | MI0000815 | 7q22.3 | Yes | 191 |
| hsa-mir-326 | −4.037 | 0.26 | 0 | MI0000808 | 11q13.4 | Yes | 148 |
| hsa-mir-34c | −3.525 | 0.27 | 0 | MI0000743 | 11q23.1 | Yes | 94 |
| hsa-mir-152 | −3.507 | 0.31 | 0 | MI0000462 | 17q21.32 | No | 59 |
| hsa-mir-138-2 | −3.398 | 0.33 | 0 | MI0000455 | 16q13 | Yes | 88 |
| hsa-mir-128a | −3.021 | 0.33 | 0 | MI0000447 | 2q21.3 | No | 51 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 5

Differentially-expressed microRNAs between PETs and PACC
(FDR: 1% on the 90th percentile and 2-fold).
Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-125a | 4.382 | 4.19 | 0 | MI0000469 | 19q13.41 | Yes | 9 |
| hsa-mir-99a | 3.711 | 3.62 | 0 | MI0000101 | 21q21.1 | Yes | 17 |
| hsa-mir-99b | 3.287 | 4.25 | 0 | MI0000746 | 19q13.41 | Yes | 17 |
| hsa-mir-125b-1 | 3.271 | 3.33 | 0 | MI0000446 | 11q24.1 | Yes | 9 |
| hsa-mir-342 | 3.152 | 3.00 | 0 | MI0000805 | 14q32.2 | Yes | 186 |
| hsa-mir-130a | 3.101 | 2.69 | 0 | MI0000448 | 11q12.1 | Yes | 50 |
| hsa-mir-100 | 3.028 | 2.93 | 0 | MI0000102 | 11q24.1 | Yes | 17 |
| hsa-mir-132 | 2.952 | 5.44 | 0 | MI0000449 | 17p13.3 | Yes | 110 |

TABLE 5-continued

Differentially-expressed microRNAs between PETs and PACC
(FDR: 1% on the 90th percentile and 2-fold).

Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-129-2 | 2.910 | 3.86 | 0 | MI0000473 | 11p11.2 | Yes | 93 |
| hsa-mir-125b-2 | 2.886 | 2.94 | 0 | MI0000470 | 21q21.1 | Yes | 9 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 6

Differentially-expressed microRNAs between WDEC and ACC
(FDR: 1% on the 90th percentile and 2-fold).

| MicroRNA Name | Score (a) | Fold Change | q-value (b) | Accession ID | Chromosome | Active site (c) | microRNA Families (d) |
|---|---|---|---|---|---|---|---|
| Upregulated microRNAs | | | | | | | |
| hsa-mir-125a | 3.785 | 3.76 | 0 | MI0000469 | 19q13.41 | Yes | 9 |
| hsa-mir-99a | 3.186 | 3.65 | 0 | MI0000101 | 21q21.1 | Yes | 17 |
| hsa-mir-132 | 2.969 | 4.84 | 0 | MI0000449 | 17p13.3 | Yes | 110 |
| Downregulated microRNAs | | | | | | | |
| hsa-mir-148a | −3.781 | 0.21 | 0 | MI0000253 | 7p15.2 | Yes | 59 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 7

Differentially-expressed microRNAs between Insulomas and Non-Functioning PETs
(FDR: 1% on the 90th percentile and 2-fold).

Upregulated microRNAs

| MicroRNA Name | Score (a) | Fold Change | q-value (b) | Accession ID | Chromosome | Active site (c) | microRNA Families (d) |
|---|---|---|---|---|---|---|---|
| hsa-mir-204 | 5.441 | 6.07 | 0 | MI0000284 | 9q21.11 | Yes | 43 |
| hsa-mir-203 | 4.079 | 2.83 | 0 | MI0000283 | 14q32.11 | No | 113 |
| hsa-mir-211 | 3.931 | 2.81 | 0 | MI0000287 | 15q13.3 | Yes | 43 |

(a) Score: T-statistic values.
(b) q value: this is the lowest False Discovery Rate at which the gene is called significant. It is like the familiar "p-value", adapted to the analysis of a large number of genes.
(c) Active site: indicates if the probe contains the mature form of the microRNA.
(d) microRNA Family: related microRNA based on homology in the hairpin flanking reions as reported in The miRBase Sequence Database - Release 7.0.

TABLE 8

Differentially expressed MicroRNAs between PETs with different clinicopathological parameters.

| MicroRNA Name | Score (a) | Fold Change | q-value (b) | Accession ID | Chromosome | Active site (c) | microRNA Families (d) |
|---|---|---|---|---|---|---|---|
| PET with or without liver metastasis (FDR: 0% on the median percentile and 1.8-Fold). | | | | | | | |
| Upregulated microRNA | | | | | | | |
| hsa-mir-21 | 2.239446173 | 1.93 | 0 | MI0000077 | 17q23.2 | Yes | 61 |
| PET with High (Ki67 > 2%) or Low (Ki67 ≦ 2%) proliferation index (FDR: 0% on the median percentile and 1.8-Fold). | | | | | | | |
| Upregulated microRNA | | | | | | | |
| hsa-mir-21 | 2.869445623 | 1.84 | 0 | MI0000077 | 17q23.2 | Yes | 61 |

TABLE 8-continued

Differentially expressed MicroRNAs between PETs with different clinicopathological parameters.

| MicroRNA Name | Score (a) | Fold Change | q-value (b) | Accession ID | Chromosome | Active site (c) | microRNA Families (d) |
|---|---|---|---|---|---|---|---|
| Non-Functioning PETs with High (Ki67 > 2%) or Low (Ki67 ≦ 2%) proliferation index (FDR: 0% on the median percentile and 2-Fold). Upregulated microRNA | | | | | | | |
| hsa-mir-21 | 2.513043962 | 2.10 | 0 | MI0000077 | 17q23.2 | Yes | 61 |
| WDECs with High (Ki67 > 2%) or Low (Ki67 ≦ 2%) proliferation index (FDR: 0% on the median percentile and 2-Fold). Upregulated microRNA | | | | | | | |
| hsa-mir-021 | 1.642156912 | 2.32 | 0 | MI0000077 | 17q23.2 | Yes | 61 |

(a) Score: T-statistic values.

(b) q value: this is the lowest False Discovery Rate at which the gene is called significant. It is like the familiar "p-value", adapted to the analysis of a large number of genes.

(c) Active site: indicates if the probe contains the mature form of the microRNA.

(d) microRNA Family: related microRNA based on homology in the hairpin flanking reions as reported in The miRBase Sequence Database - Release 7.0.

TABLE 9

Putative gene targets of miR-204/211 identified by three prediction methods

| Symbol | Acc Num | UniGene ID | Gene Name | Ensembl. Gene. ID | Gene ID | Chromosome |
|---|---|---|---|---|---|---|
| CDH2 | NM_001792 | Hs.464829 | Cadherin 2, type 1, N-cadherin (neuronal) | ENSG00000170558 | 1000 | 18q11.2 |
| KHDRBS1 | NM_006559 | Hs.445893 | KH domain containing, RNA binding, signal transduction associated 1 | ENSG00000121774 | 10657 | 1p32 |
| MAPRE2 | NM_014268 | Hs.532824 | Microtubule-associated protein, RP/EB family, member 2 | ENSG00000166974 | 10982 | 18q12.1 |
| NCOA7 | NM_181782 | Hs.171426 | Nuclear receptor coactivator 7 | ENSG00000111912 | 135112 | 6q22.32 |
| ATF2 | NM_001880 | Hs.425104 | Activating transcription factor 2 | ENSG00000115966 | 1386 | 2q32 |
| GLIS3 | NM_152629 | Hs.162125 | GLIS family zinc finger 3 | ENSG00000107249 | 169792 | 9p24.2 |
| EPHA7 | NM_004440 | Hs.73962 | EPH receptor A7 | ENSG00000135333 | 2045 | 6q16.1 |
| C10orf56 | NM_153367 | Hs.523080 | Chromosome 10 open reading frame 56 | ENSG00000165424 | 219654 | 10q22.3 |
| AP3M1 | NM_012095 | Hs.500104 | Adaptor-related protein complex 3, mu 1 subunit | ENSG00000185009 | 26985 | 10q22.2 |
| PRO0149 | NM_014117 | Hs.221497 | PRO0149 protein | ENSG00000182831 | 29035 | 16p13.2 |
| NRBF2 | NM_030759 | Hs.449628 | Nuclear receptor binding factor 2 | ENSG00000148572 | 29982 | 10q21.3 |
| M11S1 | NM_005898 | Hs.471818 | Membrane component, chromosome 11, surface marker 1 | ENSG00000135387 | 4076 | 11p13 |
| MYO10 | NM_012334 | Hs.481720 | Myosin X | ENSG00000145555 | 4651 | 5p15.1-p14.3 |
| NOVA1 | NM_002515 | Hs.211225 | Neuro-oncological ventral antigen 1 | ENSG00000139910 | 4857 | 14q |
| NTRK2 | NM_006180 | Hs.494312 | Neurotrophic tyrosine kinase, receptor, type 2 | ENSG00000148053 | 4915 | 9q22.1 |
| hSyn | NM_018157 | Hs.368253 | Brain synembryn | ENSG00000111785 | 55188 | 12q23.3 |
| HMGA2 | NM_003483 | Hs.505924 | High mobility group AT-hook 2 | ENSG00000149948 | 8091 | 12q15 |
| AKAP1 | NM_003488 | Hs.463506 | A kinase (PRKA) anchor protein 1 | ENSG00000121057 | 8165 | 17q21-q23 |
| OGT | NM_003605 | Hs.405410 | O-linked N-acetylglucosamine (GlcNAc) transferase (UDP-N-acetylglucosamine:polypeptide-N-acetylglucosaminyl transferase) | ENSG00000147162 | 8473 | Xq13 |
| CCNT2 | NM_001241 | Hs.292754 | Cyclin T2 | ENSG00000082258 | 905 | 2q21.3 |

TABLE 10

Putative target genes of miR-204/211 and miR-21 found to be differentially expressed

| Gene Target | Fold | p.value |
|---|---|---|

Putative target genes of miR-204/211 found differentially expressed between NF-PETs and insulinomas. EST microarray contains 16 out of 20 identified putative target genes.

| UPREGULATED | | |
|---|---|---|
| MAPRE2 | 1.75 | 0.0070 |
| AP3M1 | 1.30 | 0.0330 |
| DOWNREGULATED | | |
| MYO10 | 0.43 | 0.0014 |
| AKAP1 | 0.59 | 0.0114 |

Putative target genes of miR-21 found differentially expressed between PET with or without liver metastasis. EST microarray contains 11 out of 12 identified putative target genes.

| UPREGULATED | | |
|---|---|---|
| NFIB | 1.69 | 0.038 |
| DOWNREGULATED | | |
| PDCD4 | 0.71 | 0.001 |

Putative target genes of miR-21 found differentially expressed between PET high (Ki67 > 2) or low (Ki67 ≦ 2). EST microarray contains 11 out of 12 identified putative target genes.
DOWNREGULATED

| PDCD4 | 0.66 | 0.00001 |
|---|---|---|

A Common microRNA Expression Pattern Distinguishes Pancreatic Endocrine and Acinar Tumors from Normal Pancreas.

The vast majority of the differentially expressed microRNAs found in PACC vs. normal tissue were also found in PET vs. normal tissue. In particular, 28 of 30 (93%) microRNAs that were overexpressed in PACC were also found to be upregulated in PET. Similarly, five of seven (71%) underexpressed microRNAs were downregulated in both tumor subtypes. This overlap, together with the fact that only a limited set of microRNAs were differentially expressed between PET and PACC or among PET subtypes, is suggestive of a pattern of microRNA expression common to acinar and insular-derived tumors.

Figures 2A, 2B:
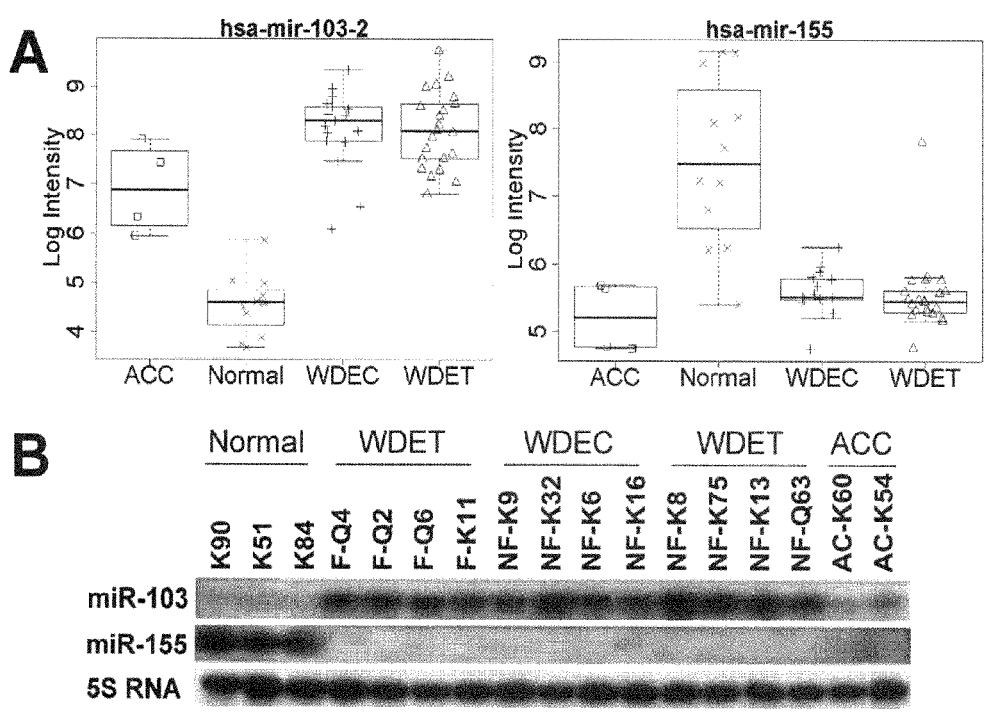
FIG. 2A depicts box-and-whiskers plots showing the expression levels of miR-103 and miR-155, which were measured by microarray analysis of 12 normal pancreas (Normal) and 44 pancreatic tumors, including 22 well-differentiated pancreatic endocrine tumors (WDET), 18 well-differentiated pancreatic endocrine carcinomas (WDEC) and 4 pancreatic acinar cell carcinomas (ACC). The median intensity is highlighted by bold lines. As shown, the overexpression of miR-103 and lack of expression of miR-155 is particular to pancreatic insular and acinar tumors.
FIG. 2B depicts Northern blot analysis, which parallels the microarray expression data shown in FIG. 2A. 5S rRNA (5S-RNA) served as a loading control.
Figures 6A, 6B, 6C:
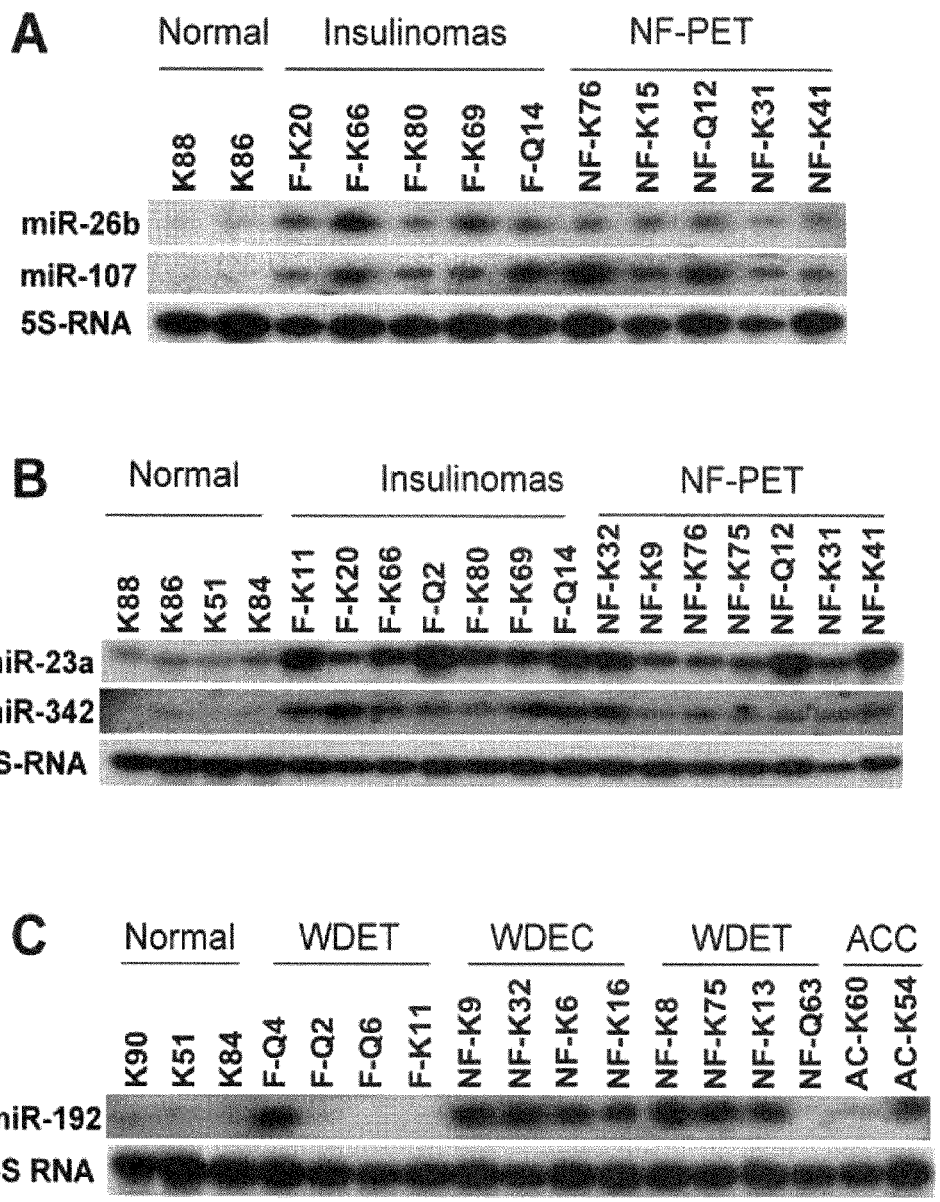
FIG. 6A depicts Northern blot analysis showing overexpression of miR-26b and miR-107 in all the pancreatic insulinomas and non functioning endocrine tumors (NF-PET) that were tested. These results validate the microarray data for the overexpressed microRNAs. 5S rRNA (5S-RNA) served as a loading control.
FIG. 6B depicts Northern blot analysis showing overexpression of miR-23a and miR-342 in all the pancreatic insulinomas and non functioning endocrine tumors (NF-PET) that were tested. These results validate the microarray data for the overexpressed microRNAs. 5S rRNA (5S-RNA) served as a loading control.
FIG. 6C depicts Northern blot analysis showing overexpression of miR-192 in four of eight well-differentiated endocrine tumors (WDET), in all four well-differentiated endocrine carcinomas (WDEC), and one acinar cell carcinoma (ACC). These results validate the microarray data for the overexpressed microRNA. 5S rRNA (5S-RNA) served as a loading control.

Among the upregulated microRNAs in PET that are also common to PACC, seven were validated by Northern blot analysis. In particular, miR-103 was the best discriminator for all pair-wise comparisons of normal pancreas, acinar cell carcinomas and pancreatic endocrine tumors (FIGS. 2A and 2B). The expression of miR-107 paralleled that of its highly homologous miR-103, and the significant overexpression of miR-23a, miR-26b, miR-192, and miR-342 in tumors vs. normal was also confirmed (FIGS. 6A-6C).

Among downregulated microRNAs in PET, Northern blot analysis of miR-155 showed the lack of detectable expression in both PET and PACC (FIGS. 2A and 2B). Although miR-155 was not among the top listed downregulated genes in PACC (Table 4), its low expression in this tumor type was also detected by microarray, as shown in the box-and-whiskers plot of FIG. 2A.

A Limited Set of microRNAs Distinguishes Pancreatic Endocrine from Acinar Tumors.

The direct comparison of PET and PACC showed only 10 upregulated microRNAs (Table 5), all of which were also overexpressed in PET vs. normal tissue. In contrast, no microRNA was found to be specifically upregulated or downregulated in PACC.

Over-Expression of miR-204 is Specific to Insulinomas and Correlates with Immunohistochemical Expression of Insulin.

Figures 3A, 3B, 3C:
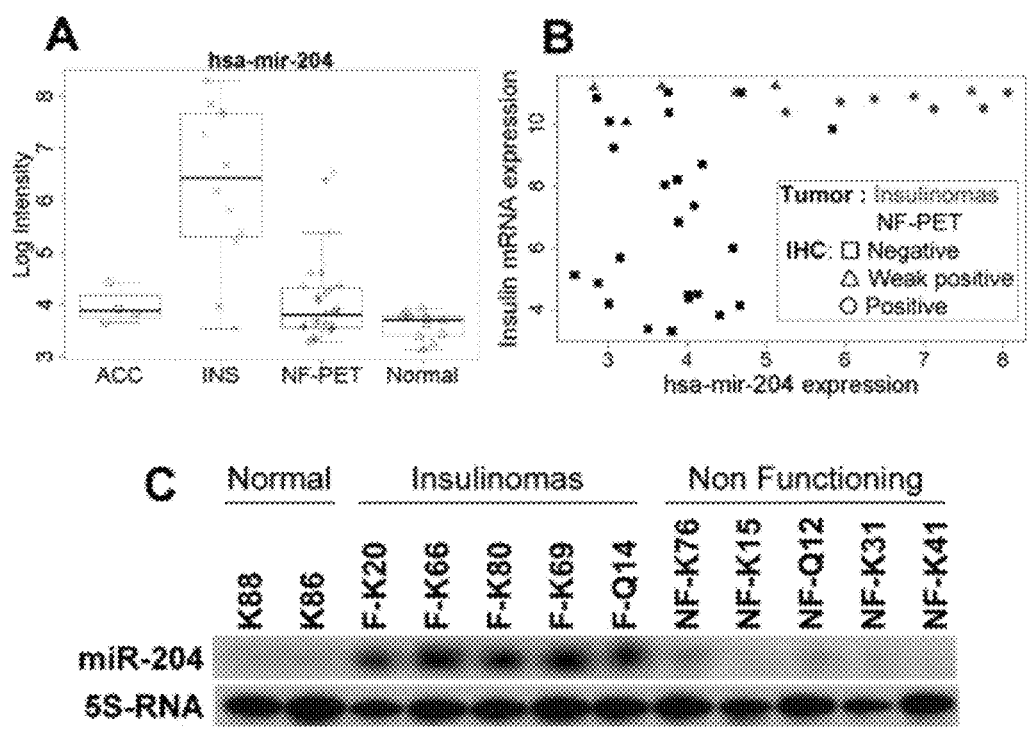
FIG. 3A depicts a box-and-whiskers plot showing the expression level of miR-204, which was measured by microarray analysis of 12 normal pancreas (Normal), 12 insulinomas, 28 non functioning pancreatic endocrine tumors (NF-PET) and 4 pancreatic acinar cell carcinomas (ACC). The median intensity is highlighted by bold lines.
FIG. 3B is a graph showing a strong correlation between miR-204 expression and insulin staining assessed by immunohistochemistry (IHC).
FIG. 3C depicts Northern blot analysis, which confirms the microarray expression data and shows that miR-204 overexpression is specific to insulinomas. 5S rRNA (5S-RNA) served as a loading control.

The comparison of insulinomas with NF-PET identified only three microRNAs that were significantly overexpressed in insulinomas, including miR-204, its homolog miR-211, and miR-203 (Table 7). Notably, the expression of insulin protein, as detected by immunohistochemical staining, correlated with miR-204 expression more strongly than with insulin mRNA expression (FIG. 3A-3C). In fact, logistic regression analysis, based on negative or positive ICH staining, showed that the insulin protein expression was predicted by both insulin mRNA and miR-204 expression ($p<0.001$); however, in a multivariate model only miR-204 expression retained statistical significance ($p<0.001$).

Figures 7A, 7B, 7C:
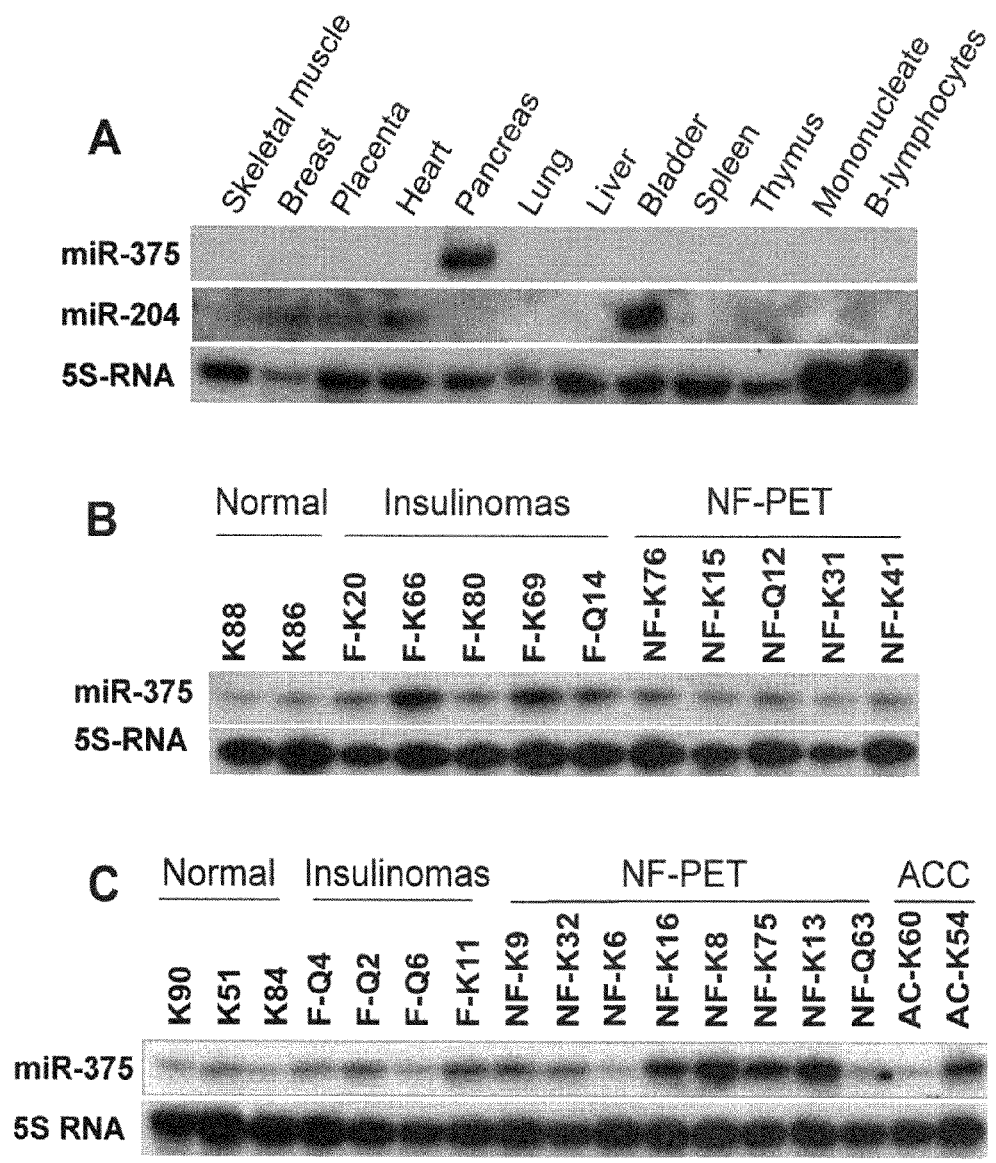
FIG. 7A depicts Northern blot analysis showing that miR-375 is a pancreas-specific miR. 5S rRNA (5S-RNA) served as a loading control.
FIG. 7B depicts Northern blot analysis showing that the expression of miR-375 is a feature of pancreatic endocrine and acinar tumors, irrespective of the presence (insulinomas) or absence (NF-PET) of clinically evident insulin oversecretion. NF-PET, nonfunctioning pancreatic endocrine tumors. 5S rRNA (5S-RNA) served as a loading control. As is shown, mir-375 expression is common in pancreatic insular and acinar tumors.
FIG. 7C depicts Northern blot analysis showing that the expression of miR-375 is a feature of pancreatic endocrine and acinar tumors, irrespective of the presence (insulinomas) or absence (NF-PET and ACC) of clinically evident insulin oversecretion. NF-PET, nonfunctioning pancreatic endocrine tumors; ACC, pancreatic acinar cell carcinomas. 5S rRNA (5S-RNA) served as a loading control. As is shown, mir-375 expression is common in pancreatic insular and acinar tumors.

As miR-375 was suggested to be specifically expressed in mouse pancreatic islets and to function as a negative regulator of insulin exocytosis (Poy, M. N., et al., Nature 432:226-30 (2004)), we investigated its expression in normal human tissues and our samples by Northern blot. Using a panel of several human adult tissues, miR-375 was only detected in normal pancreas (FIG. 7A). The expression levels of miR-375 were generally higher in tumors vs. normal pancreas, but showed no difference between insulinomas and nonfunctioning tumors (FIGS. 7B and 7C).

Expression of miR-21 is Strongly Associated with the Proliferation Index and Presence of Liver Metastasis.

Figures 4A, 4B, 4C:
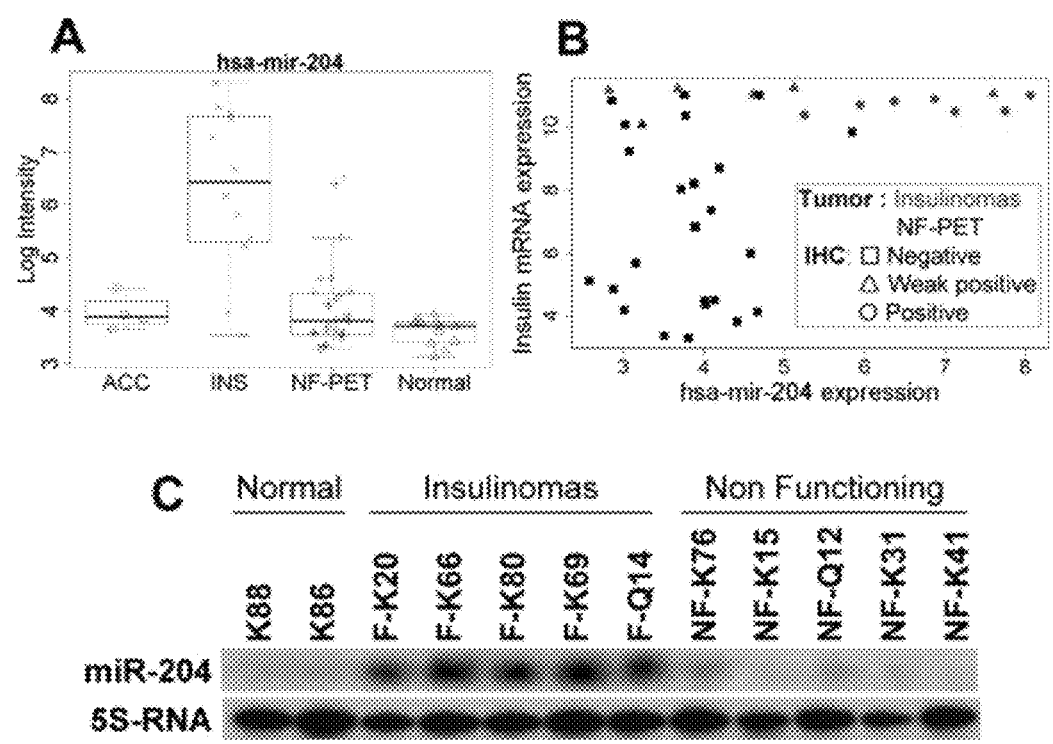
FIG. 4A depicts a box-and-whiskers plot showing the different expression level of miR-21, which was measured by microarray analysis, between pancreatic endocrine tumors with (Meta+) or without (Meta−) liver metastasis. As is shown, expression of miR-21 is strongly associated with the presence of liver metastasis.
FIG. 4B depicts a box-and-whiskers plot showing the different expression level of miR-21, which was measured by microarray analysis, between tumors with a proliferation index >2% (High) or <2% (Low), as measured by Ki67 immunohistochemistry. As is shown, expression of miR-21 is strongly associated with tumoral proliferation index.
FIG. 4C depicts Northern blot analysis, which confirms the microarray expression data. 5S rRNA (5S-RNA) served as a loading control.

The evaluation of expression profiles to identify microRNAs discriminating PETs based on either metastatic status or proliferation index identified only miR-21 as significant (FIGS. 4A-4C and Table 8). This is not surprising, given that these two tumor characteristics are interconnected. In fact, all metastatic PETs had a proliferation index >2%, while no tumor with a lower proliferation score was metastatic. Furthermore, miR-21 also distinguished between NF-PETs or WDEC with high (Ki-67>2%) and low (Ki-67≦2%) proliferation index. Another interesting observation is that miR-21 was also overexpressed in PACCs versus normal pancreas (Table 4).

Identification of Putative mRNA Targets for Differentially-Expressed microRNAs.

Figure 5:
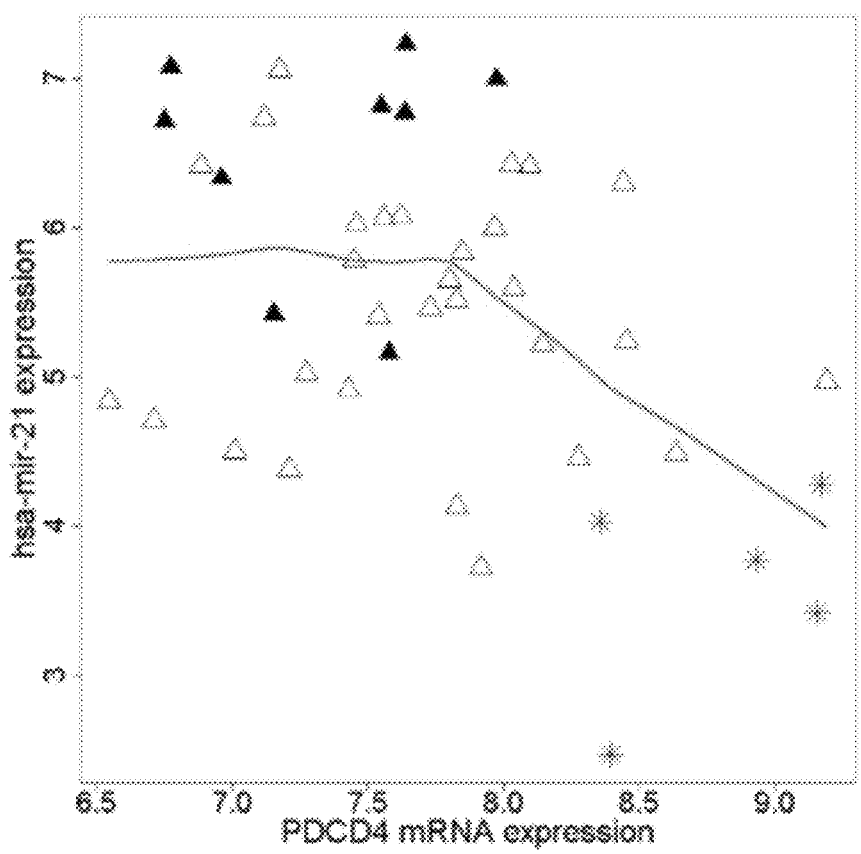
FIG. 5 is a plot showing the expression of miR-21 and PDCD4 mRNA in normal pancreas (*), metastatic (▲) and nonmetastatic (Δ) PET. A Robust locally weighted regression function has been used to fit a line among the data points. As is shown, there is an inverse correlation between the expression of miR-21 and its putative mRNA target PDCD4.

Three different programs (miRanda, TargetScan, PicTar, respectively available at www.microrna.org/mammalian/index.html; www.genes.mit.edu/targetscan/; and www.pictar.bio.nyu.edu) were used to identify predicted targets of selected microRNAs, namely miR-103/miR-107, miR-155, miR-204/miR-211 and miR-21. To increase the stringency of the analysis, we considered only target genes that were found from all three algorithms (Table 9). Because the same tumor samples and five normal pancreas analyzed for microRNA expression have also been evaluated for gene expression profiles with a custom EST microarray (data not shown), we attempted to assess the status of predicted mRNA targets in PET and normal tissue, as well as among PET with different clinicopathological characteristics. A two-sample-t-test analysis identified several putative target genes that were either downregulated or upregulated, namely 28 upregulated and 7 downregulated genes for miR-103/107, 2 upregulated and 2 downregulated genes for either miR-155 or miR-204/211, and 1 upregulated and 1 downregulated gene for miR-21 (Table 10). Notably, the mRNA expression of PDCD4 gene, a putative target of miR-21, was found to be downregulated in liver metastatic PET, as well as in tumors with high proliferation index, showing an inverse correlation with the expression of miR-21 (FIG. 5).

DISCUSSION

The results of the survey of microRNA expression profiles in normal pancreas, pancreatic endocrine tumors and acinar carcinomas may be summarized as follows:

i) a common microRNA expression profile distinguishes both endocrine and acinar tumors from normal pancreas;

ii) the expression of miR-103 and miR-107 associated with lack of expression of miR-155 discriminates tumors from normal;

iii) a limited set of microRNAs is specific to endocrine tumors and is possibly associated with the endocrine differentiation or tumorigenesis;

iv) miR-204 expression occurs primarily in insulinomas and correlates with immunohistochemical expression of insulin; and v) expression of miR-21 is strongly associated with proliferation index and liver metastasis.

Unsupervised hierarchical clustering of the expression profiles showed that both tumor types were separated from normal pancreas. Although PACCs fell into a unique cluster, this was part of the wider cluster including all PETs. While we identified many more differentially expressed microRNAs in PET versus normal than between acinar carcinomas versus normal, the vast majority of differentially expressed microRNAs in PACC were similarly altered in PET. It is worth noting that bulk pancreas is largely formed by acini and therefore represents the ideal normal counterpart for the analysis of acinar cell carcinomas, while pancreatic islet cells would represent the normal counterpart for pancreatic endocrine tumors. Unfortunately, we had no preparations of these cells available. Nonetheless, the finding of a largely concordant pattern of differentially expressed microRNAs between acinar and insular tumors, including 28 upregulated and 5 downregulated genes, suggests that this set common to both tumor types might be related to pancreatic neoplastic transformation. Providing additional support for this assertion, several microRNAs differentially expressed in both tumor types have been found to be differentially expressed in breast, colon and B-cell leukemia (Caldas, C., et al., Nat. Med. 11:712-14 (2005); Croce, C. M., and G. A. Calin, Cell 122:6-7 (2005); Iorio, M. V., et al., Cancer Res. 65:7065-70 (2005)). In addition, at least twenty of the differentially-expressed microRNAs in our tumors have been identified as having either growth related or apoptotic effects in the lung A549 or cervical HeLa carcinoma cell lines (Cheng, A. M., et al., Nucleic Acids Res. 33:1290-97 (2005)).

Furthermore, we observed, in both PACC and PET, the coordinate overexpression of miR-17, miR-20 and miR-92-1, which are contained in a polycistronic cluster. This miR-17-92 cluster has been described to act as an oncogene in association with c-MYC gene (He, L., et al., Nature 435:828-33 (2005)). Notably, overexpression of c-MYC has been reported in pancreatic endocrine tumors and also in hyperplastic islets, suggesting its involvement in the early phases of insular tumorigenesis (Pavelic, K., et al., Anticancer Res. 16:1707-17 (1996)). In addition, induction of MYC in islet or acinar cells of mouse in in vitro or in vivo models produces endocrine tumors (Katic, M., et al., Carcinogenesis 20:1521-27 (1999); Lewis, B. C., et al., Genes Dev. 17:3127-38 (2003)) or mixed acinar/ductal adenocarcinomas (Sandgren, E. P., et al., Proc. Natl. Acad. Sci. USA 88:93-97 (1991), respectively, while suppression of MYC-induced apoptosis leads to islet cells carcinoma (Pelengaris, S., et al., Cell 109: 321-34 (2002)).

The expression of the two highly homologous miR-103 and miR-107 microRNAs together with the lack of expression of miR-155 was distinctive of tumors vs. normal pancreatic samples. Interestingly, miR-103/107 have been found to be overexpressed in several tumor types (U.S. application Ser. No. 12/160,061; entitled "Micro-RNA-Based Methods and Compositions for the Diagnosis and Treatment of Solid Cancers", by Stefano Volinia, George A. Calin and Carlo M. Croce; filed on same date as the subject application; the teachings of which are incorporated herein by reference in their entirety). The finding that miR-155 was expressed in normal pancreas but was underexpressed or not expressed in both PET and PACC is rather interesting considering that overexpression of miR-155 has been observed in lymphomas (Caldas, C., et al., Nat. Med. 11:712-14 (2005); Croce, C. M., and G. A. Calin, Cell 122:6-7 (2005)) and breast cancer (Iorio, M. V., et al., Cancer Res. 65:7065-70 (2005)), a finding that has led to speculation that miR-155 may be an oncogenic microRNA (Croce, C. M., and G. A. Calin, Cell 122:6-7 (2005)). This may not be unexpected, as microRNAs expressed in adults are tissue-specific (Babak, T., et al., RNA 10:1813-19 (2004)) and the consequences of microRNA misexpression is highly dependent on the cell-specific expression pattern of mRNAs that are microRNA regulated (Cheng, A. M., et al., Nucleic Acids Res. 33:1290-97 (2005)).

Ten microRNAs were peculiarly overexpressed in PET and differentiated this tumor from both PACC and normal pancreas. These included miR-99a, miR-99b, miR-100, miR-125a, miR-125b-1, miR-125b-2, miR-129-2, miR-130a, miR-132, and miR-342. These microRNAs may be characteristic of either endocrine differentiation or endocrine tumorigenesis. On the other hand, no microRNA was found to be specifically upregulated or downregulated in PACC, although the limited number of PACC samples may have affected the power of the analysis.

Although the microRNA profiles were almost indistinguishable between insulinomas and nonfunctioning endocrine tumors, the overexpression of the two closely related microRNAs, namely miR-204 and miR-211, was largely restricted to insulinomas. Of great interest, miR-204 expression correlated with the immunohistochemical expression of insulin. In this respect, miR-375 has been recently reported to be specifically expressed in mouse pancreatic islets and to function as a negative regulator of insulin exocytosis (Poy, M. N., et al., Nature 432:226-30 (2004)). Our data showed that this microRNA is expressed in human normal pancreas, as well as in acinar cell and endocrine tumors. However, no difference was found in its expression level between insulinomas and nonfunctioning endocrine tumors.

We also determined if microRNA expression was correlated with the clinical characteristics of PETs. Our results showed that miR-21 overexpression is associated with both enhanced Ki-67 proliferation index and liver metastasis. miR-21 overexpression has been observed in several cancers, including glioblastoma, breast, lung and colon cancers (Caldas, C., et al., Nat. Med. 11:712-14 (2005); Croce, C. M., and G. A. Calin, Cell 122:6-7 (2005)). A cancer-related function of miR-21 is also supported by knockdown experiments in glioblastoma cell lines showing that this microRNA has an anti-apoptotic function (Chan, J. A., et al., Cancer Res. 65:6029-33 (2005)). In this respect, the programmed cell death 4 (PDCD4) gene, putatively targeted by miR-21, was found to be significantly down-regulated in metastatic and high proliferative PET samples, and showed an inverse correlation with the expression of miR-21. This gene has been reported to act as a tumor suppressor through activation of p21$^{waf1}$ and inhibition of transcription factor complex AP-1; the latter controls genes that have been implied in cellular invasion and metastatic progression (Jansen, A. P., et al., *Mol. Cancer. Ther.* 3:103-10 (2004)). Furthermore, PDCD4 expression is lost in progressed carcinomas of lung, breast, colon and prostate cancer (Goke, R., et al., *Am. J. Physiol. Cell Physiol.* 287:C1541-46 (2004)), and notably, a tumor suppressor role for PDCD4 has been also reported in a model of neuroendocrine tumor cells (Goke, R., et al., *Ann. N.Y. Acad. Sci.* 1014:220-21 (2004)).

Differentially-expressed microRNAs in PETs showed a nonrandom distribution among chromosomal arms and most of the microRNAs located at chromosomal arms 5q, 7q, 13q and 19p were overexpressed. This finding may be due to either the frequent association of microRNAs in polycistronic clusters (Baskerville, S. and D. P. Bartel, *RNA* 11:241-47 (2005); Altuvia, Y., et al., *Nucleic Acids Res.* 33:2697-2706 (2005)) or the amplification of the chromosomal arms containing these microRNAs. Our analysis suggests that both phenomena can be involved in PET. In fact, the correlation coefficients measured between pairs of microRNAs within clusters differed significantly from those between pairs of microRNAs outside the clusters. These data confirm in PET the general observation that grouped microRNA genes show coordinate expression (Baskerville, S, and D. P. Bartel, *RNA* 11:241-47 (2005); Altuvia, Y., et al., *Nucleic Acids Res.* 33:2697-2706 (2005)).

MicroRNAs exert their biological effects by targeting specific mRNAs for degradation or translational inhibition. In order to get insights into the biological implications of the most interesting microRNAs showing altered expression in pancreatic tumors, e.g., miR-103/miR-107, miR-155, miR-204/miR-211 and miR-21, we searched predicted targets that were in common among those identified by three different algorithms (see RESULTS). Then, to evaluate if there was a correlation between the expression of microRNAs and that of their predicted targets, we took advantage of the EST expression profiles of the same tumor and normal samples. Among the selected targets that were contained in our EST microarray, we found several upregulated and downregulated genes. Interestingly, the predicted target genes of miR-103/107 were overexpressed more frequently than expected. This finding parallels that of Babak et al., who reported a low correlation between microRNA expression and their predicted mRNA targets in a set of 17 different mouse tissues (Babak, T., et al., *RNA* 10:1813-19 (2004)). This supports the currently favored model that most microRNAs act more likely through translational inhibition without mRNA degradation (Bartel, D. P., *Cell* 116:281-97 (2004)).

In conclusion, the results described herein suggest that alteration in microRNA expression is related to endocrine and acinar neoplastic transformation and progression of malignancy.

The relevant teachings of all publications cited herein that have not explicitly been incorporated by reference, are incorporated herein by reference in their entirety. In addition, the nucleotide sequences (e.g., microRNA nucleotide sequences) identified herein by reference to specific Accession Number are also incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining whether a subject has, or is at risk for developing, pancreatic cancer, wherein the method comprises:
   extracting from the subject a test sample comprising at least one miR-155 gene product;
   measuring the level of the miR-155 gene product in the test sample;
   determining whether the subject has, or is at risk for developing, pancreatic cancer by comparing the level of the miR-155 gene product in the test sample to the level of a corresponding miR gene product in a control sample,
   correlating a decrease in the level of the miR-155 gene product in the test sample, relative to the level of the corresponding miR gene product in the control sample, as being indicative of a diagnosis of the subject either having, or being at risk for developing, pancreatic cancer.

2. The method according to claim 1, wherein the test sample further comprises at least one miR-103 gene product, and wherein the method further comprises:
   measuring the level of the miR-103 gene product in the test sample;
   determining whether the subject has, or is at risk for developing, pancreatic cancer by comparing the level of the miR-103 gene product in the test sample to the level of a corresponding miR gene product in a control sample,
   correlating an increase in the level of the miR-103 gene product in the test sample, relative to the level of the corresponding miR gene product in the control sample, as being indicative of a diagnosis of the subject either having, or being at risk for developing, pancreatic cancer.

3. The method according to claim 1, wherein the test sample further comprises at least one miR-107 gene product, and wherein the method further comprises:
   measuring the level of the miR-107 gene product in the test sample;
   determining whether the subject has, or is at risk for developing, pancreatic cancer by comparing the level of the miR-107 gene product in the test sample to the level of a corresponding miR gene product in a control sample,
   correlating an increase in the level of the miR-107 gene product in the test sample, relative to the level of the corresponding miR gene product in the control sample, as being indicative of a diagnosis of the subject either having, or being at risk for developing, pancreatic cancer.

4. The method according to claim 1, wherein the test sample further comprises at least one miR-103 gene product and at least one miR-107 gene product, and wherein the method further comprises:
   measuring the level of the miR-103 gene product and the level of the miR-107 gene product in the test sample;
   determining whether the subject has, or is at risk for developing, pancreatic cancer by comparing the level of the miR-103 gene product and the level of the miR-107 gene product in the test sample to the level of a corresponding miR gene product in a control sample,
   correlating an increase in the level of the miR-103 gene product and an increase in the level of the miR-107 gene product in the test sample, relative to the level of the corresponding miR gene product in the control sample, as being indicative of a diagnosis of the subject either having, or being at risk for developing, pancreatic cancer.

5. The method according to claim 1, wherein the measuring the level of the miR-155 gene product in the test sample is carried out by analyzing the test sample with a RT-PCR, a microarray and/or a Northern blot electrophoretic device.

6. The method according to claim 2, wherein the measuring the level of the miR-155 gene product and the level of the miR-103 gene product in the test sample is carried out by analyzing the test sample with a RT-PCR, a microarray and/or a Northern blot electrophoretic device.

7. The method according to claim 3, wherein the measuring the level of the miR-155 gene product and the level of the miR-107 gene product in the test sample is carried out by analyzing the test sample with a RT-PCR, a microarray and/or a Northern blot electrophoretic device.

8. The method according to claim 4, wherein the measuring the level of the miR-155 gene product, the level of the miR-103 gene product, and the level of the miR-107 gene product in the test sample is carried out by analyzing the test sample with a RT-PCR, a microarray and/or a Northern blot electrophoretic device.

9. The method according to claim 1, further comprising:
confirming diagnosis by searching, or periodically monitoring, for symptoms which are associated with pancreatic cancer and exhibited by the subject when there is a decrease in the level of the miR-155 gene product in the test sample, relative to the level of the corresponding miR gene product in the control sample.

10. The method according to claim 2, further comprising:
confirming diagnosis by searching, or periodically monitoring, for symptoms which are associated with pancreatic cancer and exhibited by the subject when there is a decrease in the level of the miR-155 gene product and an increase in the level of the miR-103 gene product in the test sample, relative to the level of the corresponding miR gene product in the control sample.

11. The method according to claim 3, further comprising:
confirming diagnosis by searching, or periodically monitoring, for symptoms which are associated with pancreatic cancer and exhibited by the subject when there is a decrease in the level of the miR-155 gene product and an increase in the level of the miR-107 gene product in the test sample, relative to the level of the corresponding miR gene product in the control sample.

12. The method according to claim 4, further comprising:
confirming diagnosis by searching, or periodically monitoring, for symptoms which are associated with pancreatic cancer and exhibited by the subject when there is a decrease in the level of the miR-155 gene product, an increase in the level of the miR-103 gene product, and an increase in the level of the miR-107 gene product in the test sample, relative to the level of the corresponding miR gene product in the control sample.

13. The method according to claim 1, wherein the pancreatic cancer is a pancreatic endocrine tumor (PET).

14. The method according to claim 1, wherein the pancreatic cancer is at least one pancreatic endocrine tumor (PET) selected from the group consisting of gastrinoma, insulinoma, somatostatinoma, VIPoma, and glucagonoma.

15. The method according to claim 13, further comprising:
confirming diagnosis by searching, or periodically monitoring, for symptoms of hormone hypersecretion associated with PET and exhibited by the subject when there is a decrease in the level of the miR-155 gene product in the test sample, relative to the level of the corresponding miR gene product in the control sample.

16. The method according to claim 15, wherein the hormone is at least one hypersecreted hormone selected from the group consisting of gastrin, insulin, somatostatin, vasoactive intestinal polypeptide (VIP), and glucagon.

17. The method according to claim 2, wherein the pancreatic cancer is a pancreatic endocrine tumor (PET).

18. The method according to claim 2, wherein the pancreatic cancer is at least one pancreatic endocrine tumor (PET) selected from the group consisting of gastrinoma, insulinoma, somatostatinoma, VIPoma, and glucagonoma.

19. The method according to claim 17, further comprising:
confirming diagnosis by searching, or periodically monitoring, for symptoms of hormone hypersecretion associated with PET and exhibited by the subject when there is a decrease in the level of the miR-155 gene product and an increase in the level of the miR-103 gene product in the test sample, relative to the level of the corresponding miR gene product in the control sample.

20. The method according to claim 19, wherein the hormone is at least one hypersecreted hormone selected from the group consisting of gastrin, insulin, somatostatin, vasoactive intestinal polypeptide (VIP), and glucagon.

21. The method according to claim 3, wherein the pancreatic cancer is a pancreatic endocrine tumor (PET).

22. The method according to claim 3, wherein the pancreatic cancer is at least one pancreatic endocrine tumor (PET) selected from the group consisting of gastrinoma, insulinoma, somatostatinoma, VIPoma, and glucagonoma.

23. The method according to claim 21, further comprising:
confirming diagnosis by searching, or periodically monitoring, for symptoms of hormone hypersecretion associated with PET and exhibited by the subject when there is a decrease in the level of the miR-155 gene product and an increase in the level of the miR-107 gene product in the test sample, relative to the level of the corresponding miR gene product in the control sample.

24. The method according to claim 23, wherein the hormone is at least one hypersecreted hormone selected from the group consisting of gastrin, insulin, somatostatin, vasoactive intestinal polypeptide (VIP), and glucagon.

25. The method according to claim 4, wherein the pancreatic cancer is a pancreatic endocrine tumor (PET).

26. The method according to claim 4, wherein the pancreatic cancer is at least one pancreatic endocrine tumor (PET) selected from the group consisting of gastrinoma, insulinoma, somatostatinoma, VIPoma, and glucagonoma.

27. The method according to claim 25, further comprising:
confirming diagnosis by searching, or periodically monitoring, for symptoms of hormone hypersecretion associated with PET and exhibited by the subject when there is a decrease in the level of the miR-155 gene product, an increase in the level of the miR-103 gene product, and an increase in the level of the miR-107 gene product in the test sample, relative to the level of the corresponding miR gene product in the control sample.

28. The method according to claim 27, wherein the hormone is at least one hypersecreted hormone selected from the group consisting of gastrin, insulin, somatostatin, vasoactive intestinal polypeptide (VIP), and glucagon.

29. The method according to claim 1, further comprising:
communicating to the subject the diagnosis of having, or being at risk for developing, pancreatic cancer when there is a decrease in the level of the miR-155 gene product in the test sample, relative to the level of the corresponding miR gene product in the control sample.

30. The method according to claim 2, further comprising:
communicating to the subject the diagnosis of having, or being at risk for developing, pancreatic cancer when there is a decrease in the level of the miR-155 gene product and an increase in the level of the miR-103 gene product in the test sample, relative to the level of the corresponding miR gene product in the control sample.

31. The method according to claim 3, further comprising:
communicating to the subject the diagnosis of having, or being at risk for developing, pancreatic cancer when there is a decrease in the level of the miR-155 gene product and an increase in the level of the miR-107 gene product in the test sample, relative to the level of the corresponding miR gene product in the control sample.

32. The method according to claim 4, further comprising:
communicating to the subject the diagnosis of having, or being at risk for developing, pancreatic cancer when there is a decrease in the level of the at least miR-155 gene product, an increase in the level of the miR-103 gene product, and an increase in the level of the miR-107 gene product in the test sample, relative to the level of the corresponding miR gene product in the control sample.

33. The method according to claim 15, further comprising: communicating to the subject the diagnosis of having, or being at risk for developing, PET when there is a decrease in the level of the miR-155 gene product in the test sample, relative to the level of the corresponding miR gene product in the control sample, and symptoms of hormone hypersecretion associated PET are exhibited by the subject.

34. The method according to claim 19, further comprising: communicating to the subject the diagnosis of having, or being at risk for developing, PET when there is a decrease in the level of the miR-155 gene product and an increase in the level of the miR-103 gene product in the test sample, relative to the level of the corresponding miR gene product in the control sample, and symptoms of hormone hypersecretion associated PET are exhibited by the subject.

35. The method according to claim 23, further comprising: communicating to the subject the diagnosis of having, or being at risk for developing, PET when there is a decrease in the level of the miR-155 gene product and an increase in the level of the miR-107 gene product in the test sample, relative to the level of the corresponding miR gene product in the control sample, and symptoms of hormone hypersecretion associated PET are exhibited by the subject.

36. The method according to claim 27, further comprising: communicating to the subject the diagnosis of having, or being at risk for developing, PET when there is a decrease in the level of the at least miR-155 gene product, an increase in the level of the miR-103 gene product, and an increase in the level of the miR-107 gene product in the test sample, relative to the level of the corresponding miR gene product in the control sample, and symptoms of hormone hypersecretion associated PET are exhibited by the subject.

37. A method of determining whether a subject has, or is at risk for developing, pancreatic cancer, wherein the method comprises:
isolating RNA from a test sample extracted from the subject;
reverse transcribing the RNA isolated from the test sample to provide at least one target oligodeoxynucleotide;
hybridizing the at least one target oligodeoxynucleotide to a microarray comprising at least one miR-155 miRNA-specific probe oligonucleotide to provide a hybridization profile for the test sample;
determining whether the subject has, or is at risk for developing, pancreatic cancer by comparing the signal of the miR-155 miRNA in the hybridization profile for the test sample to the signal of a corresponding miRNA in the hybridization profile for a control sample,
correlating a downregulated signal of the miR-155 miRNA in the test sample, relative to the signal of the corresponding miRNA in the control sample, as being indicative of a diagnosis of the subject either having, or being at risk for developing, pancreatic cancer.

38. The method according to claim 37, wherein the method further comprises:
hybridizing the target oligodeoxynucleotide to the microarray which further comprises at least one miR-103 miRNA-specific probe oligonucleotide to provide a hybridization profile for the test sample;
determining whether the subject has, or is at risk for developing, pancreatic cancer by comparing the signal of the miR-103 miRNA in the hybridization profile for the test sample to the signal of a corresponding miRNA in the hybridization profile for a control sample,
correlating an upregulated signal of the miR-103 miRNA in the test sample, relative to the signal of the corresponding miRNA in the control sample, as being indicative of a diagnosis of the subject either having, or being at risk for developing, pancreatic cancer.

39. The method according to claim 37, wherein the method further comprises:
hybridizing the target oligodeoxynucleotide to the microarray which further comprises at least one miR-107 miRNA-specific probe oligonucleotide to provide a hybridization profile for the test sample;
determining whether the subject has, or is at risk for developing, pancreatic cancer by comparing the signal of the miR-107 miRNA in the hybridization profile for the test sample to the signal of a corresponding miRNA in the hybridization profile for a control sample,
correlating an upregulated signal of the miR-107 miRNA in the test sample, relative to the signal of the corresponding miRNA in the control sample, as being indicative of a diagnosis of the subject either having, or being at risk for developing, pancreatic cancer.

40. The method according to claim 37, wherein the method further comprises:
hybridizing the target oligodeoxynucleotide to the microarray which further comprises at least one miR-103 miRNA-specific probe oligonucleotide and at least one miR-107 miRNA-specific probe oligonucleotide to provide a hybridization profile for the test sample;
determining whether the subject has, or is at risk for developing, pancreatic cancer by comparing the signal of the miR-103 miRNA and the signal of the miR-107 miRNA in the hybridization profile for the test sample to the signal of a corresponding miRNA in the hybridization profile for a control sample,
correlating an upregulated signal of the miR-103 miRNA and an upregulated signal of the miR-107 miRNA in the test sample, relative to the signal of the corresponding miRNA in the control sample, as being indicative of a diagnosis of the subject either having, or being at risk for developing, pancreatic cancer.

41. The method according to claim 37, further comprising: confirming diagnosis by searching, or periodically monitoring, for symptoms which are associated with pancreatic cancer and exhibited by the subject when there is a downregulated signal of the miR-155 miRNA in the test sample, relative to the signal of the corresponding miRNA in the control sample.

42. The method according to claim 38, further comprising: confirming diagnosis by searching, or periodically monitoring, for symptoms which are associated with pancreatic cancer and exhibited by the subject when there is a downregulated signal of the miR-155 miRNA and an upregulated signal of the miR-103 miRNA in the test sample, relative to the signal of the corresponding miRNA in the control sample.

43. The method according to claim 39, further comprising: confirming diagnosis by searching, or periodically monitoring, for symptoms which are associated with pancreatic cancer and exhibited by the subject when there is a downregulated signal of the miR-155 miRNA and an upregulated signal of the miR-107 miRNA in the test sample, relative to the signal of the corresponding miRNA in the control sample.

44. The method according to claim 40, further comprising:
confirming diagnosis by searching, or periodically monitoring, for symptoms which are associated with pancreatic cancer and exhibited by the subject when there is a downregulated signal of the miR-155 miRNA, an upregulated signal of the miR-103 miRNA, and an upregulated signal of the miR-107 miRNA in the test sample, relative to the signal of the corresponding miRNA in the control sample.

45. The method according to claim 37, wherein the pancreatic cancer is a pancreatic endocrine tumor (PET).

46. The method according to claim 37, wherein the pancreatic cancer is at least one pancreatic endocrine tumor (PET) selected from the group consisting of gastrinoma, insulinoma, somatostatinoma, VIPoma, and glucagonoma.

47. The method according to claim 45, further comprising:
confirming diagnosis by searching, or periodically monitoring, for symptoms of hormone hypersecretion associated with PET and exhibited by the subject when there is a downregulated signal of the miR-155 miRNA in the test sample, relative to the signal of the corresponding miRNA in the control sample.

48. The method according to claim 47, wherein the hormone is at least one hypersecreted hormone selected from the group consisting of gastrin, insulin, somatostatin, vasoactive intestinal polypeptide (VIP), and glucagon.

49. The method according to claim 38, wherein the pancreatic cancer is a pancreatic endocrine tumor (PET).

50. The method according to claim 38, wherein the pancreatic cancer is at least one pancreatic endocrine tumor (PET) selected from the group consisting of gastrinoma, insulinoma, somatostatinoma, VIPoma, and glucagonoma.

51. The method according to claim 49, further comprising:
confirming diagnosis by searching, or periodically monitoring, for symptoms of hormone hypersecretion associated with PET and exhibited by the subject when there is a downregulated signal of the miR-155 miRNA and an upregulated signal of the miR-103 miRNA in the test sample, relative to the signal of the corresponding miRNA in the control sample.

52. The method according to claim 51, wherein the hormone is at least one hypersecreted hormone selected from the group consisting of gastrin, insulin, somatostatin, vasoactive intestinal polypeptide (VIP), and glucagon.

53. The method according to claim 39, wherein the pancreatic cancer is a pancreatic endocrine tumor (PET).

54. The method according to claim 39, wherein the pancreatic cancer is at least one pancreatic endocrine tumor (PET) selected from the group consisting of gastrinoma, insulinoma, somatostatinoma, VIPoma, and glucagonoma.

55. The method according to claim 53, further comprising:
confirming diagnosis by searching, or periodically monitoring, for symptoms of hormone hypersecretion associated with PET and exhibited by the subject when there is a downregulated signal of the miR-155 miRNA and an upregulated signal of the miR-107 miRNA in the test sample, relative to the signal of the corresponding miRNA in the control sample.

56. The method according to claim 55, wherein the hormone is at least one hypersecreted hormone selected from the group consisting of gastrin, insulin, somatostatin, vasoactive intestinal polypeptide (VIP), and glucagon.

57. The method according to claim 40, wherein the pancreatic cancer is a pancreatic endocrine tumor (PET).

58. The method according to claim 40, wherein the pancreatic cancer is at least one pancreatic endocrine tumor (PET) selected from the group consisting of gastrinoma, insulinoma, somatostatinoma, VIPoma, and glucagonoma.

59. The method according to claim 57, further comprising:
confirming diagnosis by searching, or periodically monitoring, for symptoms of hormone hypersecretion associated with PET and exhibited by the subject when there is a downregulated signal of the miR-155 miRNA, an upregulated signal of the miR-103 miRNA, and an upregulated signal of the miR-107 miRNA in the test sample, relative to the signal of the corresponding miRNA in the control sample.

60. The method according to claim 59, wherein the hormone is at least one hypersecreted hormone selected from the group consisting of gastrin, insulin, somatostatin, vasoactive intestinal polypeptide (VIP), and glucagon.

61. The method according to claim 37, further comprising:
communicating to the subject the diagnosis of having, or being at risk for developing, pancreatic cancer when there is a downregulated signal of the miR-155 miRNA in the test sample, relative to the signal of the corresponding miRNA in the control sample.

62. The method according to claim 38, further comprising:
communicating to the subject the diagnosis of having, or being at risk for developing, pancreatic cancer when there is a downregulated signal of the miR-155 miRNA and an upregulated signal of the miR-103 miRNA in the test sample, relative to the signal of the corresponding miRNA in the control sample.

63. The method according to claim 39, further comprising:
communicating to the subject the diagnosis of having, or being at risk for developing, pancreatic cancer when there is a downregulated signal of the miR-155 miRNA and an upregulated signal of the miR-107 miRNA in the test sample, relative to the signal of the corresponding miRNA in the control sample.

64. The method according to claim 40, further comprising:
communicating to the subject the diagnosis of having, or being at risk for developing, pancreatic cancer when there is a downregulated signal of the miR-155 miRNA, an upregulated signal of the miR-103 miRNA and an upregulated signal of the miR-107 miRNA in the test sample, relative to the signal of the corresponding miRNA in the control sample.

* * * * *

SEQUENCE LISTING

<160> NUMBER OF SEQ ID NOS: 498

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuaggguc acaccacca cugggagaua      60 acauacaau cuacugucuu uccuaacgug                                      90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu     60
ccuagcuuuc cu                                                        72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acauacaau      60

-continued cuacugucuu uccu                                              74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag    60
auaacuguac agccuccuag cuuuccuugg gucuugcacu aaacaac                 107

<210> SEQ ID NO 5
<211> LENGTH: 85
<212> TYPE: RNA
<213> ORGANISM: Homo sapiens

<400> SEQUENCE: 5
ggcgggguga gguaguaggu ugugugguuu cagggcagug auguugcccc ucggaagaua    60
acuauacaac cuacugccuu cccug                                         85

<210> SEQ ID NO 6
<211> LENGTH: 84
<212> TYPE: RNA
<213> ORGANISM: Homo sapiens

<400> SEQUENCE: 6
gcauccgggu ugagguagua gguuguaugg uuuagaguua cacccuggga guuaacugua    60
caaccuucua gcuuuccuug gagc                                          84

<210> SEQ ID NO 7
<211> LENGTH: 87
<212> TYPE: RNA
<213> ORGANISM: Homo sapiens

<400> SEQUENCE: 7
ccuaggaaga gguaguaggu ugcauaguuu uagggcaggg auuuugccca caaggaggua    60
acuauacgac cugcugccuu ucuuagg                                       87

<210> SEQ ID NO 8
<211> LENGTH: 85
<212> TYPE: RNA
<213> ORGANISM: Homo sapiens

<400> SEQUENCE: 8
cuaggaagag guaguaguuu gcauaguuuu agggcaaaga uuuugcccac aaguaguuag    60
cuauacgacc ugcagccuuu uguag                                         85

<210> SEQ ID NO 9
<211> LENGTH: 85
<212> TYPE: RNA
<213> ORGANISM: Homo sapiens

<400> SEQUENCE: 9
cuggcugagg uaguaguuug ugcuguuggu cggguuguga cauugcccgc uguggagaua    60
acugcgcaag cuacugccuu gcuag                                         85

<210> SEQ ID NO 10
<211> LENGTH: 79
<212> TYPE: RNA
<213> ORGANISM: Homo sapiens

```
<400> SEQUENCE: 10
cccgggcuga gguaggaggu uguauaguug aggaggacac ccaaggagau cacuauacgg    60
ccuccuagcu uuccccagg                                                79

<210> SEQ ID NO 11
<211> LENGTH: 87
<212> TYPE: RNA
<213> ORGANISM: Homo sapiens

<400> SEQUENCE: 11
ucagagugag guaguagauu guauaguugu gggguaguga uuuuacccug uucaggagau    60
aacuauacaa ucuauugccu ucccuga                                       87

<210> SEQ ID NO 12
<211> LENGTH: 89
<212> TYPE: RNA
<213> ORGANISM: Homo sapiens

<400> SEQUENCE: 12
cugugggaug agguaguaga uuguauaguu gugggguagu gauuuuaccc uguucaggag    60
auaacuauac aaucuauugc cuucccuga                                     89

<210> SEQ ID NO 13
<211> LENGTH: 85
<212> TYPE: RNA
<213> ORGANISM: Homo sapiens

<400> SEQUENCE: 13
cugugggaug agguaguaga uuguauaguu uuagggucau accccaucuu ggagauaacu    60
auacagucua cugucuuucc cacgg                                         85

<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg    60
guacaggaga uaacuguaca ggccacugcc uugccaggaa cagcgcgc               108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cggguuguga cauugcccgc uguggagaua    60
acugcgcaag cuacugccuu gcuag                                         85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu    60
aaagaaguau guauuuuugg uaggc                                         85
```

```
<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauaugaac      60
auacaaugcu auggaaugua aagaaguaug uauuuuuggu aggcaaua                  108

<210> SEQ ID NO 18
<211> LENGTH: 85
<212> TYPE: RNA
<213> ORGANISM: Homo sapiens

<400> SEQUENCE: 18
gccugcuugg gaaacauacu ucuuuauaug cccauaugga ccugcuaagc uauggaaugu      60
aaagaaguau guaucucagg ccggg                                            85

<210> SEQ ID NO 19
<211> LENGTH: 71
<212> TYPE: RNA
<213> ORGANISM: Homo sapiens

<400> SEQUENCE: 19
ugggaaacau acuucuuuau augcccauau ggaccugcua agcuauggaa uguaaagaag      60
uauguaucuc a                                                           71

<210> SEQ ID NO 20
<211> LENGTH: 85
<212> TYPE: RNA
<213> ORGANISM: Homo sapiens

<400> SEQUENCE: 20
accuacucag aguacauacu ucuuuaugua cccauaugaa cauacaaugc uauggaaugu      60
aaagaaguau guauuuuugg uaggc                                            85

<210> SEQ ID NO 21
<211> LENGTH: 108
<212> TYPE: RNA
<213> ORGANISM: Homo sapiens

<400> SEQUENCE: 21
uggauguugg ccuaguucug uguggaagac uagugauuuu guuguuuuua gauaacuaaa      60
ucgacaacaa aucacagucu gccauauggc acaggccaug ccucuaca                  108

<210> SEQ ID NO 22
<211> LENGTH: 110
<212> TYPE: RNA
<213> ORGANISM: Homo sapiens

<400> SEQUENCE: 22
uuggauguug gccuaguucu guguggaaga cuagugauuu uguuguuuuu agauaacuaa      60
aucgacaaca aaucacaguc ugccauaugg cacaggccau gccucuacag               110

<210> SEQ ID NO 23
<211> LENGTH: 110
<212> TYPE: RNA
<213> ORGANISM: Homo sapiens

<400> SEQUENCE: 23
cuggauacag aguggaccgg cuggccccau cuggaagacu agugauuuug uuguugucuu      60
```

```
acugcgcuca acaacaaauc ccagucuacc uaauggugcc agccaucgca            110
```

<210> SEQ ID NO 24
<211> LENGTH: 110
<212> TYPE: RNA
<213> ORGANISM: Homo sapiens

<400> SEQUENCE: 24

```
agauuagagu ggcugugguc uagugcugug uggaagacua gugauuuugu uguucugaug    60
uacuacgaca acaagucaca gccggccuca uagcgcagac ucccuucgac              110
```

<210> SEQ ID NO 25
<211> LENGTH: 89
<212> TYPE: RNA
<213> ORGANISM: Homo sapiens

<400> SEQUENCE: 25

```
cgggguuggu uguuaucuuu gguuaucuag cuguaugagu gguguggagu cuucauaaag    60
cuagauaacc gaaaguaaaa auaacccca                                     89
```

<210> SEQ ID NO 26
<211> LENGTH: 87
<212> TYPE: RNA
<213> ORGANISM: Homo sapiens

<400> SEQUENCE: 26

```
ggaagcgagu uguuaucuuu gguuaucuag cuguaugagu guauuggucu ucauaaagcu    60
agauaaccga aaguaaaaac uccuuca                                       87
```

<210> SEQ ID NO 27
<211> LENGTH: 90
<212> TYPE: RNA
<213> ORGANISM: Homo sapiens

<400> SEQUENCE: 27

```
ggaggcccgu uucucucuuu gguuaucuag cuguaugagu gccacagagc cgucauaaag    60
cuagauaacc gaaaguagaa augauucuca                                    90
```

<210> SEQ ID NO 28
<211> LENGTH: 110
<212> TYPE: RNA
<213> ORGANISM: Homo sapiens

<400> SEQUENCE: 28

```
gaucugucug ucuucuguau auacccugua gauccgaauu uguguaagga auuuuguggu    60
cacaaauucg uaucuagggg aauauguagu ugacauaaac acuccgcucu              110
```

<210> SEQ ID NO 29
<211> LENGTH: 110
<212> TYPE: RNA
<213> ORGANISM: Homo sapiens

<400> SEQUENCE: 29

```
ccagagguug uaacguuguc uauauauacc cuguagaacc gaauugugu gguauccgua     60 uagucacaga uucgauucua ggggaauaua uggucgaugc aaaaacuuca              110
```

<210> SEQ ID NO 30
<211> LENGTH: 108
<212> TYPE: RNA
<213> ORGANISM: Homo sapiens

```
<400> SEQUENCE: 30
gcgcgaaugu guguuuaaaa aaauaaaac cuuggaguaa aguagcagca cauaaugguu      60
uguggauuuu gaaaaggugc aggccauauu gugcugccuc aaaaauac                 108

<210> SEQ ID NO 31
<211> LENGTH: 83
<212> TYPE: RNA
<213> ORGANISM: Homo sapiens

<400> SEQUENCE: 31
ccuuggagua aaguagcagc acauaauggu uuguggauuu ugaaaaggug caggccauau    60
ugugcugccu caaaaauaca agg                                           83

<210> SEQ ID NO 32
<211> LENGTH: 64
<212> TYPE: RNA
<213> ORGANISM: Homo sapiens

<400> SEQUENCE: 32
cuguagcagc acaucauggu uuacaugcua agucaagau gcgaaucauu auuugcugcu     60
cuag                                                                64

<210> SEQ ID NO 33
<211> LENGTH: 98
<212> TYPE: RNA
<213> ORGANISM: Homo sapiens

<400> SEQUENCE: 33
uugaggccuu aaaguacugu agcagcacau cauggUuuac augcuacagu caagaugcga    60
aucauuauuu gcugcucuag aaauuuaagg aaauucau                           98

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu    60
auuaacugug cugcugaagu aagguugac                                     89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauauuaaa caccaauauu    60
acugugcugc uuuaguguga c                                             81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuaagauuc uaaaauuauc uccaguauua    60
acugugcugc ugaaguaagg u                                             81
```

```
<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga      60
aggcacuugu agcauuaugg ugac                                            84

<210> SEQ ID NO 38
<211> LENGTH: 71
<212> TYPE: RNA
<213> ORGANISM: Homo sapiens

<400> SEQUENCE: 38
uguucuaagg ugcaucuagu gcagauagug aaguagauua gcaucuacug cccuaagugc      60
uccuucuggc a                                                          71

<210> SEQ ID NO 39
<211> LENGTH: 81
<212> TYPE: RNA
<213> ORGANISM: Homo sapiens

<400> SEQUENCE: 39
uuuuuguucu aaggugcauc uagugcagau agugaaguag auuagcaucu acugcccuaa      60
gugcuccuuc uggcauaaga a                                               81

<210> SEQ ID NO 40
<211> LENGTH: 82
<212> TYPE: RNA
<213> ORGANISM: Homo sapiens

<400> SEQUENCE: 40 gcagucccucu guuaguuuug cauaguugca cuacaagaag aauguaguug ugcaaaucua     60
ugcaaaacug augguggccu gc                                              82

<210> SEQ ID NO 41
<211> LENGTH: 80
<212> TYPE: RNA
<213> ORGANISM: Homo sapiens

<400> SEQUENCE: 41
caguccucug uuaguuuugc auaguugcac uacaagaaga auguaguugu gcaaaucuau      60
gcaaaacuga ugguggccug                                                 80

<210> SEQ ID NO 42
<211> LENGTH: 87
<212> TYPE: RNA
<213> ORGANISM: Homo sapiens

<400> SEQUENCE: 42 cacuguucua igguuaguuu ugcagguuug cauccagcug ugugauauuc ugcugugcaa      60
auccaugcaa aacugacugu gguagug                                         87

<210> SEQ ID NO 43
<211> LENGTH: 96
<212> TYPE: RNA
<213> ORGANISM: Homo sapiens

<400> SEQUENCE: 43
acauugcuac uuacaauuag uuuugcaggu uugcauuuca gcguauauau guauaugugg      60
```
cugugcaaau ccaugcaaaa cugauuguga uaaugu                                    96

<210> SEQ ID NO 44
<211> LENGTH: 80
<212> TYPE: RNA
<213> ORGANISM: Homo sapiens

<400> SEQUENCE: 44 uucuagguu aguuuugcag guuugcaucc agcuguguga uauucugcug ugcaaaucca          60
ugcaaaacug acugugguag                                                     80

<210> SEQ ID NO 45
<211> LENGTH: 81
<212> TYPE: RNA
<213> ORGANISM: Homo sapiens

<400> SEQUENCE: 45
uuacaauuag uuuugcaggu uugcauuuca gcguauauau guauaugugg cugugcaaau          60
ccaugcaaaa cugauuguga u                                                   81

<210> SEQ ID NO 46
<211> LENGTH: 71
<212> TYPE: RNA
<213> ORGANISM: Homo sapiens

<400> SEQUENCE: 46
guagcacuaa agugcuuaua gugcagguag uguuuaguua ucuacugcau uaugagcacu          60
uaaaguacug c                                                              71

<210> SEQ ID NO 47
<211> LENGTH: 72
<212> TYPE: RNA
<213> ORGANISM: Homo sapiens

<400> SEQUENCE: 47
ugucggguag cuuaucagac ugauguugac uguugaaucu cauggcaaca ccagucgaug          60
ggcugucuga ca                                                             72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc          60
gaugggcugu cugacauuuu g                                                   81

<210> SEQ ID NO 49
<211> LENGTH: 85
<212> TYPE: RNA
<213> ORGANISM: Homo sapiens

<400> SEQUENCE: 49
ggcugagccg caguaguucu ucagguggcaa gcuuuauguc cugacccagc uaaagcugcc         60
aguugaagaa cuguugcccu cugcc                                               85

<210> SEQ ID NO 50
<211> LENGTH: 73
<212> TYPE: RNA
<213> ORGANISM: Homo sapiens

```
<400> SEQUENCE: 50
ggccggcugg gguuccuggg gaugggauuu gcuuccuguc acaaaucaca uugccaggga    60
uuuccaaccg acc                                                      73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugugacuuaa gauuaaaauc    60
acauugccag ggauuaccac gcaaccacga ccuuggc                            97

<210> SEQ ID NO 52
<211> LENGTH: 81
<212> TYPE: RNA
<213> ORGANISM: Homo sapiens

<400> SEQUENCE: 52
ccacggccgg cuggguucc uggggauggg auuugcuucc ugucacaaau cacauugcca    60
gggauuucca accgacccug a                                             81

<210> SEQ ID NO 53
<211> LENGTH: 68
<212> TYPE: RNA
<213> ORGANISM: Homo sapiens

<400> SEQUENCE: 53
cuccggugcc uacugagcug auaucaguuc ucauuuuaca cacuggcuca guucagcagg    60
aacaggag                                                            68

<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc    60
agcaggaaca ggg                                                      73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guugguuugu guacacuggc    60
ucaguucagc aggaacaggg g                                             81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca    60
ggaacagcau c                                                        71
```

```
<210> SEQ ID NO 57
<211> LENGTH: 84
<212> TYPE: RNA
<213> ORGANISM: Homo sapiens

<400> SEQUENCE: 57
ggccaguguu gagaggcgga acuugggca auugcuggac gcugcccugg gcauugcacu        60
ugucucgguc ugacagugcc ggcc                                              84

<210> SEQ ID NO 58
<211> LENGTH: 86
<212> TYPE: RNA
<213> ORGANISM: Homo sapiens

<400> SEQUENCE: 58
aggccguggc cucguucaag uaauccagga uaggcugugc agguccccaau ggccuaucuu       60 gguuacuugc acggggacgc gggccu                                            86

<210> SEQ ID NO 59
<211> LENGTH: 77
<212> TYPE: RNA
<213> ORGANISM: Homo sapiens

<400> SEQUENCE: 59
guggccucgu ucaaguaauc caggauaggc ugugcagguc ccaaugggcc uauucuuggu       60
uacuugcacg gggacgc                                                     77

<210> SEQ ID NO 60
<211> LENGTH: 84
<212> TYPE: RNA
<213> ORGANISM: Homo sapiens

<400> SEQUENCE: 60
ggcuguggcu ggauucaagu aauccaggau aggcuguuuc caucugugag gccuauucuu       60
gauuacuugu uucuggaggc agcu                                             84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua       60
cuuggcucgg ggaccgg                                                     77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc agguccaca ccaagucgug uucacagugg        60
cuaaguuccg cccccccag                                                   78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauuggguuu ccgcuuuguu cacaguggcu      60
```

-continued aaguucugca ccu                                                    73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uccgcuuug    60 uucacagugg cuaaguucug caccugaaga gaaggug                           97

<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag caggguccac accaagucgu guucacagug   60
gcuaaguucc gccccccagg                                              80

<210> SEQ ID NO 66
<211> LENGTH: 86
<212> TYPE: RNA
<213> ORGANISM: Homo sapiens

<400> SEQUENCE: 66
gguccuugcc cucaaggagc ucacagucua uugaguuacc uuucugacuu ucccacuaga   60
uugugagcuc cuggagggca ggcacu                                       86

<210> SEQ ID NO 67
<211> LENGTH: 108
<212> TYPE: RNA
<213> ORGANISM: Homo sapiens

<400> SEQUENCE: 67
ccuucuguga ccccuuagag gaugacugau uucuuuuggu guucagaguc aauauaauuu   60
ucuagcacca ucugaaaucg guuauaauga uuggggaaga gcaccaug              108

<210> SEQ ID NO 68
<211> LENGTH: 64
<212> TYPE: RNA
<213> ORGANISM: Homo sapiens

<400> SEQUENCE: 68
augacugauu ucuuuuggug uucagaguca auauaauuuu cuagcaccau cugaaaucgg   60
uuau                                                               64

<210> SEQ ID NO 69
<211> LENGTH: 81
<212> TYPE: RNA
<213> ORGANISM: Homo sapiens

<400> SEQUENCE: 69
cuucaggaag cugguuucau auggugguuu agauuuaaau agugauuguc uagcaccauu   60
ugaaaucagu guucuugggg g                                            81

<210> SEQ ID NO 70
<211> LENGTH: 81
<212> TYPE: RNA
<213> ORGANISM: Homo sapiens

```
<400> SEQUENCE: 70
cuucuggaag cugguuucac augguggcuu agauuuuucc aucuuuguau cuagcaccau    60
uugaaaucag uguuuagga g                                                81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc ugguguucag agucuguuuu    60
ugucuagcac cauuugaaau cgguuaugau guaggggggaa aagcagcagc              110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug    60
uuugcagcug c                                                         71

<210> SEQ ID NO 73
<211> LENGTH: 60
<212> TYPE: RNA
<213> ORGANISM: Homo sapiens

<400> SEQUENCE: 73
auguaaacau ccuacacuca gcuguaauac auggauuggc ugggaggugg auguuuacgu    60

<210> SEQ ID NO 74
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga    60
gguggauguu uacuucagcu gacuugga                                       88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug    60
uuuacucuuu cu                                                        72

<210> SEQ ID NO 76
<211> LENGTH: 70
<212> TYPE: RNA
<213> ORGANISM: Homo sapiens

<400> SEQUENCE: 76
guuguuguaa acaucccgga cuggaagcug uaagacacag cuaagcuuuc agucagaugu    60
uugcugcuac                                                           70

<210> SEQ ID NO 77
<211> LENGTH: 64
```

<212> TYPE: RNA
<213> ORGANISM: Homo sapiens

<400> SEQUENCE: 77 cguaaacau ccuugacugg aagcuguaag guguucagag gagcuuucag ucggauguuu    60
acag                                                                64

<210> SEQ ID NO 78
<211> LENGTH: 71
<212> TYPE: RNA
<213> ORGANISM: Homo sapiens

<400> SEQUENCE: 78
ggagaggagg caagaugcug gcauagcugu ugaacuggga accugcuaug ccaacauauu    60
gccaucuuuc c                                                        71

<210> SEQ ID NO 79
<211> LENGTH: 70
<212> TYPE: RNA
<213> ORGANISM: Homo sapiens

<400> SEQUENCE: 79
ggagauauug cacauuacua aguugcaugu ugcacggcc ucaaugcaau uuagugugug     60
ugauauuuuc                                                          70

<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag    60
gcgggugcag ugccucggca gugcagcccg gagccggccc cuggcaccac              110

<210> SEQ ID NO 81
<211> LENGTH: 88
<212> TYPE: RNA
<213> ORGANISM: Homo sapiens

<400> SEQUENCE: 81
accaaguuuc aguucaugua aacauccuac acucagcugu aauacaugga uuggcuggga    60
ggugaguguu uacuucagcu gacuugga                                      88

<210> SEQ ID NO 82
<211> LENGTH: 69
<212> TYPE: RNA
<213> ORGANISM: Homo sapiens

<400> SEQUENCE: 82
cuguggugca uuguaguugc auugcauguu cugguggua ccaugcaaug uuccacagu      60 gcaucacag                                                           69

<210> SEQ ID NO 83
<211> LENGTH: 110
<212> TYPE: RNA
<213> ORGANISM: Homo sapiens

<400> SEQUENCE: 83
ggccagcugu gaguuuucu uuggcagugu cuuagcuggu uguugagc aauaguaagg       60 aagcaaucag caaguauacu gcccuagaag ugcugcacgu uguggggccc              110

-continued

```
<210> SEQ ID NO 84
<211> LENGTH: 84
<212> TYPE: RNA
<213> ORGANISM: Homo sapiens

<400> SEQUENCE: 84
gugcucgguu uguaggcagu gucauuagcu gauuguacug ugguugguuac aaucacuaac      60 uccacugcca ucaaaacaag gcac                                             84

<210> SEQ ID NO 85
<211> LENGTH: 77
<212> TYPE: RNA
<213> ORGANISM: Homo sapiens

<400> SEQUENCE: 85
agucuaguua cuaggcagug uaguuagcug auugcuaaua guaccaauca cuaaccacac      60
ggccagguaa aaagauu                                                     77

<210> SEQ ID NO 86
<211> LENGTH: 82
<212> TYPE: RNA
<213> ORGANISM: Homo sapiens

<400> SEQUENCE: 86
ucagaauaau gucaaagugc uuacagugca gguagugaua ugugcaucua cugcagugaa      60
ggcacuugua gcauuauggu ga                                               82

<210> SEQ ID NO 87
<211> LENGTH: 78
<212> TYPE: RNA
<213> ORGANISM: Homo sapiens

<400> SEQUENCE: 87
cuuucuacac agguugggau cgguugcaau gcuguguuuc uguaugguau ugcacuuguc      60
ccggccuguu gaguuugg                                                    78

<210> SEQ ID NO 88
<211> LENGTH: 75
<212> TYPE: RNA
<213> ORGANISM: Homo sapiens

<400> SEQUENCE: 88
ucaucccugg gugggggauuu guugcauuac uuguguucua uauaaaguau ugcacuuguc     60
ccggccugug gaaga                                                       75

<210> SEQ ID NO 89
<211> LENGTH: 80
<212> TYPE: RNA
<213> ORGANISM: Homo sapiens

<400> SEQUENCE: 89 cuggggggcuc caaagugcug uucgugcagg uagugugauu acccaaccua cugcugagcu     60
agcacuuccc gagccccgg                                                   80

<210> SEQ ID NO 90
<211> LENGTH: 81
<212> TYPE: RNA
<213> ORGANISM: Homo sapiens

<400> SEQUENCE: 90
```

```
aacacagugg gcacucaaua aaugucuguu gaauugaaau gcguuacauu caacggguau        60
uuauugagca cccacucugu g                                                 81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuuugc uugugucucu ccgcucugag caaucaugug        60
cagugccaau augggaaa                                                     78

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg        60
gauguuugca gcugccuacu                                                   80

<210> SEQ ID NO 93
<211> LENGTH: 80
<212> TYPE: RNA
<213> ORGANISM: Homo sapiens

<400> SEQUENCE: 93
gugagguagu aaguuguauu guugugggu agggauauua ggccccaauu agaagauaac         60
uauacaacuu acuacuuucc                                                   80

<210> SEQ ID NO 94
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgugucugug        60
gguccguguc                                                              70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu uguggugaag uggaccgcac aagcucgcuu        60
cuaugggucu gugucagugu g                                                 81

<210> SEQ ID NO 96
<211> LENGTH: 108
<212> TYPE: RNA
<213> ORGANISM: Homo sapiens

<400> SEQUENCE: 96
aagagagaag auauugaggc cguugccac aaacccguag auccgaacuu gugguauuag         60
uccgcacaag cuuguaucua uagguaugug ucguuaggc aaucucac                     108

<210> SEQ ID NO 97
<211> LENGTH: 80
```

```
<212> TYPE: RNA
<213> ORGANISM: Homo sapiens

<400> SEQUENCE: 97
ccuguugcca caaacccgua gauccgaacu uguggauuua guccgcacaa gcuuguaucu    60
auagguaugu gucuguuagg                                                80

<210> SEQ ID NO 98
<211> LENGTH: 110
<212> TYPE: RNA
<213> ORGANISM: Homo sapiens

<400> SEQUENCE: 98
aggcugcccu ggcucaguua ucacagugcu gaugcugucu auucuaaagg uacaguacug    60
ugauaacuga aggauggcag ccaucuuacc uuccaucaga ggagccucac               110

<210> SEQ ID NO 99
<211> LENGTH: 57
<212> TYPE: RNA
<213> ORGANISM: Homo sapiens

<400> SEQUENCE: 99
ucaguuauca cagugcugau gcuguccauu cuaaagguac aguacuguga uaacuga       57

<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugugau    60
aacugaagga uggca                                                     75

<210> SEQ ID NO 101
<211> LENGTH: 79
<212> TYPE: RNA
<213> ORGANISM: Homo sapiens

<400> SEQUENCE: 101
acuguccuuu uucgguuauc auggaccga ugcuguauau cugaaaggua caguacugug     60
auaacugaag aaugguggu                                                 79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau    60
aacugaagaa uggug                                                     75

<210> SEQ ID NO 103
<211> LENGTH: 81
<212> TYPE: RNA
<213> ORGANISM: Homo sapiens

<400> SEQUENCE: 103
cuucuggaag cugguucac augguggcuu agauuuuucc aucuuuguau cuagcaccau     60
uugaaaucag uguuuuagga g                                              81
```

```
<210> SEQ ID NO 104
<211> LENGTH: 81
<212> TYPE: RNA
<213> ORGANISM: Homo sapiens

<400> SEQUENCE: 104
cuucaggaag cugguuucau auggugguuu agauuuaaau agugauuguc uagcaccauu    60
ugaaaucagu guucuugggg g                                             81

<210> SEQ ID NO 105
<211> LENGTH: 78
<212> TYPE: RNA
<213> ORGANISM: Homo sapiens

<400> SEQUENCE: 105
uugugcuuuc agcuucuuua cagugcugcc uuguagcauu caggucaagc aacauuguac    60
agggcuauga aagaacca                                                 78

<210> SEQ ID NO 106
<211> LENGTH: 78
<212> TYPE: RNA
<213> ORGANISM: Homo sapiens

<400> SEQUENCE: 106
uacugcccuc ggcuucuuua cagugcugcc uuguugcaua uggaucaagc agcauuguac    60
agggcuauga aggcauug                                                 78

<210> SEQ ID NO 107
<211> LENGTH: 78
<212> TYPE: RNA
<213> ORGANISM: Homo sapiens

<400> SEQUENCE: 107
aaaugucaga cagcccaucg acugugugug ccaugagauu caacagucaa caucagucug    60
auaagcuacc cgacaagg                                                 78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu gugguggcug cucaugcacc acggauguuu    60
gagcaugugc uacggugucu a                                             81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu gugguggcug cuuaugcacc acggauguuu    60
gagcaugugc uauggugucu a                                             81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa    60
```

-continued

```
gcacuucuua cauuaccaug g                                           81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaugguucc ucuccgugcu accgcacugu   60
ggguacuugc ugcuccagca gg                                           82

<210> SEQ ID NO 112
<211> LENGTH: 81
<212> TYPE: RNA
<213> ORGANISM: Homo sapiens

<400> SEQUENCE: 112
cucucugcuu ucagcuucuu uacagaguug ccuuguggca uggaguucaa gcagcauugu   60
acagggcuau caaagcacag a                                            81

<210> SEQ ID NO 113
<211> LENGTH: 90
<212> TYPE: RNA
<213> ORGANISM: Homo sapiens

<400> SEQUENCE: 113
acacugcaag aacaauaagg auuuuuaggg gcauuaugac ugagucagaa aacacagcug   60
ccccugaaag ucccucauuu uucuugcugu                                   90

<210> SEQ ID NO 114
<211> LENGTH: 80
<212> TYPE: RNA
<213> ORGANISM: Homo sapiens

<400> SEQUENCE: 114
acugcaagag caauaaggau uuuuaggggc auuaugauag uggaauggaa acacaucugc   60
ccccaaaagu cccucauuuu                                              80

<210> SEQ ID NO 115
<211> LENGTH: 85
<212> TYPE: RNA
<213> ORGANISM: Homo sapiens

<400> SEQUENCE: 115
ccuuagcaga gcuguggagu gugacaaugg uguuugaguc uaaacuauca aacgccauua   60
ucacacuaaa uagcuacugc uaggc                                        85

<210> SEQ ID NO 116
<211> LENGTH: 66
<212> TYPE: RNA
<213> ORGANISM: Homo sapiens

<400> SEQUENCE: 116
agcuguggag ugugacaaug guguuugugu ccaaacuauc aaacgccauu aucacacuaa   60
auagcu                                                             66

<210> SEQ ID NO 117
<211> LENGTH: 61
<212> TYPE: RNA
<213> ORGANISM: Homo sapiens
```

<400> SEQUENCE: 117
acauuauuac uuuugguacg cgcugugaca cuucaaacuc guaccgugag uaauaaugcg    60
c                                                                   61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac    60
gcggugaaug ccaagaaugg ggcug                                         85

<210> SEQ ID NO 119
<211> LENGTH: 110
<212> TYPE: RNA
<213> ORGANISM: Homo sapiens

<400> SEQUENCE: 119
aucaagauua gaggcucugc ucuccguguu cacagcggac cuugauuuaa ugucauacaa    60
uuaaggcacg cggugaaugc caagagcgga gccuacggcu gcacuugaag              110

<210> SEQ ID NO 120
<211> LENGTH: 87
<212> TYPE: RNA
<213> ORGANISM: Homo sapiens

<400> SEQUENCE: 120
ugagggcccc ucugcguguu cacagcggac cuugauuuaa ugucuauaca auuaaggcac    60
gcggugaaug ccaagagagg cgccucc                                       87

<210> SEQ ID NO 121
<211> LENGTH: 68
<212> TYPE: RNA
<213> ORGANISM: Homo sapiens

<400> SEQUENCE: 121
cucugcgugu ucacagcgga ccuugauuua augucuauac aauuaaggca cgcggugaau    60
gccaagag                                                            68

<210> SEQ ID NO 122
<211> LENGTH: 67
<212> TYPE: RNA
<213> ORGANISM: Homo sapiens

<400> SEQUENCE: 122
cucuccgugu ucacagcgga ccuugauuua augucauaca auuaaggcac gcggugaaug    60
ccaagag                                                             67

<210> SEQ ID NO 123
<211> LENGTH: 86
<212> TYPE: RNA
<213> ORGANISM: Homo sapiens

<400> SEQUENCE: 123
ugccagucuc uaggucccug agaccuuuua accugugagg acauccaggg ucacagguga    60
gguucuuggg agccuggcgu cuggcc                                        86

```
<210> SEQ ID NO 124
<211> LENGTH: 65
<212> TYPE: RNA
<213> ORGANISM: Homo sapiens

<400> SEQUENCE: 124
ggucccugag acccuuuaac cugugaggac auccaggguc acaggugagg uucuugggag        60
ccugg                                                                    65

<210> SEQ ID NO 125
<211> LENGTH: 88
<212> TYPE: RNA
<213> ORGANISM: Homo sapiens

<400> SEQUENCE: 125
ugcgcuccuc ucagucccug agacccuaac uugugauguu uaccguuuaa auccacgggu        60
uaggcucuug ggagcugcga gucgugcu                                           88

<210> SEQ ID NO 126
<211> LENGTH: 89
<212> TYPE: RNA
<213> ORGANISM: Homo sapiens

<400> SEQUENCE: 126
accagacuuu uccuaguccc ugagacccua acuugugagg uauuuuagua acaucacaag        60
ucaggcucuu gggaccuagg cggagggga                                          89

<210> SEQ ID NO 127
<211> LENGTH: 85
<212> TYPE: RNA
<213> ORGANISM: Homo sapiens

<400> SEQUENCE: 127
cgcuggcgac gggacauuau uacuuuuggu acgcgcugug acacuucaaa cucguaccgu        60
gaguaauaau gcgccgucca cggca                                              85

<210> SEQ ID NO 128
<211> LENGTH: 61
<212> TYPE: RNA
<213> ORGANISM: Homo sapiens

<400> SEQUENCE: 128
acauuauuac uuuugguacg cgcugugaca cuucaaacuc guaccgugag uaauaaugcg        60
c                                                                        61

<210> SEQ ID NO 129
<211> LENGTH: 97
<212> TYPE: RNA
<213> ORGANISM: Homo sapiens

<400> SEQUENCE: 129
ugugaucacu gucuccagcc ugcugaagcu cagagggcuc ugauucagaa agaucaucgg        60
auccgucuga gcuuggcugg ucggaagucu caucauc                                 97

<210> SEQ ID NO 130
<211> LENGTH: 70
<212> TYPE: RNA
<213> ORGANISM: Homo sapiens

<400> SEQUENCE: 130
ccagccugcu gaagcucaga gggcucugau ucagaaagau caucggaucc gucugagcuu        60
```
ggcuggucgg                                                              70

<210> SEQ ID NO 131
<211> LENGTH: 82
<212> TYPE: RNA
<213> ORGANISM: Homo sapiens

<400> SEQUENCE: 131
ugagcuguug gauucggggc cguagcacug ucugagaggu uuacauuucu cacagugaac        60
cggucucuuu uucagcugcu uc                                                82

<210> SEQ ID NO 132
<211> LENGTH: 110
<212> TYPE: RNA
<213> ORGANISM: Homo sapiens

<400> SEQUENCE: 132
gcccggcagc cacugugcag ugggaagggg ggccgauaca cuguacgaga gugaguagca        60
ggucucacag ugaaccgguc ucuucccua cugugucaca cuccuaaugg                   110

<210> SEQ ID NO 133
<211> LENGTH: 70
<212> TYPE: RNA
<213> ORGANISM: Homo sapiens

<400> SEQUENCE: 133
guuggauucg gggccguagc acugucugag agguuuacau uucucacagu gaaccggucu        60
cuuuuucagc                                                              70

<210> SEQ ID NO 134
<211> LENGTH: 74
<212> TYPE: RNA
<213> ORGANISM: Homo sapiens

<400> SEQUENCE: 134
uggaucuuuu ugcggucugg gcuugcuguu ccucucaaca guagucagga agcccuuacc        60
ccaaaaagua ucua                                                         74

<210> SEQ ID NO 135
<211> LENGTH: 90
<212> TYPE: RNA
<213> ORGANISM: Homo sapiens

<400> SEQUENCE: 135
ugcccuucgc gaaucuuuuu gcggucuggg cuugcuguac auaacucaau agccggaagc        60
ccuuacccca aaaagcauuu gcggagggcg                                        90

<210> SEQ ID NO 136
<211> LENGTH: 89
<212> TYPE: RNA
<213> ORGANISM: Homo sapiens

<400> SEQUENCE: 136
ugcugcuggc cagagcucuu uucacauugu gcuacugucu gcaccuguca cuagcagugc        60
aauguuaaaa gggcauuggc cguguagug                                         89

<210> SEQ ID NO 137
<211> LENGTH: 110
<212> TYPE: RNA
<213> ORGANISM: Homo sapiens

```
<400> SEQUENCE: 137
gccaggaggc ggggtugguu guuaucuuug guuaucuagc uguaugagug guguggaguc      60
uucauaaagc uagauaaccg aaaguaaaaa uaaccccaua cacugcgcag                110

<210> SEQ ID NO 138
<211> LENGTH: 110
<212> TYPE: RNA
<213> ORGANISM: Homo sapiens

<400> SEQUENCE: 138
cacggcgcgg cagcggcacu ggcuaaggga ggcccguuuc ucucuuuggu uaucuagcug      60
uaugagugcc acagagccgu cauaaagcua gauaaccgaa aguagaaaug                110

<210> SEQ ID NO 139
<211> LENGTH: 72
<212> TYPE: RNA
<213> ORGANISM: Homo sapiens

<400> SEQUENCE: 139
guuguuaucu uugguuaucu agcuguauga guguauuggu cuucauaaag cuagauaacc      60
gaaaguaaaa ac                                                         72

<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu uacgugggga acuggaggua      60
acagucuaca gccauggucg ccccgcagca cgcccacgcg c                         101

<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug ggaacuggag guaacagucu acagccaugg      60
ucgccc                                                                66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc      60
ccuucaacca gcuguagcua ugcauuga                                        88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu      60 uggucccuu caaccagcug uagcugugca uugauggcgc cg                         102
```

```
<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca     60
gcuguagc                                                             68

<210> SEQ ID NO 145
<211> LENGTH: 119
<212> TYPE: RNA
<213> ORGANISM: Homo sapiens

<400> SEQUENCE: 145
ccucagaaga aagaugcccc cugcucuggc uggucaaacg gaaccaaguc cgucuuccug     60
agagguuugg uccccuucaa ccagcuacag cagggcuggc aaugcccagu ccuuggaga    119

<210> SEQ ID NO 146
<211> LENGTH: 80
<212> TYPE: RNA
<213> ORGANISM: Homo sapiens

<400> SEQUENCE: 146
gcccccugcu cuggcugguc aaacggaacc aaguccgucu ccugagagg uuuggucccc     60 uucaaccagc uacagcaggg                                                80

<210> SEQ ID NO 147
<211> LENGTH: 73
<212> TYPE: RNA
<213> ORGANISM: Homo sapiens

<400> SEQUENCE: 147
cagggugugu gacugguuga ccagaggggc augcacugug uucacccugu gggccaccua     60
gucaccaacc cuc                                                       73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu cacccugug gccaccuag       60 ucaccaaccc u                                                         71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuuauu ccuaugugau ucuacugcuc acucauauag     60
ggauuggagc cguggcgcac ggcggggaca                                     90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagucuc     60
```
auguagggau ggaagccaug aaauacauug ugaaaaauca                                  100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca uauagggauu ggagccgugg            60

<210> SEQ ID NO 152
<211> LENGTH: 97
<212> TYPE: RNA
<213> ORGANISM: Homo sapiens

<400> SEQUENCE: 152
cacucugcug uggccuaugg cuuuucauuc cuaugugauu gcugcccaa acucauguag             60 ggcuaaaagc caugggcuac agugaggggc gagcucc                                    97

<210> SEQ ID NO 153
<211> LENGTH: 82
<212> TYPE: RNA
<213> ORGANISM: Homo sapiens

<400> SEQUENCE: 153
ugagcccucg gaggacucca uuuguuuuga ugauggauuc uuaugcucca ucaucgucuc            60
aaaugagucu ucagagggu cu                                                     82

<210> SEQ ID NO 154
<211> LENGTH: 62
<212> TYPE: RNA
<213> ORGANISM: Homo sapiens

<400> SEQUENCE: 154
gaggacucca uuuguuuuga ugauggauuc uuaugcucca ucaucgucuc aaaugagucu            60
uc                                                                          62

<210> SEQ ID NO 155
<211> LENGTH: 73
<212> TYPE: RNA
<213> ORGANISM: Homo sapiens

<400> SEQUENCE: 155
cuucggugac ggguauucuu ggguggauaa uacggauuac guuguuauug cuuaagaaua            60
cgcguagucg agg                                                              73

<210> SEQ ID NO 156
<211> LENGTH: 99
<212> TYPE: RNA
<213> ORGANISM: Homo sapiens

<400> SEQUENCE: 156
cccuggcaug gugugguggg gcagcuggug uugugaauca ggccguugcc aaucagagaa           60
cggcuacuuc acaacaccag ggccacacca cacuacagg                                  99

<210> SEQ ID NO 157
<211> LENGTH: 84
<212> TYPE: RNA
<213> ORGANISM: Homo sapiens

<400> SEQUENCE: 157

```
cguugcugca gcuggugunug ugaaucaggc cgacgagcag cgcauccucu uacccggcua    60
uuucacgaca ccaggguugc auca                                           84

<210> SEQ ID NO 158
<211> LENGTH: 71
<212> TYPE: RNA
<213> ORGANISM: Homo sapiens

<400> SEQUENCE: 158
cagcuggugu ugugaaucag gccgacgagc agcgcauccu cuuacccggc uauuucacga    60
caccaggguu g                                                         71

<210> SEQ ID NO 159
<211> LENGTH: 68
<212> TYPE: RNA
<213> ORGANISM: Homo sapiens

<400> SEQUENCE: 159
guguauucua cagugcacgu gucuccagug uggcucggag gcuggagacg cggcccuguu    60
ggaguaac                                                             68

<210> SEQ ID NO 160
<211> LENGTH: 100
<212> TYPE: RNA
<213> ORGANISM: Homo sapiens

<400> SEQUENCE: 160 ugugcucuc ucuguguccu gccaguggun uuacccuaug guagguuacg ucaugcuguu     60
cuaccacagg guagaaccac ggacaggaua ccggggcacc                         100

<210> SEQ ID NO 161
<211> LENGTH: 72
<212> TYPE: RNA
<213> ORGANISM: Homo sapiens

<400> SEQUENCE: 161
uccugccagu gguuuuaccc uaugguaggu uacgucaugc uguucuacca cagguagaa    60 ccacggacag ga                                                        72

<210> SEQ ID NO 162
<211> LENGTH: 70
<212> TYPE: RNA
<213> ORGANISM: Homo sapiens

<400> SEQUENCE: 162
ccugccagug guuuuacccu auggaugguu acgucaugcu guucuaccac agguagaac    60 cacggacagg                                                           70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcccua    60 acacugucug guaaagaugg cucccggguig gguuc                              95

<210> SEQ ID NO 164
<211> LENGTH: 72
```

<212> TYPE: RNA
<213> ORGANISM: Homo sapiens

<400> SEQUENCE: 164 gguccaucu uccaguacag uguuggaugg ucuaauugug aagcuccuaa cacugucugg    60
uaaagauggc cc                                                      72

<210> SEQ ID NO 165
<211> LENGTH: 64
<212> TYPE: RNA
<213> ORGANISM: Homo sapiens

<400> SEQUENCE: 165
acccauaaag uagaaagcac uacuaacagc acuggagggu guaguguuuc cuacuuuaug    60
gaug                                                                64

<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucggucca guuggagguc    60
ugagaugaag cacuguagcu caggaagaga gaaguuguuc ugcagc                 106

<210> SEQ ID NO 167
<211> LENGTH: 63
<212> TYPE: RNA
<213> ORGANISM: Homo sapiens

<400> SEQUENCE: 167 ccugagguge agugcugcau cucuggucag uugggagucu gagaugaagc acuguagcuc    60
agg                                                                 63

<210> SEQ ID NO 168
<211> LENGTH: 86
<212> TYPE: RNA
<213> ORGANISM: Homo sapiens

<400> SEQUENCE: 168
uggggcccug gcugggauau caucauauac uguaaguuug cgaugagaca cuacaguaua    60
gaugauguac uagccgggc acccc                                          86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua    60
cuaguc                                                              66

<210> SEQ ID NO 170
<211> LENGTH: 88
<212> TYPE: RNA
<213> ORGANISM: Homo sapiens

<400> SEQUENCE: 170
caccuugucc ucacggucca guuucccag gaaucccuua gaugcuaaga uggggauucc    60
uggaaauacu guucuugagg ucaugguu                                      88

<210> SEQ ID NO 171
<211> LENGTH: 70
<212> TYPE: RNA
<213> ORGANISM: Homo sapiens

<400> SEQUENCE: 171
cucacggucc aguuucccca ggaaucccuu agaugcuaag auggggauuc cuggaaauac  60
uguucuugag                                                          70

<210> SEQ ID NO 172
<211> LENGTH: 99
<212> TYPE: RNA
<213> ORGANISM: Homo sapiens

<400> SEQUENCE: 172
ccgaugugua uccucagcuu ugagaacuga auuccauggg uugugucagu gucagaccuc  60
ugaaauucag uucuucagcu gggauaucuc ugucaucgu                          99

<210> SEQ ID NO 173
<211> LENGTH: 65
<212> TYPE: RNA
<213> ORGANISM: Homo sapiens

<400> SEQUENCE: 173
agcuuugaga acugaauucc auggguugug ucagugucag accugugaaa uucaguucuu  60
cagcu                                                               65

<210> SEQ ID NO 174
<211> LENGTH: 72
<212> TYPE: RNA
<213> ORGANISM: Homo sapiens

<400> SEQUENCE: 174
aaucuaaaga caacauuucu gcacacacac cagacuaugg aagccagugu guggaaaugc  60
uucugcuaga uu                                                       72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac  60
uuugucuc                                                            68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa  60
agucagugca ucacagaacu uugucucgaa agcuuucua                          99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau                                                          70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacucccgug cuugccgag gagggaggga    60 gggacggggg cugugcuggg gcagcugga                                     89

<210> SEQ ID NO 179
<211> LENGTH: 53
<212> TYPE: RNA
<213> ORGANISM: Homo sapiens

<400> SEQUENCE: 179
gcucuggcuc cgugucuuca cucccgugcu uguccgagga gggagggagg gac          53

<210> SEQ ID NO 180
<211> LENGTH: 84
<212> TYPE: RNA
<213> ORGANISM: Homo sapiens

<400> SEQUENCE: 180
cuccccaugg cccugucucc caacccuugu accagugcug ggcucagacc cugguacagg    60 ccuggggac agggaccugg ggac                                           84

<210> SEQ ID NO 181
<211> LENGTH: 64
<212> TYPE: RNA
<213> ORGANISM: Homo sapiens

<400> SEQUENCE: 181
cccugucucc caacccuugu accagugcug ggcucagacc cugguacagg ccuggggac    60 aggg                                                               64

<210> SEQ ID NO 182
<211> LENGTH: 72
<212> TYPE: RNA
<213> ORGANISM: Homo sapiens

<400> SEQUENCE: 182
uuuccugccc ucgaggagcu cacagucuag uaugucucau ccccuacuag acugaagcuc    60
cuugaggaca gg                                                       72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc    60
gagggcagg                                                          69

<210> SEQ ID NO 184
<211> LENGTH: 87
<212> TYPE: RNA
<213> ORGANISM: Homo sapiens

```
<400> SEQUENCE: 184 ugucccccc ggcccagguu cugugauaca cuccgacucg ggcucuggag cagucagugc      60
augacagaac uugggcccgg aaggacc                                        87

<210> SEQ ID NO 185
<211> LENGTH: 71
<212> TYPE: RNA
<213> ORGANISM: Homo sapiens

<400> SEQUENCE: 185
ggcccagguu cugugauaca cuccgacucg ggcucuggag cagucagugc augacagaac    60
uugggccccg g                                                         71

<210> SEQ ID NO 186
<211> LENGTH: 90
<212> TYPE: RNA
<213> ORGANISM: Homo sapiens

<400> SEQUENCE: 186
cucacagcug ccagugucau uuugugauc ugcagcuagu auucucacuc caguugcaua     60
gucacaaaag ugaucauugg caggguggc                                      90

<210> SEQ ID NO 187
<211> LENGTH: 71
<212> TYPE: RNA
<213> ORGANISM: Homo sapiens

<400> SEQUENCE: 187
ucucucucuc ccucacagcu gccaguguca uugucacaaa agugaucauu ggcaggugug    60
gcugcugcau g                                                         71

<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc aguugcauag    60
ucacaaaagu gaucauugga aacugug                                        87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag    60
ugaucauug                                                            69

<210> SEQ ID NO 190
<211> LENGTH: 84
<212> TYPE: RNA
<213> ORGANISM: Homo sapiens

<400> SEQUENCE: 190
gugguacuug aagauagguu auccguguug ccuucgcuuu auuugugacg aaucauacac    60
gguugaccua uuuucagua ccaa                                            84
```

```
<210> SEQ ID NO 191
<211> LENGTH: 66
<212> TYPE: RNA
<213> ORGANISM: Homo sapiens

<400> SEQUENCE: 191
gaagauaggu uauccguguu gccuucgcuu uauuugugac gaaucauaca cgguugaccu     60
auuuuu                                                                66

<210> SEQ ID NO 192
<211> LENGTH: 65
<212> TYPE: RNA
<213> ORGANISM: Homo sapiens

<400> SEQUENCE: 192
cuguuaaugc uaaucgugau aggguuuuu gccuccaacu gacuccuaca uauuagcauu      60
aacag                                                                 65

<210> SEQ ID NO 193
<211> LENGTH: 82
<212> TYPE: RNA
<213> ORGANISM: Homo sapiens

<400> SEQUENCE: 193
ccuaacacug ucgguaaag auggcucccg gguggguucu cucggcagua accuucaggg     60
agcccugaag accauggagg ac                                              82

<210> SEQ ID NO 194
<211> LENGTH: 110
<212> TYPE: RNA
<213> ORGANISM: Homo sapiens

<400> SEQUENCE: 194
gccgagaccg agugcacagg gcucugaccu augaauugac agccagugcu cucgucuccc    60
cucuggcugc caauuccaua ggucacaggu auguucgccu caaugccagc               110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cugguuccag uggggcugcu    60
guuaucuggg gcgagggcca                                                 80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucuggcuac gcuaugcugc     60 ggcgcucggg                                                            70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgaguccca ccgggguaa agaaaggccg     60
```

```
aauu                                                                    64

<210> SEQ ID NO 198
<211> LENGTH: 70
<212> TYPE: RNA
<213> ORGANISM: Homo sapiens

<400> SEQUENCE: 198
ccuaagccag ggauuguggg uucgagcccc accuggggua gaggugaaag uuccuuuuac       60
ggaauuuuuu                                                              70

<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc       60
caguauuaac ugugcugcug aaguaagguu gaccauacuc uacaguug                   108

<210> SEQ ID NO 200
<211> LENGTH: 81
<212> TYPE: RNA
<213> ORGANISM: Homo sapiens

<400> SEQUENCE: 200
gggcuuucaa gucacuagug guuccguuua guagaugauu ugcauuguu ucaaaauggu        60 gcccuaguga cuacaaagcc c                                                 81

<210> SEQ ID NO 201
<211> LENGTH: 70
<212> TYPE: RNA
<213> ORGANISM: Homo sapiens

<400> SEQUENCE: 201
acgcaagugu ccuaaggugu gcucaggag cacagaaacc uccaguggaa cagaagggca        60
aaagcucauu                                                              70

<210> SEQ ID NO 202
<211> LENGTH: 70
<212> TYPE: RNA
<213> ORGANISM: Homo sapiens

<400> SEQUENCE: 202 caugucac uuucaggugg aguuucaaga gucccuuccu gguucaccgu cuccuuugcu         60
cuuccacaac                                                              70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag       60
uuugggauuu gaaaaaacca cugaccguug acuguaccuu ggggguccuua                110

<210> SEQ ID NO 204
<211> LENGTH: 110
<212> TYPE: RNA
<213> ORGANISM: Homo sapiens
```

<400> SEQUENCE: 204
ccugugcaga gauuauuuuu uaaaaggucu caaucaacau ucauugcugu cgguggguug    60
aacugugugg acaagcucac ugaacaauga augcaacugu ggccccgcuu             110

<210> SEQ ID NO 205
<211> LENGTH: 89
<212> TYPE: RNA
<213> ORGANISM: Homo sapiens

<400> SEQUENCE: 205
cugauggcug cacucaacau ucauugcugu cgguggguuu gagucugaau caacucacug    60
aucaaugaau gcaaacugcg gaccaaaca                                    89

<210> SEQ ID NO 206
<211> LENGTH: 110
<212> TYPE: RNA
<213> ORGANISM: Homo sapiens

<400> SEQUENCE: 206
cggaaaauuu gccaaggguu uggggggaaca uucaaccugu cggugaguuu ggcagcuca    60 ggcaaaccau cgaccguuga guggacccug aggccuggaa uugccauccu              110

<210> SEQ ID NO 207
<211> LENGTH: 110
<212> TYPE: RNA
<213> ORGANISM: Homo sapiens

<400> SEQUENCE: 207
gagcugcuug ccuccccccg uuuuuggcaa ugguagaacu cacacuggug agguaacagg    60
auccgguggu ucuagacuug ccaacuaugg ggcgaggacu cagccggcac              110

<210> SEQ ID NO 208
<211> LENGTH: 70
<212> TYPE: RNA
<213> ORGANISM: Homo sapiens

<400> SEQUENCE: 208
uuuuuggcaa ugguagaacu cacacuggug agguaacagg auccgguggu ucuagacuug    60
ccaacuaugg                                                          70

<210> SEQ ID NO 209
<211> LENGTH: 110
<212> TYPE: RNA
<213> ORGANISM: Homo sapiens

<400> SEQUENCE: 209
ccgcagagug ugacuccugu ucuguguaug gcacugguag aauucacugu gaacagucuc    60
agucagugaa uuaccgaagg gccauaaaca gagcagagac agauccacga              110

<210> SEQ ID NO 210
<211> LENGTH: 84
<212> TYPE: RNA
<213> ORGANISM: Homo sapiens

<400> SEQUENCE: 210
ccagucacgu ccccuuauca cuuuccagc ccagcuuugu gacuguaagu guuggacgga    60
gaacugauaa ggguagguga uuga                                          84

```
<210> SEQ ID NO 211
<211> LENGTH: 65
<212> TYPE: RNA
<213> ORGANISM: Homo sapiens

<400> SEQUENCE: 211
ccuuaucacu uuccagccc agcuuuguga cuguaagugu uggacggaga acugauaagg    60
guagg                                                              65

<210> SEQ ID NO 212
<211> LENGTH: 82
<212> TYPE: RNA
<213> ORGANISM: Homo sapiens

<400> SEQUENCE: 212
agggggcgag ggauuggaga gaaaggcagu uccugauggu ccccuccca ggggcuggcu   60 uuccucuggu ccuucccucc ca                                           82

<210> SEQ ID NO 213
<211> LENGTH: 66
<212> TYPE: RNA
<213> ORGANISM: Homo sapiens

<400> SEQUENCE: 213
agggauugga gagaaaggca guuccugaug gucccuccc caggggcugg cuuuccucug   60
guccuu                                                             66

<210> SEQ ID NO 214
<211> LENGTH: 86
<212> TYPE: RNA
<213> ORGANISM: Homo sapiens

<400> SEQUENCE: 214
ugcuuguaac uuuccaaaga auucuccuuu ugggcuuucu gguuuuauuu uaagcccaaa   60
ggugaauuuu uugggaaguu ugagcu                                       86

<210> SEQ ID NO 215
<211> LENGTH: 71
<212> TYPE: RNA
<213> ORGANISM: Homo sapiens

<400> SEQUENCE: 215
acuuuccaaa gaauucuccu uuugggcuuu cugguuuuau uuuaagccca aaggugaauu   60
uuuugggaag u                                                       71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug   60
cucugacccc ucgugucuug uguugcagcc ggagggacgc agguccgca              109

<210> SEQ ID NO 217
<211> LENGTH: 86
<212> TYPE: RNA
<213> ORGANISM: Homo sapiens

<400> SEQUENCE: 217 ugcuccccucu cucacaucccc uugcaugguug gaggugagc uuucugaaaa ccccucccac   60
```

```
augcaggguu ugcaggaugg cgagcc                                        86

<210> SEQ ID NO 218
<211> LENGTH: 68
<212> TYPE: RNA
<213> ORGANISM: Homo sapiens

<400> SEQUENCE: 218
ucucacaucc cuugcauggu ggagggugag cuuucugaaa accccuccca caugcagggu   60
uugcagga                                                           68

<210> SEQ ID NO 219
<211> LENGTH: 102
<212> TYPE: RNA
<213> ORGANISM: Homo sapiens

<400> SEQUENCE: 219 cgucgauug acccgcccu ccggugccua cugagcugau aucaguucuc auuuacaca     60 cuggcucagu ucagcaggaa caggagucga gcccuugagc aa                    102

<210> SEQ ID NO 220
<211> LENGTH: 68
<212> TYPE: RNA
<213> ORGANISM: Homo sapiens

<400> SEQUENCE: 220
cuccggugcc uacugagcug auaucaguuc ucauuuuaca cacuggcuca guucagcagg   60
aacaggag                                                           68

<210> SEQ ID NO 221
<211> LENGTH: 85
<212> TYPE: RNA
<213> ORGANISM: Homo sapiens

<400> SEQUENCE: 221
ugcaggccuc ugugugauau guuugauaua uuagguuguu auuuaaucca acuauauauc   60
aaacauauuc cuacaguguc uugcc                                        85

<210> SEQ ID NO 222
<211> LENGTH: 67
<212> TYPE: RNA
<213> ORGANISM: Homo sapiens

<400> SEQUENCE: 222
cugugugaua uguuugauau auuagguugu auuuaaucc aacuauauau caaacauauu   60
ccuacag                                                            67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucuccagag cauuccagcu   60
gcgcuuggau uucgucccu gcucuccugc cu                                 92

<210> SEQ ID NO 224
<211> LENGTH: 74
<212> TYPE: RNA
<213> ORGANISM: Homo sapiens
```

<400> SEQUENCE: 224
agcgggcaac ggaaucccaa aagcagcugu ugucuccaga gcauccagc ugcgcuugga    60 uuucguccccc ugcu    74

<210> SEQ ID NO 225
<211> LENGTH: 108
<212> TYPE: RNA
<213> ORGANISM: Homo sapiens

<400> SEQUENCE: 225
ccgagaccga gugcacaggg cucugaccua ugaauugaca gccagugcuc ucgucuccc    60 ucuggcugcc aauuccauag gucacaggua guucgccuc aaugccag    108

<210> SEQ ID NO 226
<211> LENGTH: 110
<212> TYPE: RNA
<213> ORGANISM: Homo sapiens

<400> SEQUENCE: 226
gccgagaccg agugcacagg gcucugaccu augaauugac agccagugcu cucgucuccc    60
cucuggcugc caauuccaua ggucacaggu auguucgccu caaugccagc    110

<210> SEQ ID NO 227
<211> LENGTH: 88
<212> TYPE: RNA
<213> ORGANISM: Homo sapiens

<400> SEQUENCE: 227
cgaggauggg agcugagggc ugggucuuug cgggcgagau gaggguguucg gaucaacugg    60 ccuacaaagu cccaguucuc ggcccccg    88

<210> SEQ ID NO 228
<211> LENGTH: 58
<212> TYPE: RNA
<213> ORGANISM: Homo sapiens

<400> SEQUENCE: 228
gcugggucuu ugcgggcgag augaggguguu cggaucaacu ggccuacaaa gucccagu    58

<210> SEQ ID NO 229
<211> LENGTH: 85
<212> TYPE: RNA
<213> ORGANISM: Homo sapiens

<400> SEQUENCE: 229
augguguuau caaguguaac agcaaccucca ugggacugu guaccaauuu ccaguggaga    60
ugcuguuacu uuugauggu accaa    85

<210> SEQ ID NO 230
<211> LENGTH: 63
<212> TYPE: RNA
<213> ORGANISM: Homo sapiens

<400> SEQUENCE: 230
guguaacagc aacuccaugu ggacugugua ccaauuucca guggagaugc uguuacuuuu    60
gau    63

<210> SEQ ID NO 231
<211> LENGTH: 87

```
<212> TYPE: RNA
<213> ORGANISM: Homo sapiens

<400> SEQUENCE: 231
agcuucccug gcucuagcag cacagaaaua uuggcacagg gaagcgaguc ugccaauauu    60
ggcugugcug cuccaggcag gguggug                                         87

<210> SEQ ID NO 232
<211> LENGTH: 58
<212> TYPE: RNA
<213> ORGANISM: Homo sapiens

<400> SEQUENCE: 232
uagcagcaca gaaauauugg cacagggaag cgagucugcc aauauuggcu gugcugcu      58

<210> SEQ ID NO 233
<211> LENGTH: 110
<212> TYPE: RNA
<213> ORGANISM: Homo sapiens

<400> SEQUENCE: 233
cuagagcuug aauuggaacu gcugagugaa uuagguaguu caguuguu gggccugggu      60 uucugaacac aacaacauua aaccacccga uucacggcag uuacugcucc              110

<210> SEQ ID NO 234
<211> LENGTH: 70
<212> TYPE: RNA
<213> ORGANISM: Homo sapiens

<400> SEQUENCE: 234
gugaauuagg uaguucaug uuguugggcc uggguuucug aacacaacaa cauuaaacca     60
cccgauucac                                                            70

<210> SEQ ID NO 235
<211> LENGTH: 110
<212> TYPE: RNA
<213> ORGANISM: Homo sapiens

<400> SEQUENCE: 235
ugcucgcuca gcugaucugu ggcuuaggua guuucauguu guugggauug aguuugaac     60 ucggcaacaa gaaacugccu gaguuacauc agucgguuuu cgucgagggc              110

<210> SEQ ID NO 236
<211> LENGTH: 70
<212> TYPE: RNA
<213> ORGANISM: Homo sapiens

<400> SEQUENCE: 236
gugaauuagg uaguucaug uuguugggcc uggguuucug aacacaacaa cauuaaacca     60
cccgauucac                                                            70

<210> SEQ ID NO 237
<211> LENGTH: 84
<212> TYPE: RNA
<213> ORGANISM: Homo sapiens

<400> SEQUENCE: 237
acuggucggu gauuagggua guuccuguu guugggaucc accuuucucu cgacagcacg     60
acacugccuu cauuacuuca guug                                            84
```

```
<210> SEQ ID NO 238
<211> LENGTH: 75
<212> TYPE: RNA
<213> ORGANISM: Homo sapiens

<400> SEQUENCE: 238
ggcugugccg gguagagagg gcagugggag guaagagcuc uucacccuuc accaccuucu      60
ccacccagca uggcc                                                      75

<210> SEQ ID NO 239
<211> LENGTH: 60
<212> TYPE: RNA
<213> ORGANISM: Homo sapiens

<400> SEQUENCE: 239
gugcaugugu auguaugugu gcaugugcau guguaugugu augagugcau gcgugugugc      60

<210> SEQ ID NO 240
<211> LENGTH: 62
<212> TYPE: RNA
<213> ORGANISM: Homo sapiens

<400> SEQUENCE: 240
ucauuggucc agaggggaga uagguuccug ugauuuuucc uucuucucua uagaauaaau      60
ga                                                                    62

<210> SEQ ID NO 241
<211> LENGTH: 71
<212> TYPE: RNA
<213> ORGANISM: Homo sapiens

<400> SEQUENCE: 241
gccaacccag uguucagacu accuguucag gaggcucuca auguguacag uagucugcac      60
auugguuagg c                                                          71

<210> SEQ ID NO 242
<211> LENGTH: 110
<212> TYPE: RNA
<213> ORGANISM: Homo sapiens

<400> SEQUENCE: 242
aggaagcuuc uggagauccu gcuccgucgc cccaguguuc agacuaccug uucaggacaa      60
ugccguugua caguagucug cacauugguu agacugggca agggagagca                110

<210> SEQ ID NO 243
<211> LENGTH: 110
<212> TYPE: RNA
<213> ORGANISM: Homo sapiens

<400> SEQUENCE: 243
ccagaggaca ccuccacucc gucuacccag uguuagacu aucuguucag gacucccaaa       60
uuguacagua gucugcacau ugguuaggcu gggcuggguu agacccucgg                110

<210> SEQ ID NO 244
<211> LENGTH: 71
<212> TYPE: RNA
<213> ORGANISM: Homo sapiens

<400> SEQUENCE: 244
gccaacccag uguucagacu accuguucag gaggcucuca auguguacag uagucugcac      60
auugguuagg c                                                          71
```

<210> SEQ ID NO 245
<211> LENGTH: 70
<212> TYPE: RNA
<213> ORGANISM: Homo sapiens

<400> SEQUENCE: 245
gccguggcca ucuuacuggg cagcauugga uggagucagg ucucuaauac ugccugguaa    60
ugaugacggc                                                           70

<210> SEQ ID NO 246
<211> LENGTH: 95
<212> TYPE: RNA
<213> ORGANISM: Homo sapiens

<400> SEQUENCE: 246
ccagcucggg cagccguggc caucuuacug ggcagcauug gauggaguca ggucucuaau    60
acugccuggu aaugaugacg gcggagcccu gcacg                               95

<210> SEQ ID NO 247
<211> LENGTH: 68
<212> TYPE: RNA
<213> ORGANISM: Homo sapiens

<400> SEQUENCE: 247
cccucgucuu acccagcagu guuugggugc gguugggagu cucuaauacu gccgguaau    60 gauggagg                                                             68

<210> SEQ ID NO 248
<211> LENGTH: 72
<212> TYPE: RNA
<213> ORGANISM: Homo sapiens

<400> SEQUENCE: 248
guuccuuuuu ccuaugcaua uacuucuuug aggaucuggc cuaaagaggu auagggcaug    60
ggaagaugga gc                                                        72

<210> SEQ ID NO 249
<211> LENGTH: 110
<212> TYPE: RNA
<213> ORGANISM: Homo sapiens

<400> SEQUENCE: 249 guguuggga cucgcgcgcu ggguccagug guucuuaaca guucaacagu ucuguagcgc    60
aauugugaaa uguuuaggac cacuagaccc ggcgggcgcg gcgacagcga              110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuucccuuu gcauccuau gccugagaau    60 auaugaagga ggcugggaag gcaaagggac guucaauugu caucacuggc              110

<210> SEQ ID NO 251
<211> LENGTH: 110
<212> TYPE: RNA
<213> ORGANISM: Homo sapiens

<400> SEQUENCE: 251

```
aaagauccuc agacaauuca ugugcuucuc uuguccuuca uuccaccgga gucugucuca    60
uacccaacca gauuucagug gagugaaguu caggaggcau ggagcugaca              110

<210> SEQ ID NO 252
<211> LENGTH: 86
<212> TYPE: RNA
<213> ORGANISM: Homo sapiens

<400> SEQUENCE: 252
ugcuucccga ggccacaugc uucuuuauau ccccauaugg auuacuuugc uauggaaugu    60
aaggaagugu gugguuucgg caagug                                        86

<210> SEQ ID NO 253
<211> LENGTH: 69
<212> TYPE: RNA
<213> ORGANISM: Homo sapiens

<400> SEQUENCE: 253
aggccacaug cuucuuuaua uccccauaug gauuacuuug cuauggaaug uaaggaagug    60
ugugguuuu                                                           69

<210> SEQ ID NO 254
<211> LENGTH: 71
<212> TYPE: RNA
<213> ORGANISM: Homo sapiens

<400> SEQUENCE: 254
ugacgggcga gcuuuuggcc cggguuauac cugaugcuca cguauaagac gagcaaaaag    60
cuuguugguc a                                                        71

<210> SEQ ID NO 255
<211> LENGTH: 110
<212> TYPE: RNA
<213> ORGANISM: Homo sapiens

<400> SEQUENCE: 255
acccggcagu gccuccaggc cagggcagc cccugcccac cgcacacugc gcugcccag      60 acccacugug cgugugacag cggcugaucu gugccugggc agcgcgaccc              110

<210> SEQ ID NO 256
<211> LENGTH: 110
<212> TYPE: RNA
<213> ORGANISM: Homo sapiens

<400> SEQUENCE: 256
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 257
<211> LENGTH: 110
<212> TYPE: RNA
<213> ORGANISM: Homo sapiens

<400> SEQUENCE: 257
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 258
<211> LENGTH: 110
```

```
<212> TYPE: RNA
<213> ORGANISM: Homo sapiens

<400> SEQUENCE: 258
ccugugcaga gauuauuuuu uaaaagguca caaucaacau ucauugcugu cgguggguug    60
aacugugugg acaagcucac ugaacaauga augcaacugu gggccccgcuu             110

<210> SEQ ID NO 259
<211> LENGTH: 108
<212> TYPE: RNA
<213> ORGANISM: Homo sapiens

<400> SEQUENCE: 259
gaguuuugag guugcuucag ugaacauuca acgcugucgg ugaguuugga auuaaaauca    60
aaaccaucga ccguugauug uacccuaugg cuaaccauca ucuacucc                108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc    60
gcucaccugu acagcaggca cagacaggca gucacaugac aacccagccu              110

<210> SEQ ID NO 261
<211> LENGTH: 110
<212> TYPE: RNA
<213> ORGANISM: Homo sapiens

<400> SEQUENCE: 261
aucauucaga aauggauauac aggaaaauga ccaugaauu gacagacaau auagcugagu    60
uugucuguca uuucuuuagg ccaauauucu guaugacugu gcuacuucaa              110

<210> SEQ ID NO 262
<211> LENGTH: 110
<212> TYPE: RNA
<213> ORGANISM: Homo sapiens

<400> SEQUENCE: 262
gauggcugug aguuggcuua aucucagcug gcaacuguga gauguucaua caaucccuca    60 cagggucuc ugggauuaug cuaaacagag caauuccua gcccucacga               110

<210> SEQ ID NO 263
<211> LENGTH: 110
<212> TYPE: RNA
<213> ORGANISM: Homo sapiens

<400> SEQUENCE: 263
aguauaauua uuacauaguu uuugaugucg cagauacugc aucaggaacu gauuggauaa    60
gaaucaguca ccaucaguuc cuaaugcauu gccuucagca ucuaaacaag              110

<210> SEQ ID NO 264
<211> LENGTH: 110
<212> TYPE: RNA
<213> ORGANISM: Homo sapiens

<400> SEQUENCE: 264
gugauaaugu agcgagauuu ucuguugugc uugaucuaac caugugguug cgagguauga    60
guaaaacaug guuccgucaa gcaccaugga acgucacgca gcuuucuaca              110
```

```
<210> SEQ ID NO 265
<211> LENGTH: 110
<212> TYPE: RNA
<213> ORGANISM: Homo sapiens

<400> SEQUENCE: 265
gaccagucgc ugcggggcuu uccuuugugc uugaucuaac caugugguggg aacgauggaa      60 acggaacaug guucugucaa gcaccgcgga aagcaccgug cucuccugca                  110

<210> SEQ ID NO 266
<211> LENGTH: 110
<212> TYPE: RNA
<213> ORGANISM: Homo sapiens

<400> SEQUENCE: 266
ccgccccggg ccgcggcucc ugauugucca aacgcaauuc ucgagucuau ggcuccggcc      60
gagaguugag ucuggacguc ccgagccgcc gcccccaaac cucgagcggg                  110

<210> SEQ ID NO 267
<211> LENGTH: 110
<212> TYPE: RNA
<213> ORGANISM: Homo sapiens

<400> SEQUENCE: 267
ccgccccggg ccgcggcucc ugauugucca aacgcaauuc ucgagucuau ggcuccggcc      60
gagaguugag ucuggacguc ccgagccgcc gcccccaaac cucgagcggg                  110

<210> SEQ ID NO 268
<211> LENGTH: 97
<212> TYPE: RNA
<213> ORGANISM: Homo sapiens

<400> SEQUENCE: 268
acucaggggc uucgccacug auuguccaaa cgcaauucuu guacgagucu gcggccaacc      60
gagaauugug gcuggacauc uguggcugag cuccggg                                97

<210> SEQ ID NO 269
<211> LENGTH: 110
<212> TYPE: RNA
<213> ORGANISM: Homo sapiens

<400> SEQUENCE: 269
gacagugugg cauuguaggg cuccacaccg uaucugacac uuugggcgag ggcaccaugc      60
ugaaggyguu caugaugcgg ucugggaacu ccucacggau cuuacugaug                  110

<210> SEQ ID NO 270
<211> LENGTH: 110
<212> TYPE: RNA
<213> ORGANISM: Homo sapiens

<400> SEQUENCE: 270
ugaacaucca ggucggggc augaaccugg cauacaaugu agauuucugu guucguuagg       60
caacagcuac auugucugcu ggguuucagg cuaccuggaa acauguucuc                  110

<210> SEQ ID NO 271
<211> LENGTH: 110
<212> TYPE: RNA
<213> ORGANISM: Homo sapiens

<400> SEQUENCE: 271
```

```
gcugcuggaa gguguaggua cccucaaugg cucaguagcc aguguagauc cugucuuucg    60
uaaucagcag cuacaucugg cuacuggguc ucgauggca ucuucuagcu                110

<210> SEQ ID NO 272
<211> LENGTH: 110
<212> TYPE: RNA
<213> ORGANISM: Homo sapiens

<400> SEQUENCE: 272
ccuggccucc ugcagugcca cgcuccgugu auuugacaag cugaguugga cacuccaugu    60
gguagagugu caguuuguca aauacacccaa gugcggcaca ugcuuaccag               110

<210> SEQ ID NO 273
<211> LENGTH: 81
<212> TYPE: RNA
<213> ORGANISM: Homo sapiens

<400> SEQUENCE: 273
gggcuuucaa gucacuagug guuccguuua guagaugauu gugcauuguu ucaaaauggu    60
gcccuaguga cuacaaagcc c                                              81

<210> SEQ ID NO 274
<211> LENGTH: 60
<212> TYPE: RNA
<213> ORGANISM: Homo sapiens

<400> SEQUENCE: 274
caaucuuccu uuaucauggu auugauuuuu cagugcuucc cuuugugug agagaagaua    60

<210> SEQ ID NO 275
<211> LENGTH: 80
<212> TYPE: RNA
<213> ORGANISM: Homo sapiens

<400> SEQUENCE: 275
aggacccuuc cagagggccc ccccucaauc cuguugugcc uaauucagag gguugggugg    60
aggcucuccu gaagggcucu                                                80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua ugugggaugg uaaaccgcuu    60
cuu                                                                  63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua    60
guauugucaa agcaucugaa agcagg                                         86

<210> SEQ ID NO 278
<211> LENGTH: 69
<212> TYPE: RNA
<213> ORGANISM: Homo sapiens
```

<400> SEQUENCE: 278
ccaccacuua aacguggaug uacuugcuuu gaaacuaaag aaguaagugc uuccauguuu    60
uggugaugg    69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucgugacuu uaaaaguaag ugcuuccaug    60
uuuuaguagg agu    73

<210> SEQ ID NO 280
<211> LENGTH: 68
<212> TYPE: RNA
<213> ORGANISM: Homo sapiens

<400> SEQUENCE: 280
ccuuugcuuu aacauggggg uaccugcugu gugaaacaaa aguaagugcu uccauguuuc    60
aguggagg    68

<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu    60
gagugugg    68

<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcuggguug    60
agagggcgaa aaaggaugag gu    82

<210> SEQ ID NO 283
<211> LENGTH: 59
<212> TYPE: RNA
<213> ORGANISM: Homo sapiens

<400> SEQUENCE: 283
uuggccuccu aagccaggga uuguggguuc gagucccacc cggguaaag aaaggccga    59

<210> SEQ ID NO 284
<211> LENGTH: 86
<212> TYPE: RNA
<213> ORGANISM: Homo sapiens

<400> SEQUENCE: 284
uugguacuug gagagagguug guccguggcg cguucgcuuu auuuauggcg cacauuacac    60
ggucgaccuc uuugcaguau cuaauc    86

<210> SEQ ID NO 285
<211> LENGTH: 83

```
<212> TYPE: RNA
<213> ORGANISM: Homo sapiens

<400> SEQUENCE: 285
cugacuaugc cuccccgcau ccccuagggc auugguguaa agcuggagac ccacugcccc     60
aggugcugcu gggggguugua guc                                            83

<210> SEQ ID NO 286
<211> LENGTH: 98
<212> TYPE: RNA
<213> ORGANISM: Homo sapiens

<400> SEQUENCE: 286
auacagugcu ugguuccuag uaggugucca guaaguguuu gugacauaau uuguuuauug     60
aggaccuccu aucaaucaag cacugugcua ggcucugg                             98

<210> SEQ ID NO 287
<211> LENGTH: 95
<212> TYPE: RNA
<213> ORGANISM: Homo sapiens

<400> SEQUENCE: 287
cucaucuguc uguugggcug gaggcagggc cuuugugaag gcggguggug cucagaucgc     60
cucugggccc uuccuccagc cccgaggcgg auuca                                95

<210> SEQ ID NO 288
<211> LENGTH: 75
<212> TYPE: RNA
<213> ORGANISM: Homo sapiens

<400> SEQUENCE: 288 uggaguggg gggcaggagg ggcucaggga gaaagugcau acagcccug gcccucucug      60 cccuuccguc cccug                                                      75

<210> SEQ ID NO 289
<211> LENGTH: 94
<212> TYPE: RNA
<213> ORGANISM: Homo sapiens

<400> SEQUENCE: 289
cuuuggcgau cacugcccucu cugggccugu gucuuaggcu cugcaagauc aaccgagcaa    60
agcacacggc cugcagagag gcagcgcucu gccc                                 94

<210> SEQ ID NO 290
<211> LENGTH: 94
<212> TYPE: RNA
<213> ORGANISM: Homo sapiens

<400> SEQUENCE: 290
gaguuugguu uuguuggggu uuguucuagg uaugguccca gggaucccag aucaaaccag    60
gccccugggc cuauccuaga accaaccuaa gcuc                                 94

<210> SEQ ID NO 291
<211> LENGTH: 94
<212> TYPE: RNA
<213> ORGANISM: Homo sapiens

<400> SEQUENCE: 291
uguuuugagc gggggucaag agcaauaacg aaaaauguuu gucauaaacc guuuucauu     60 auugcuccug accuccucuc auuugcuaua uuca                                 94
```

<210> SEQ ID NO 292
<211> LENGTH: 93
<212> TYPE: RNA
<213> ORGANISM: Homo sapiens

<400> SEQUENCE: 292
guagucagua guuggggggu gggaacggcu ucauacagga guugaugcac aguuauccag    60
cuccuauaug augccuuucu ucaucccuu caa                                  93

<210> SEQ ID NO 293
<211> LENGTH: 67
<212> TYPE: RNA
<213> ORGANISM: Homo sapiens

<400> SEQUENCE: 293
ucuccaacaa uauccuggug cugagugaug acucaggcga cuccagcauc agugauuug    60 uugaaga                                                              67

<210> SEQ ID NO 294
<211> LENGTH: 94
<212> TYPE: RNA
<213> ORGANISM: Homo sapiens

<400> SEQUENCE: 294
cggggcggcc gcucucccug uccuccagga gcucacgugu gccugccugu gagcgccucg    60
acgacagagc cggcgccugc cccagugucu gcgc                                94

<210> SEQ ID NO 295
<211> LENGTH: 95
<212> TYPE: RNA
<213> ORGANISM: Homo sapiens

<400> SEQUENCE: 295
uuguaccugg ugugauuaua aagcaaugag acugauuguc auaugucguu ugugggaucc    60
gucucaguua cuuuauagcc auaccuggua ucuua                               95

<210> SEQ ID NO 296
<211> LENGTH: 99
<212> TYPE: RNA
<213> ORGANISM: Homo sapiens

<400> SEQUENCE: 296
gaaacugggc ucaaggugag gggugcuauc ugugauugag ggacaugguu aauggaauug    60
ucucacacag aaaucgcacc cgucaccuug gccuacuua                           99

<210> SEQ ID NO 297
<211> LENGTH: 98
<212> TYPE: RNA
<213> ORGANISM: Homo sapiens

<400> SEQUENCE: 297
acccaaaccc uaggucugcu gacuccuagu ccagggcucg ugauggcugg ugggcccuga    60
acgagggguc uggaggccug gguuugaaua ucgacagc                            98

<210> SEQ ID NO 298
<211> LENGTH: 86
<212> TYPE: RNA
<213> ORGANISM: Homo sapiens

<400> SEQUENCE: 298

```
gucugucugc ccgcaugccu gccucucugu ugcucugaag gaggcagggg cugggccugc    60
agcugccugg gcagagcggc uccugc                                         86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau    60
ggugaugg                                                             68

<210> SEQ ID NO 300
<211> LENGTH: 66
<212> TYPE: RNA
<213> ORGANISM: Homo sapiens

<400> SEQUENCE: 300
aaaaggugga uauccuucu auguuuaugu uauuuauggu uaaacauaga ggaaauucca     60
cguuuu                                                               66

<210> SEQ ID NO 301
<211> LENGTH: 70
<212> TYPE: RNA
<213> ORGANISM: Homo sapiens

<400> SEQUENCE: 301
uugaagggag aucgaccgug uuauauucgc uuuauugacu ucgaauaaua cagguugau    60 cuuuucucag                                                           70

<210> SEQ ID NO 302
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug    60
gaaccugguc ugucu                                                     75

<210> SEQ ID NO 303
<211> LENGTH: 67
<212> TYPE: RNA
<213> ORGANISM: Homo sapiens

<400> SEQUENCE: 303
guggcacuca aacugggggg gcacuuucug cucucuggug aaagugccgc caucuuuga     60 guguuac                                                              67

<210> SEQ ID NO 304
<211> LENGTH: 67
<212> TYPE: RNA
<213> ORGANISM: Homo sapiens

<400> SEQUENCE: 304
gugggccuca aauguggagc acuauucuga uguccaagug gaaagugcug cgacauuuga    60
gcgucac                                                              67

<210> SEQ ID NO 305
<211> LENGTH: 69
```

-continued

```
<212> TYPE: RNA
<213> ORGANISM: Homo sapiens

<400> SEQUENCE: 305
gggauacuca aaauggggc gcuuccuuu uugucuguac ugggaagugc uucgauuuug    60
ggguguccc                                                          69

<210> SEQ ID NO 306
<211> LENGTH: 72
<212> TYPE: RNA
<213> ORGANISM: Homo sapiens

<400> SEQUENCE: 306
uacaucggcc auuauaauac aaccugauaa guguuauagc acuuaucaga uuguauugua    60
auugucugug ua                                                       72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucugaug uccaagugga    60
aagugcugcg acauuugagc gucaccggug acgcccauau ca                     102

<210> SEQ ID NO 308
<211> LENGTH: 101
<212> TYPE: RNA
<213> ORGANISM: Homo sapiens

<400> SEQUENCE: 308 gcaucccuc agccugugge acucaaacug uggggcacu uucugcucuc uggugaaagu    60
gccgccaucu uuugaguguu accgcuugag aagacucaac c                      101

<210> SEQ ID NO 309
<211> LENGTH: 102
<212> TYPE: RNA
<213> ORGANISM: Homo sapiens

<400> SEQUENCE: 309
cgaggagcuc auacugggau acucaaaaug ggggcgcuuu ccuuuuuguc uguuacuggg    60
aagugcuucg auuuuggggu gucccuguuu gaguagggca uc                     102

<210> SEQ ID NO 310
<211> LENGTH: 22
<212> TYPE: RNA
<213> ORGANISM: Homo sapiens

<400> SEQUENCE: 310
ugagguagua gguuguauag uu                                           22

<210> SEQ ID NO 311
<211> LENGTH: 22
<212> TYPE: RNA
<213> ORGANISM: Homo sapiens

<400> SEQUENCE: 311
ugagguagua gguugugugg uu                                           22

<210> SEQ ID NO 312
<211> LENGTH: 22
```

```
<212> TYPE: RNA
<213> ORGANISM: Homo sapiens

<400> SEQUENCE: 312
ugagguagua gguuguaugg uu                                           22

<210> SEQ ID NO 313
<211> LENGTH: 21
<212> TYPE: RNA
<213> ORGANISM: Homo sapiens

<400> SEQUENCE: 313
agagguagua gguugcauag u                                            21

<210> SEQ ID NO 314
<211> LENGTH: 21
<212> TYPE: RNA
<213> ORGANISM: Homo sapiens

<400> SEQUENCE: 314
ugagguagga gguuguauag u                                            21

<210> SEQ ID NO 315
<211> LENGTH: 22
<212> TYPE: RNA
<213> ORGANISM: Homo sapiens

<400> SEQUENCE: 315
ugagguagua gauuguauag uu                                           22

<210> SEQ ID NO 316
<211> LENGTH: 21
<212> TYPE: RNA
<213> ORGANISM: Homo sapiens

<400> SEQUENCE: 316
ugagguagua guuuguacag u                                            21

<210> SEQ ID NO 317
<211> LENGTH: 19
<212> TYPE: RNA
<213> ORGANISM: Homo sapiens

<400> SEQUENCE: 317
ugagguagua guuugugcu                                               19

<210> SEQ ID NO 318
<211> LENGTH: 21
<212> TYPE: RNA
<213> ORGANISM: Homo sapiens

<400> SEQUENCE: 318
uggaauguaa agaaguaugu a                                            21

<210> SEQ ID NO 319
<211> LENGTH: 21
<212> TYPE: RNA
<213> ORGANISM: Homo sapiens

<400> SEQUENCE: 319
uggaagacua gugauuuugu u                                            21

<210> SEQ ID NO 320
<211> LENGTH: 23
```

```
<212> TYPE: RNA
<213> ORGANISM: Homo sapiens

<400> SEQUENCE: 320
ucuuugguua ucuagcugua uga                                          23

<210> SEQ ID NO 321
<211> LENGTH: 21
<212> TYPE: RNA
<213> ORGANISM: Homo sapiens

<400> SEQUENCE: 321
uaaagcuaga uaaccgaaag u                                            21

<210> SEQ ID NO 322
<211> LENGTH: 23
<212> TYPE: RNA
<213> ORGANISM: Homo sapiens

<400> SEQUENCE: 322
uacccuguag auccgaauuu gug                                          23

<210> SEQ ID NO 323
<211> LENGTH: 22
<212> TYPE: RNA
<213> ORGANISM: Homo sapiens

<400> SEQUENCE: 323
uacccuguag aaccgaauuu gu                                           22

<210> SEQ ID NO 324
<211> LENGTH: 22
<212> TYPE: RNA
<213> ORGANISM: Homo sapiens

<400> SEQUENCE: 324
uagcagcaca uaaugguuug ug                                           22

<210> SEQ ID NO 325
<211> LENGTH: 22
<212> TYPE: RNA
<213> ORGANISM: Homo sapiens

<400> SEQUENCE: 325
uagcagcaca ucaugguuua ca                                           22

<210> SEQ ID NO 326
<211> LENGTH: 22
<212> TYPE: RNA
<213> ORGANISM: Homo sapiens

<400> SEQUENCE: 326
uagcagcacg uaaauauugg cg                                           22

<210> SEQ ID NO 327
<211> LENGTH: 24
<212> TYPE: RNA
<213> ORGANISM: Homo sapiens

<400> SEQUENCE: 327
caaagugcuu acagugcagg uagu                                         24

<210> SEQ ID NO 328
<211> LENGTH: 20
```

```
<212> TYPE: RNA
<213> ORGANISM: Homo sapiens

<400> SEQUENCE: 328
acugcaguga aggcacuugu                                               20

<210> SEQ ID NO 329
<211> LENGTH: 22
<212> TYPE: RNA
<213> ORGANISM: Homo sapiens

<400> SEQUENCE: 329
uaaggugcau cuagugcaga ua                                            22

<210> SEQ ID NO 330
<211> LENGTH: 23
<212> TYPE: RNA
<213> ORGANISM: Homo sapiens

<400> SEQUENCE: 330
ugugcaaauc uaugcaaaac uga                                           23

<210> SEQ ID NO 331
<211> LENGTH: 23
<212> TYPE: RNA
<213> ORGANISM: Homo sapiens

<400> SEQUENCE: 331
ugugcaaauc caugcaaaac uga                                           23

<210> SEQ ID NO 332
<211> LENGTH: 22
<212> TYPE: RNA
<213> ORGANISM: Homo sapiens

<400> SEQUENCE: 332
uaaagugcuu auagugcagg ua                                            22

<210> SEQ ID NO 333
<211> LENGTH: 22
<212> TYPE: RNA
<213> ORGANISM: Homo sapiens

<400> SEQUENCE: 333
uagcuuauca gacugauguu ga                                            22

<210> SEQ ID NO 334
<211> LENGTH: 22
<212> TYPE: RNA
<213> ORGANISM: Homo sapiens

<400> SEQUENCE: 334
aagcugccag uugaagaacu gu                                            22

<210> SEQ ID NO 335
<211> LENGTH: 21
<212> TYPE: RNA
<213> ORGANISM: Homo sapiens

<400> SEQUENCE: 335
aucacauugc cagggauuuc c                                             21

<210> SEQ ID NO 336
<211> LENGTH: 23
```

```
<212> TYPE: RNA
<213> ORGANISM: Homo sapiens

<400> SEQUENCE: 336
aucacauugc cagggauuac cac                                          23

<210> SEQ ID NO 337
<211> LENGTH: 22
<212> TYPE: RNA
<213> ORGANISM: Homo sapiens

<400> SEQUENCE: 337
uggcucaguu cagcaggaac ag                                           22

<210> SEQ ID NO 338
<211> LENGTH: 22
<212> TYPE: RNA
<213> ORGANISM: Homo sapiens

<400> SEQUENCE: 338
cauugcacuu gucucggucu ga                                           22

<210> SEQ ID NO 339
<211> LENGTH: 22
<212> TYPE: RNA
<213> ORGANISM: Homo sapiens

<400> SEQUENCE: 339
uucaaguaau ccaggauagg cu                                           22

<210> SEQ ID NO 340
<211> LENGTH: 21
<212> TYPE: RNA
<213> ORGANISM: Homo sapiens

<400> SEQUENCE: 340
uucaaguaau ucaggauagg u                                            21

<210> SEQ ID NO 341
<211> LENGTH: 22
<212> TYPE: RNA
<213> ORGANISM: Homo sapiens

<400> SEQUENCE: 341
uucacagugg cuaaguuccg cc                                           22

<210> SEQ ID NO 342
<211> LENGTH: 20
<212> TYPE: RNA
<213> ORGANISM: Homo sapiens

<400> SEQUENCE: 342
uucacagugg cuaaguucug                                              20

<210> SEQ ID NO 343
<211> LENGTH: 22
<212> TYPE: RNA
<213> ORGANISM: Homo sapiens

<400> SEQUENCE: 343
aaggagcuca cagucuauug ag                                           22

<210> SEQ ID NO 344
<211> LENGTH: 22
```

```
<212> TYPE: RNA
<213> ORGANISM: Homo sapiens

<400> SEQUENCE: 344
cuagcaccau cugaaaucgg uu                                          22

<210> SEQ ID NO 345
<211> LENGTH: 20
<212> TYPE: RNA
<213> ORGANISM: Homo sapiens

<400> SEQUENCE: 345
uagcaccauu ugaaaucagu                                             20

<210> SEQ ID NO 346
<211> LENGTH: 22
<212> TYPE: RNA
<213> ORGANISM: Homo sapiens

<400> SEQUENCE: 346
uagcaccauu ugaaaucggu ua                                          22

<210> SEQ ID NO 347
<211> LENGTH: 23
<212> TYPE: RNA
<213> ORGANISM: Homo sapiens

<400> SEQUENCE: 347
uguaaacauc cucgacugga agc                                         23

<210> SEQ ID NO 348
<211> LENGTH: 22
<212> TYPE: RNA
<213> ORGANISM: Homo sapiens

<400> SEQUENCE: 348
cuuucagucg gauguuugca gc                                          22

<210> SEQ ID NO 349
<211> LENGTH: 21
<212> TYPE: RNA
<213> ORGANISM: Homo sapiens

<400> SEQUENCE: 349
uguaaacauc cuacacucag c                                           21

<210> SEQ ID NO 350
<211> LENGTH: 23
<212> TYPE: RNA
<213> ORGANISM: Homo sapiens

<400> SEQUENCE: 350
uguaaacauc cuacacucuc agc                                         23

<210> SEQ ID NO 351
<211> LENGTH: 22
<212> TYPE: RNA
<213> ORGANISM: Homo sapiens

<400> SEQUENCE: 351
uguaaacauc cccgacugga ag                                          22

<210> SEQ ID NO 352
<211> LENGTH: 20
```

```
<212> TYPE: RNA
<213> ORGANISM: Homo sapiens

<400> SEQUENCE: 352
uguaaacauc cuugacugga                                              20

<210> SEQ ID NO 353
<211> LENGTH: 21
<212> TYPE: RNA
<213> ORGANISM: Homo sapiens

<400> SEQUENCE: 353
ggcaagaugc uggcauagcu g                                            21

<210> SEQ ID NO 354
<211> LENGTH: 21
<212> TYPE: RNA
<213> ORGANISM: Homo sapiens

<400> SEQUENCE: 354
uauugcacau uacuaaguug c                                            21

<210> SEQ ID NO 355
<211> LENGTH: 19
<212> TYPE: RNA
<213> ORGANISM: Homo sapiens

<400> SEQUENCE: 355
gugcauugua guugcauug                                               19

<210> SEQ ID NO 356
<211> LENGTH: 22
<212> TYPE: RNA
<213> ORGANISM: Homo sapiens

<400> SEQUENCE: 356
uggcaguguc uuagcgguu gu                                            22

<210> SEQ ID NO 357
<211> LENGTH: 22
<212> TYPE: RNA
<213> ORGANISM: Homo sapiens

<400> SEQUENCE: 357
aggcaguguc auuagcugau ug                                           22

<210> SEQ ID NO 358
<211> LENGTH: 22
<212> TYPE: RNA
<213> ORGANISM: Homo sapiens

<400> SEQUENCE: 358
aggcagugua guuagcugau ug                                           22

<210> SEQ ID NO 359
<211> LENGTH: 22
<212> TYPE: RNA
<213> ORGANISM: Homo sapiens

<400> SEQUENCE: 359
uauugcacuu gucccggccu gu                                           22

<210> SEQ ID NO 360
<211> LENGTH: 22
```

```
<212> TYPE: RNA
<213> ORGANISM: Homo sapiens

<400> SEQUENCE: 360
aaagugcugu ucgugcaggu ag                                              22

<210> SEQ ID NO 361
<211> LENGTH: 22
<212> TYPE: RNA
<213> ORGANISM: Homo sapiens

<400> SEQUENCE: 361
uucaacgggu auuuauugag ca                                              22

<210> SEQ ID NO 362
<211> LENGTH: 22
<212> TYPE: RNA
<213> ORGANISM: Homo sapiens

<400> SEQUENCE: 362
uuuggcacua gcacauuuuu gc                                              22

<210> SEQ ID NO 363
<211> LENGTH: 22
<212> TYPE: RNA
<213> ORGANISM: Homo sapiens

<400> SEQUENCE: 363
ugagguagua aguuguauug uu                                              22

<210> SEQ ID NO 364
<211> LENGTH: 22
<212> TYPE: RNA
<213> ORGANISM: Homo sapiens

<400> SEQUENCE: 364
aacccguaga uccgaucuug ug                                              22

<210> SEQ ID NO 365
<211> LENGTH: 22
<212> TYPE: RNA
<213> ORGANISM: Homo sapiens

<400> SEQUENCE: 365
cacccguaga accgaccuug cg                                              22

<210> SEQ ID NO 366
<211> LENGTH: 22
<212> TYPE: RNA
<213> ORGANISM: Homo sapiens

<400> SEQUENCE: 366
uacaguacug ugauaacuga ag                                              22

<210> SEQ ID NO 367
<211> LENGTH: 22
<212> TYPE: RNA
<213> ORGANISM: Homo sapiens

<400> SEQUENCE: 367
uacaguacug ugauaacuga ag                                              22

<210> SEQ ID NO 368
<211> LENGTH: 23
```

```
<212> TYPE: RNA
<213> ORGANISM: Homo sapiens

<400> SEQUENCE: 368
agcagcauug uacagggcua uga                                            23

<210> SEQ ID NO 369
<211> LENGTH: 20
<212> TYPE: RNA
<213> ORGANISM: Homo sapiens

<400> SEQUENCE: 369
ucaaaugcuc agacuccugu                                                20

<210> SEQ ID NO 370
<211> LENGTH: 24
<212> TYPE: RNA
<213> ORGANISM: Homo sapiens

<400> SEQUENCE: 370
aaaagugcuu acagugcagg uagc                                           24

<210> SEQ ID NO 371
<211> LENGTH: 21
<212> TYPE: RNA
<213> ORGANISM: Homo sapiens

<400> SEQUENCE: 371
uaaagugcug acagugcaga u                                              21

<210> SEQ ID NO 372
<211> LENGTH: 23
<212> TYPE: RNA
<213> ORGANISM: Homo sapiens

<400> SEQUENCE: 372
agcagcauug uacagggcua uca                                            23

<210> SEQ ID NO 373
<211> LENGTH: 23
<212> TYPE: RNA
<213> ORGANISM: Homo sapiens

<400> SEQUENCE: 373
uggaguguga caaugguguu ugu                                            23

<210> SEQ ID NO 374
<211> LENGTH: 22
<212> TYPE: RNA
<213> ORGANISM: Homo sapiens

<400> SEQUENCE: 374
uuaaggcacg cggugaaugc ca                                             22

<210> SEQ ID NO 375
<211> LENGTH: 23
<212> TYPE: RNA
<213> ORGANISM: Homo sapiens

<400> SEQUENCE: 375
ucccugagac ccuuuaaccu gug                                            23

<210> SEQ ID NO 376
<211> LENGTH: 22
```

```
<212> TYPE: RNA
<213> ORGANISM: Homo sapiens

<400> SEQUENCE: 376
ucccugagac ccuaacuugu ga                                              22

<210> SEQ ID NO 377
<211> LENGTH: 21
<212> TYPE: RNA
<213> ORGANISM: Homo sapiens

<400> SEQUENCE: 377
cauuauuacu uuugguacgc g                                               21

<210> SEQ ID NO 378
<211> LENGTH: 21
<212> TYPE: RNA
<213> ORGANISM: Homo sapiens

<400> SEQUENCE: 378
ucguaccgug aguaauaaug c                                               21

<210> SEQ ID NO 379
<211> LENGTH: 22
<212> TYPE: RNA
<213> ORGANISM: Homo sapiens

<400> SEQUENCE: 379
ucggauccgu cugagcuugg cu                                              22

<210> SEQ ID NO 380
<211> LENGTH: 22
<212> TYPE: RNA
<213> ORGANISM: Homo sapiens

<400> SEQUENCE: 380
ucacagugaa ccggucucuu uu                                              22

<210> SEQ ID NO 381
<211> LENGTH: 22
<212> TYPE: RNA
<213> ORGANISM: Homo sapiens

<400> SEQUENCE: 381
ucacagugaa ccggucucuu uc                                              22

<210> SEQ ID NO 382
<211> LENGTH: 21
<212> TYPE: RNA
<213> ORGANISM: Homo sapiens

<400> SEQUENCE: 382
cuuuuugcgg ucugggcuug c                                               21

<210> SEQ ID NO 383
<211> LENGTH: 20
<212> TYPE: RNA
<213> ORGANISM: Homo sapiens

<400> SEQUENCE: 383
cagugcaaug uuaaaagggc                                                 20

<210> SEQ ID NO 384
<211> LENGTH: 22
```

```
<212> TYPE: RNA
<213> ORGANISM: Homo sapiens

<400> SEQUENCE: 384
cagugcaaug augaaagggc au                                              22

<210> SEQ ID NO 385
<211> LENGTH: 22
<212> TYPE: RNA
<213> ORGANISM: Homo sapiens

<400> SEQUENCE: 385
uaacagucua cagccauggu cg                                              22

<210> SEQ ID NO 386
<211> LENGTH: 22
<212> TYPE: RNA
<213> ORGANISM: Homo sapiens

<400> SEQUENCE: 386
uugguccccu ucaaccagcu gu                                              22

<210> SEQ ID NO 387
<211> LENGTH: 21
<212> TYPE: RNA
<213> ORGANISM: Homo sapiens

<400> SEQUENCE: 387
uugguccccu ucaaccagcu a                                               21

<210> SEQ ID NO 388
<211> LENGTH: 21
<212> TYPE: RNA
<213> ORGANISM: Homo sapiens

<400> SEQUENCE: 388
ugugacuggu ugaccagagg g                                               21

<210> SEQ ID NO 389
<211> LENGTH: 23
<212> TYPE: RNA
<213> ORGANISM: Homo sapiens

<400> SEQUENCE: 389
uauggcuuuu uauuccuaug uga                                             23

<210> SEQ ID NO 390
<211> LENGTH: 22
<212> TYPE: RNA
<213> ORGANISM: Homo sapiens

<400> SEQUENCE: 390
uauggcuuuu cauuccuaug ug                                              22

<210> SEQ ID NO 391
<211> LENGTH: 23
<212> TYPE: RNA
<213> ORGANISM: Homo sapiens

<400> SEQUENCE: 391
acuccauuug uuuugaugau gga                                             23

<210> SEQ ID NO 392
<211> LENGTH: 22
```

```
<212> TYPE: RNA
<213> ORGANISM: Homo sapiens

<400> SEQUENCE: 392
uauugcuuaa gaauacgcgu ag                                    22

<210> SEQ ID NO 393
<211> LENGTH: 17
<212> TYPE: RNA
<213> ORGANISM: Homo sapiens

<400> SEQUENCE: 393
agcugguguu gugaauc                                          17

<210> SEQ ID NO 394
<211> LENGTH: 18
<212> TYPE: RNA
<213> ORGANISM: Homo sapiens

<400> SEQUENCE: 394
ucuacagugc acgugucu                                         18

<210> SEQ ID NO 395
<211> LENGTH: 21
<212> TYPE: RNA
<213> ORGANISM: Homo sapiens

<400> SEQUENCE: 395
agugguuuua cccuauggua g                                     21

<210> SEQ ID NO 396
<211> LENGTH: 21
<212> TYPE: RNA
<213> ORGANISM: Homo sapiens

<400> SEQUENCE: 396
aacacugucu gguaaagaug g                                     21

<210> SEQ ID NO 397
<211> LENGTH: 23
<212> TYPE: RNA
<213> ORGANISM: Homo sapiens

<400> SEQUENCE: 397
uguaguguuu ccuacuuuau gga                                   23

<210> SEQ ID NO 398
<211> LENGTH: 20
<212> TYPE: RNA
<213> ORGANISM: Homo sapiens

<400> SEQUENCE: 398
cauaaaguag aaagcacuac                                       20

<210> SEQ ID NO 399
<211> LENGTH: 22
<212> TYPE: RNA
<213> ORGANISM: Homo sapiens

<400> SEQUENCE: 399
ugagaugaag cacuguagcu ca                                    22

<210> SEQ ID NO 400
<211> LENGTH: 22
```

```
<212> TYPE: RNA
<213> ORGANISM: Homo sapiens

<400> SEQUENCE: 400
uacaguauag augauguacu ag                                              22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu                                            24

<210> SEQ ID NO 402
<211> LENGTH: 22
<212> TYPE: RNA
<213> ORGANISM: Homo sapiens

<400> SEQUENCE: 402
ugagaacuga auccaugggg uu                                              22

<210> SEQ ID NO 403
<211> LENGTH: 20
<212> TYPE: RNA
<213> ORGANISM: Homo sapiens

<400> SEQUENCE: 403
guguguggaa augcuucugc                                                 20

<210> SEQ ID NO 404
<211> LENGTH: 22
<212> TYPE: RNA
<213> ORGANISM: Homo sapiens

<400> SEQUENCE: 404
ucagugcacu acagaacuuu gu                                              22

<210> SEQ ID NO 405
<211> LENGTH: 22
<212> TYPE: RNA
<213> ORGANISM: Homo sapiens

<400> SEQUENCE: 405
ucagugcauc acagaacuuu gu                                              22

<210> SEQ ID NO 406
<211> LENGTH: 22
<212> TYPE: RNA
<213> ORGANISM: Homo sapiens

<400> SEQUENCE: 406
ucuggcuccg ugucuucacu cc                                              22

<210> SEQ ID NO 407
<211> LENGTH: 22
<212> TYPE: RNA
<213> ORGANISM: Homo sapiens

<400> SEQUENCE: 407
ucucccaacc cuuguaccag ug                                              22

<210> SEQ ID NO 408
<211> LENGTH: 22
```

<212> TYPE: RNA
<213> ORGANISM: Homo sapiens

<400> SEQUENCE: 408
acuagacuga agcccuuga gg                                        22

<210> SEQ ID NO 409
<211> LENGTH: 21
<212> TYPE: RNA
<213> ORGANISM: Homo sapiens

<400> SEQUENCE: 409
ucagugcaug acagaacuug g                                        21

<210> SEQ ID NO 410
<211> LENGTH: 20
<212> TYPE: RNA
<213> ORGANISM: Homo sapiens

<400> SEQUENCE: 410
uugcauaguc acaaaaguga                                          20

<210> SEQ ID NO 411
<211> LENGTH: 22
<212> TYPE: RNA
<213> ORGANISM: Homo sapiens

<400> SEQUENCE: 411
uagguuaucc guguugccuu cg                                       22

<210> SEQ ID NO 412
<211> LENGTH: 22
<212> TYPE: RNA
<213> ORGANISM: Homo sapiens

<400> SEQUENCE: 412
aaucauacac gguugaccua uu                                       22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg                                       22

<210> SEQ ID NO 414
<211> LENGTH: 23
<212> TYPE: RNA
<213> ORGANISM: Homo sapiens

<400> SEQUENCE: 414
aacauucaac gcugucggug agu                                      23

<210> SEQ ID NO 415
<211> LENGTH: 24
<212> TYPE: RNA
<213> ORGANISM: Homo sapiens

<400> SEQUENCE: 415
aacauucauu gcugucggug gguu                                     24

<210> SEQ ID NO 416
<211> LENGTH: 22

```
<212> TYPE: RNA
<213> ORGANISM: Homo sapiens

<400> SEQUENCE: 416
aacauucaac cugucgguga gu                                      22

<210> SEQ ID NO 417
<211> LENGTH: 22
<212> TYPE: RNA
<213> ORGANISM: Homo sapiens

<400> SEQUENCE: 417
uuuggcaaug guagaacuca ca                                      22

<210> SEQ ID NO 418
<211> LENGTH: 21
<212> TYPE: RNA
<213> ORGANISM: Homo sapiens

<400> SEQUENCE: 418
ugguucuaga cuugccaacu a                                       21

<210> SEQ ID NO 419
<211> LENGTH: 23
<212> TYPE: RNA
<213> ORGANISM: Homo sapiens

<400> SEQUENCE: 419
uauggcacug guagaauuca cug                                     23

<210> SEQ ID NO 420
<211> LENGTH: 22
<212> TYPE: RNA
<213> ORGANISM: Homo sapiens

<400> SEQUENCE: 420
uggacggaga acugauaagg gu                                      22

<210> SEQ ID NO 421
<211> LENGTH: 18
<212> TYPE: RNA
<213> ORGANISM: Homo sapiens

<400> SEQUENCE: 421
uggagagaaa ggcaguuc                                           18

<210> SEQ ID NO 422
<211> LENGTH: 23
<212> TYPE: RNA
<213> ORGANISM: Homo sapiens

<400> SEQUENCE: 422
caaagaauuc uccuuuuggg cuu                                     23

<210> SEQ ID NO 423
<211> LENGTH: 21
<212> TYPE: RNA
<213> ORGANISM: Homo sapiens

<400> SEQUENCE: 423
ucgugucuug uguugcagcc g                                       21

<210> SEQ ID NO 424
<211> LENGTH: 22
```

```
<212> TYPE: RNA
<213> ORGANISM: Homo sapiens

<400> SEQUENCE: 424
caucccuugc augguggagg gu                                              22

<210> SEQ ID NO 425
<211> LENGTH: 23
<212> TYPE: RNA
<213> ORGANISM: Homo sapiens

<400> SEQUENCE: 425
gugccuacug agcugauauc agu                                             23

<210> SEQ ID NO 426
<211> LENGTH: 22
<212> TYPE: RNA
<213> ORGANISM: Homo sapiens

<400> SEQUENCE: 426
ugauauguuu gauauauuag gu                                              22

<210> SEQ ID NO 427
<211> LENGTH: 22
<212> TYPE: RNA
<213> ORGANISM: Homo sapiens

<400> SEQUENCE: 427
caacggaauc ccaaaagcag cu                                              22

<210> SEQ ID NO 428
<211> LENGTH: 21
<212> TYPE: RNA
<213> ORGANISM: Homo sapiens

<400> SEQUENCE: 428
cugaccuaug aauugacagc c                                               21

<210> SEQ ID NO 429
<211> LENGTH: 21
<212> TYPE: RNA
<213> ORGANISM: Homo sapiens

<400> SEQUENCE: 429
aacuggccua caaaguccca g                                               21

<210> SEQ ID NO 430
<211> LENGTH: 22
<212> TYPE: RNA
<213> ORGANISM: Homo sapiens

<400> SEQUENCE: 430
uguaacagca acuccaugug ga                                              22

<210> SEQ ID NO 431
<211> LENGTH: 21
<212> TYPE: RNA
<213> ORGANISM: Homo sapiens

<400> SEQUENCE: 431
uagcagcaca gaaauauugg c                                               21

<210> SEQ ID NO 432
<211> LENGTH: 21
```

```
<212> TYPE: RNA
<213> ORGANISM: Homo sapiens

<400> SEQUENCE: 432
uagguaguuu cauguuguug g                                      21

<210> SEQ ID NO 433
<211> LENGTH: 21
<212> TYPE: RNA
<213> ORGANISM: Homo sapiens

<400> SEQUENCE: 433
uagguaguuu ccuguuguug g                                      21

<210> SEQ ID NO 434
<211> LENGTH: 22
<212> TYPE: RNA
<213> ORGANISM: Homo sapiens

<400> SEQUENCE: 434
uucaccaccu ucuccaccca gc                                     22

<210> SEQ ID NO 435
<211> LENGTH: 19
<212> TYPE: RNA
<213> ORGANISM: Homo sapiens

<400> SEQUENCE: 435
gguccagagg ggagauagg                                         19

<210> SEQ ID NO 436
<211> LENGTH: 23
<212> TYPE: RNA
<213> ORGANISM: Homo sapiens

<400> SEQUENCE: 436
cccaguguuc agacuaccug uuc                                    23

<210> SEQ ID NO 437
<211> LENGTH: 22
<212> TYPE: RNA
<213> ORGANISM: Homo sapiens

<400> SEQUENCE: 437
uacaguaguc ugcacauugg uu                                     22

<210> SEQ ID NO 438
<211> LENGTH: 23
<212> TYPE: RNA
<213> ORGANISM: Homo sapiens

<400> SEQUENCE: 438
cccaguguuu agacuaucug uuc                                    23

<210> SEQ ID NO 439
<211> LENGTH: 22
<212> TYPE: RNA
<213> ORGANISM: Homo sapiens

<400> SEQUENCE: 439
uaacacuguc ugguaacgau gu                                     22

<210> SEQ ID NO 440
<211> LENGTH: 24
```

```
<212> TYPE: RNA
<213> ORGANISM: Homo sapiens

<400> SEQUENCE: 440
cucuaauacu gccugguaau gaug                                          24

<210> SEQ ID NO 441
<211> LENGTH: 22
<212> TYPE: RNA
<213> ORGANISM: Homo sapiens

<400> SEQUENCE: 441
aauacugccg gguaaugaug ga                                            22

<210> SEQ ID NO 442
<211> LENGTH: 22
<212> TYPE: RNA
<213> ORGANISM: Homo sapiens

<400> SEQUENCE: 442
agagguauag ggcaugggaa ga                                            22

<210> SEQ ID NO 443
<211> LENGTH: 22
<212> TYPE: RNA
<213> ORGANISM: Homo sapiens

<400> SEQUENCE: 443
gugaaauguu uaggaccacu ag                                            22

<210> SEQ ID NO 444
<211> LENGTH: 22
<212> TYPE: RNA
<213> ORGANISM: Homo sapiens

<400> SEQUENCE: 444
uucccuuugu cauccuaugc cu                                            22

<210> SEQ ID NO 445
<211> LENGTH: 22
<212> TYPE: RNA
<213> ORGANISM: Homo sapiens

<400> SEQUENCE: 445
uccuucauuc caccggaguc ug                                            22

<210> SEQ ID NO 446
<211> LENGTH: 22
<212> TYPE: RNA
<213> ORGANISM: Homo sapiens

<400> SEQUENCE: 446
uggaauguaa ggaagugugu gg                                            22

<210> SEQ ID NO 447
<211> LENGTH: 22
<212> TYPE: RNA
<213> ORGANISM: Homo sapiens

<400> SEQUENCE: 447
auaagacgag caaaaagcuu gu                                            22

<210> SEQ ID NO 448
<211> LENGTH: 21
```

```
<212> TYPE: RNA
<213> ORGANISM: Homo sapiens

<400> SEQUENCE: 448
cugugcgugu gacagcggcu g                                        21

<210> SEQ ID NO 449
<211> LENGTH: 22
<212> TYPE: RNA
<213> ORGANISM: Homo sapiens

<400> SEQUENCE: 449
uucccuuugu cauccuucgc cu                                       22

<210> SEQ ID NO 450
<211> LENGTH: 21
<212> TYPE: RNA
<213> ORGANISM: Homo sapiens

<400> SEQUENCE: 450
uaacagucuc cagucacggc c                                        21

<210> SEQ ID NO 451
<211> LENGTH: 22
<212> TYPE: RNA
<213> ORGANISM: Homo sapiens

<400> SEQUENCE: 451
accaucgacc guugauugua cc                                       22

<210> SEQ ID NO 452
<211> LENGTH: 21
<212> TYPE: RNA
<213> ORGANISM: Homo sapiens

<400> SEQUENCE: 452
acagcaggca cagacaggca g                                        21

<210> SEQ ID NO 453
<211> LENGTH: 21
<212> TYPE: RNA
<213> ORGANISM: Homo sapiens

<400> SEQUENCE: 453
augaccuaug aauugacaga c                                        21

<210> SEQ ID NO 454
<211> LENGTH: 21
<212> TYPE: RNA
<213> ORGANISM: Homo sapiens

<400> SEQUENCE: 454
uaaucucagc uggcaacugu g                                        21

<210> SEQ ID NO 455
<211> LENGTH: 24
<212> TYPE: RNA
<213> ORGANISM: Homo sapiens

<400> SEQUENCE: 455
uacugcauca ggaacugauu ggau                                     24

<210> SEQ ID NO 456
<211> LENGTH: 21
```

```
<212> TYPE: RNA
<213> ORGANISM: Homo sapiens

<400> SEQUENCE: 456
uugugcuuga ucuaaccaug u                                              21

<210> SEQ ID NO 457
<211> LENGTH: 21
<212> TYPE: RNA
<213> ORGANISM: Homo sapiens

<400> SEQUENCE: 457
ugauugucca aacgcaauuc u                                              21

<210> SEQ ID NO 458
<211> LENGTH: 21
<212> TYPE: RNA
<213> ORGANISM: Homo sapiens

<400> SEQUENCE: 458
ccacaccgua ucugacacuu u                                              21

<210> SEQ ID NO 459
<211> LENGTH: 23
<212> TYPE: RNA
<213> ORGANISM: Homo sapiens

<400> SEQUENCE: 459
agcuacauug ucugcugggu uuc                                            23

<210> SEQ ID NO 460
<211> LENGTH: 24
<212> TYPE: RNA
<213> ORGANISM: Homo sapiens

<400> SEQUENCE: 460
agcuacaucu ggcuacuggg ucuc                                           24

<210> SEQ ID NO 461
<211> LENGTH: 21
<212> TYPE: RNA
<213> ORGANISM: Homo sapiens

<400> SEQUENCE: 461
ugucaguuug ucaaauaccc c                                              21

<210> SEQ ID NO 462
<211> LENGTH: 23
<212> TYPE: RNA
<213> ORGANISM: Homo sapiens

<400> SEQUENCE: 462
caagucacua gugguuccgu uua                                            23

<210> SEQ ID NO 463
<211> LENGTH: 21
<212> TYPE: RNA
<213> ORGANISM: Homo sapiens

<400> SEQUENCE: 463
agggcccccc cucaauccug u                                              21

<210> SEQ ID NO 464
<211> LENGTH: 22
```

```
<212> TYPE: RNA
<213> ORGANISM: Homo sapiens

<400> SEQUENCE: 464
ugguuuaccg ucccacauac au                                           22

<210> SEQ ID NO 465
<211> LENGTH: 23
<212> TYPE: RNA
<213> ORGANISM: Homo sapiens

<400> SEQUENCE: 465
cagugcaaua guauugucaa agc                                          23

<210> SEQ ID NO 466
<211> LENGTH: 23
<212> TYPE: RNA
<213> ORGANISM: Homo sapiens

<400> SEQUENCE: 466
uaagugcuuc cauguuuugg uga                                          23

<210> SEQ ID NO 467
<211> LENGTH: 23
<212> TYPE: RNA
<213> ORGANISM: Homo sapiens

<400> SEQUENCE: 467
acuuuaacau ggaagugcuu ucu                                          23

<210> SEQ ID NO 468
<211> LENGTH: 23
<212> TYPE: RNA
<213> ORGANISM: Homo sapiens

<400> SEQUENCE: 468
uaagugcuuc cauguuuag uag                                           23

<210> SEQ ID NO 469
<211> LENGTH: 22
<212> TYPE: RNA
<213> ORGANISM: Homo sapiens

<400> SEQUENCE: 469
uuuaacaugg ggguaccugc ug                                           22

<210> SEQ ID NO 470
<211> LENGTH: 23
<212> TYPE: RNA
<213> ORGANISM: Homo sapiens

<400> SEQUENCE: 470
uaagugcuuc cauguuucag ugg                                          23

<210> SEQ ID NO 471
<211> LENGTH: 23
<212> TYPE: RNA
<213> ORGANISM: Homo sapiens

<400> SEQUENCE: 471
uaagugcuuc cauguuugag ugu                                          23

<210> SEQ ID NO 472
<211> LENGTH: 23
```

```
<212> TYPE: RNA
<213> ORGANISM: Homo sapiens

<400> SEQUENCE: 472
aaaagcuggg uugagagggc gaa                                      23

<210> SEQ ID NO 473
<211> LENGTH: 21
<212> TYPE: RNA
<213> ORGANISM: Homo sapiens

<400> SEQUENCE: 473
uaagccaggg auuguggguu c                                        21

<210> SEQ ID NO 474
<211> LENGTH: 22
<212> TYPE: RNA
<213> ORGANISM: Homo sapiens

<400> SEQUENCE: 474
gcacauuaca cggucgaccu cu                                       22

<210> SEQ ID NO 475
<211> LENGTH: 23
<212> TYPE: RNA
<213> ORGANISM: Homo sapiens

<400> SEQUENCE: 475
cgcauccccu agggcauugg ugu                                      23

<210> SEQ ID NO 476
<211> LENGTH: 22
<212> TYPE: RNA
<213> ORGANISM: Homo sapiens

<400> SEQUENCE: 476
ccacugcccc aggugcugcu gg                                       22

<210> SEQ ID NO 477
<211> LENGTH: 21
<212> TYPE: RNA
<213> ORGANISM: Homo sapiens

<400> SEQUENCE: 477
ccuaguaggu guccaguaag u                                        21

<210> SEQ ID NO 478
<211> LENGTH: 20
<212> TYPE: RNA
<213> ORGANISM: Homo sapiens

<400> SEQUENCE: 478
ccucugggcc cuuccuccag                                          20

<210> SEQ ID NO 479
<211> LENGTH: 22
<212> TYPE: RNA
<213> ORGANISM: Homo sapiens

<400> SEQUENCE: 479
cuggcccucu cugcccuucc gu                                       22

<210> SEQ ID NO 480
<211> LENGTH: 23
```

```
<212> TYPE: RNA
<213> ORGANISM: Homo sapiens

<400> SEQUENCE: 480
gcaaagcaca cggccugcag aga                                              23

<210> SEQ ID NO 481
<211> LENGTH: 21
<212> TYPE: RNA
<213> ORGANISM: Homo sapiens

<400> SEQUENCE: 481
gccccugggc cuauccuaga a                                                21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu                                              23

<210> SEQ ID NO 483
<211> LENGTH: 23
<212> TYPE: RNA
<213> ORGANISM: Homo sapiens

<400> SEQUENCE: 483
uccagcuccu auaugaugcc uuu                                              23

<210> SEQ ID NO 484
<211> LENGTH: 23
<212> TYPE: RNA
<213> ORGANISM: Homo sapiens

<400> SEQUENCE: 484
uccagcauca gugauuuugu uga                                              23

<210> SEQ ID NO 485
<211> LENGTH: 21
<212> TYPE: RNA
<213> ORGANISM: Homo sapiens

<400> SEQUENCE: 485
ucccuguccu ccaggagcuc a                                                21

<210> SEQ ID NO 486
<211> LENGTH: 23
<212> TYPE: RNA
<213> ORGANISM: Homo sapiens

<400> SEQUENCE: 486
uccgucucag uuacuuuaua gcc                                              23

<210> SEQ ID NO 487
<211> LENGTH: 24
<212> TYPE: RNA
<213> ORGANISM: Homo sapiens

<400> SEQUENCE: 487
ucucacacag aaaucgcacc cguc                                             24

<210> SEQ ID NO 488
<211> LENGTH: 21
```

```
<212> TYPE: RNA
<213> ORGANISM: Homo sapiens

<400> SEQUENCE: 488
ugcugacucc uaguccaggg c                                              21

<210> SEQ ID NO 489
<211> LENGTH: 23
<212> TYPE: RNA
<213> ORGANISM: Homo sapiens

<400> SEQUENCE: 489
ugucugcccg caugccugcc ucu                                            23

<210> SEQ ID NO 490
<211> LENGTH: 22
<212> TYPE: RNA
<213> ORGANISM: Homo sapiens

<400> SEQUENCE: 490
aauugcacuu uagcaauggu ga                                             22

<210> SEQ ID NO 491
<211> LENGTH: 22
<212> TYPE: RNA
<213> ORGANISM: Homo sapiens

<400> SEQUENCE: 491
acauagagga aauuccacgu uu                                             22

<210> SEQ ID NO 492
<211> LENGTH: 21
<212> TYPE: RNA
<213> ORGANISM: Homo sapiens

<400> SEQUENCE: 492
aauaauacau gguugaucuu u                                              21

<210> SEQ ID NO 493
<211> LENGTH: 21
<212> TYPE: RNA
<213> ORGANISM: Homo sapiens

<400> SEQUENCE: 493
gccugcuggg guggaaccug g                                              21

<210> SEQ ID NO 494
<211> LENGTH: 21
<212> TYPE: RNA
<213> ORGANISM: Homo sapiens

<400> SEQUENCE: 494
gugccgccau cuuuugagug u                                              21

<210> SEQ ID NO 495
<211> LENGTH: 23
<212> TYPE: RNA
<213> ORGANISM: Homo sapiens

<400> SEQUENCE: 495
aaagugcugc gacauuugag cgu                                            23

<210> SEQ ID NO 496
<211> LENGTH: 22
```

```
<212> TYPE: RNA
<213> ORGANISM: Homo sapiens

<400> SEQUENCE: 496
acucaaaaug ggggcgcuuu cc                                              22

<210> SEQ ID NO 497
<211> LENGTH: 23
<212> TYPE: RNA
<213> ORGANISM: Homo sapiens

<400> SEQUENCE: 497
gaagugcuuc gauuuuggggg ugu                                            23

<210> SEQ ID NO 498
<211> LENGTH: 22
<212> TYPE: RNA
<213> ORGANISM: Homo sapiens

<400> SEQUENCE: 498
uuauaauaca accugauaag ug                                              22
```